United States Patent
Greiner et al.

(10) Patent No.: US 9,198,828 B2
(45) Date of Patent: *Dec. 1, 2015

(54) IMPLANTABLE ELECTROACUPUNCTURE DEVICE AND METHOD FOR TREATING DEPRESSION, BIPOLAR DISORDER AND ANXIETY

(71) Applicant: Valencia Technologies Corporation, Valencia, CA (US)

(72) Inventors: Jeffrey H. Greiner, Valencia, CA (US); David K. L. Peterson, Valencia, CA (US); Chuladatta Thenuwara, Castaic, CA (US); Stacy O. Greiner, Valencia, CA (US)

(73) Assignee: Valencia Technologies Corporation, Valencia, CA (US)

( * ) Notice: Subject to any disclaimer, the term of this patent is extended or adjusted under 35 U.S.C. 154(b) by 195 days.
This patent is subject to a terminal disclaimer.

(21) Appl. No.: 13/630,322

(22) Filed: Sep. 28, 2012

(65) Prior Publication Data
US 2014/0214117 A1   Jul. 31, 2014

Related U.S. Application Data

(60) Provisional application No. 61/541,061, filed on Sep. 29, 2011, provisional application No. 61/606,995, filed on Mar. 6, 2012, provisional application No. 61/609,875, filed on Mar. 12, 2012, provisional
(Continued)

(51) Int. Cl.
*A61N 1/05* (2006.01)
*A61H 39/00* (2006.01)
(Continued)

(52) U.S. Cl.
CPC .......... *A61H 39/002* (2013.01); *A61N 1/36096* (2013.01); *A61N 1/36175* (2013.01);
(Continued)

(58) Field of Classification Search
CPC ............ A61N 1/3756; A61N 1/36117; A61N 1/3605; A61N 1/37205
USPC .............................. 607/2, 44–46, 72; 128/907
See application file for complete search history.

(56) References Cited

U.S. PATENT DOCUMENTS

| | | | |
|---|---|---|---|
| 4,031,899 A | | 6/1977 | Renirie |
| 4,157,720 A | * | 6/1979 | Greatbatch ..................... 607/36 |

(Continued)

FOREIGN PATENT DOCUMENTS

| | | |
|---|---|---|
| WO | WO 01/41869 | 6/2001 |
| WO | WO 02/00294 | 1/2002 |

(Continued)

OTHER PUBLICATIONS

Wheeler, Mark "Non-invasive therapy significantly improve depression, researchers say," ScienceDaily.com (Sep 6, 2010)., orig. published by UCLANews.
(Continued)

*Primary Examiner* — Nicole F. Lavert
*Assistant Examiner* — Jeremiah Kimball
(74) *Attorney, Agent, or Firm* — Bryant R. Gold

(57) ABSTRACT

An implantable electroacupuncture device (IEAD) treats depression, bipolar disorder or Anxiety through application of stimulation pulses applied at acupoints GV20 and/or EXHN3. The IEAD comprises an implantable, coin-sized, self-contained, leadless electroacupuncture device having at least two electrodes attached to an outside surface of its housing. The device generates stimulation pulses in accordance with a specified stimulation regimen. Power management circuitry within the device allows a primary battery, having a high internal impedance, to be used to power the device. The stimulation regimen generates stimulation pulses during a stimulation session of duration T3 minutes applied every T4 minutes. The duty cycle, or ratio T3/T4, is very low, no greater than 0.05. The low duty cycle and careful power management allow the IEAD to perform its intended function for several years.

28 Claims, 19 Drawing Sheets

Related U.S. Application Data application No. 61/672,257, filed on Jul. 16, 2012, provisional application No. 61/672,661, filed on Jul. 17, 2012, provisional application No. 61/674,691, filed on Jul. 23, 2012, provisional application No. 61/676,275, filed on Jul. 26, 2012.

(51) Int. Cl.

| | |
|---|---|
| *A61N 1/36* | (2006.01) |
| *A61N 1/375* | (2006.01) |
| *A61N 1/372* | (2006.01) |
| *A61N 1/378* | (2006.01) |

(52) U.S. Cl.
CPC .......... *A61N1/3756* (2013.01); *A61N 1/37205* (2013.01); *A61N 1/36117* (2013.01); *A61N 1/36125* (2013.01); *A61N 1/3782* (2013.01); *Y10T 29/49002* (2015.01)

(56) References Cited

U.S. PATENT DOCUMENTS

| | | | |
|---|---|---|---|
| 4,345,604 A | 8/1982 | Renirie | |
| 4,528,072 A | 7/1985 | Kurosawa | |
| 4,535,784 A | 8/1985 | Rohlicek | |
| 4,566,064 A | 1/1986 | Whitaker | |
| 5,195,517 A | 3/1993 | Chen | |
| 5,199,428 A | 4/1993 | Obel | |
| 5,211,175 A * | 5/1993 | Gleason et al. | 600/548 |
| 5,250,068 A | 10/1993 | Ideguchi | |
| 5,251,637 A | 10/1993 | Shalvi | |
| 5,372,605 A | 12/1994 | Adams | |
| 5,544,656 A | 8/1996 | Pitsillides | |
| 5,609,617 A * | 3/1997 | Shealy et al. | 607/68 |
| 5,707,400 A | 1/1998 | Terry, Jr. | |
| 5,891,181 A | 4/1999 | Zhu | |
| 6,006,134 A | 12/1999 | Hill | |
| 6,178,352 B1 | 1/2001 | Gruzdowich | |
| 6,393,324 B2 | 5/2002 | Gruzdowich | |
| 6,522,926 B1 | 2/2003 | Kieval | |
| 6,658,298 B2 | 12/2003 | Gruzdowich | |
| 6,735,475 B1 | 5/2004 | Whitehurst | |
| 6,839,596 B2 | 1/2005 | Nelson | |
| 6,950,707 B2 | 9/2005 | Whitehurst | |
| 6,978,174 B2 | 12/2005 | Gelfand | |
| 7,003,352 B1 | 2/2006 | Whitehurst | |
| 7,013,177 B1 | 3/2006 | Whitehurst | |
| 7,046,499 B1 | 5/2006 | Imani | |
| 7,136,701 B2 | 11/2006 | Greatbach | |
| 7,155,279 B2 | 12/2006 | Whitehurst | |
| 7,162,303 B2 | 1/2007 | Levin | |
| 7,171,266 B2 | 1/2007 | Gruzdowich | |
| 7,203,548 B2 | 4/2007 | Whitehurst | |
| 7,292,890 B2 | 11/2007 | Whitehurst | |
| 7,321,792 B1 | 1/2008 | Min | |
| 7,373,204 B2 * | 5/2008 | Gelfand et al. | 607/44 |
| 7,440,806 B1 | 10/2008 | Whitehurst | |
| 7,444,180 B2 * | 10/2008 | Kuzma et al. | 607/2 |
| 7,610,100 B2 | 10/2009 | Jaax | |
| 7,620,451 B2 | 11/2009 | Demarais | |
| 7,657,316 B2 | 2/2010 | Jaax | |
| 7,962,219 B2 | 6/2011 | Jaax | |
| 2003/0078642 A1 | 4/2003 | Malaney | |
| 2003/0158588 A1 | 8/2003 | Rizzo | |
| 2003/0171790 A1 * | 9/2003 | Nelson et al. | 607/60 |
| 2003/0187485 A1 | 10/2003 | Sturman | |
| 2003/0195583 A1 * | 10/2003 | Gruzdowich et al. | 607/45 |
| 2003/0195585 A1 | 10/2003 | Gruzdowich | |
| 2003/0220668 A1 * | 11/2003 | Shealy | 607/2 |
| 2005/0107832 A1 | 5/2005 | Bernabei | |
| 2005/0228460 A1 | 10/2005 | Levin | |
| 2005/0234533 A1 | 10/2005 | Schulman | |
| 2006/0041283 A1 * | 2/2006 | Gelfand et al. | 607/44 |
| 2007/0005119 A1 | 1/2007 | Crohn | |
| 2007/0219595 A1 * | 9/2007 | He | 607/36 |
| 2007/0255319 A1 | 11/2007 | Greenberg | |
| 2007/0265680 A1 | 11/2007 | Liu | |
| 2008/0015572 A1 | 1/2008 | Johnson | |
| 2008/0091255 A1 | 4/2008 | Caparso | |
| 2009/0192555 A1 | 7/2009 | Schleicher | |
| 2009/0210026 A1 | 8/2009 | Solberg | |
| 2009/0292341 A1 | 11/2009 | Parramon | |
| 2010/0069992 A1 | 3/2010 | Aghassian | |
| 2010/0211132 A1 | 8/2010 | Nimmagadda | |
| 2010/0324624 A1 | 12/2010 | Chang | |
| 2010/0327887 A1 | 12/2010 | Denison | |
| 2011/0106219 A1 * | 5/2011 | Cauller et al. | 607/72 |
| 2011/0106220 A1 | 5/2011 | Degiorgio | |
| 2011/0112603 A1 | 5/2011 | Degiorgio | |
| 2011/0172739 A1 | 7/2011 | Mann | |
| 2011/0218589 A1 | 9/2011 | Degiorgio | |
| 2011/0218590 A1 | 9/2011 | Degiorgio | |
| 2011/0218859 A1 | 9/2011 | Wang | |
| 2012/0022612 A1 | 1/2012 | Littlewood | |
| 2012/0259390 A1 | 10/2012 | Canion | |
| 2013/0041396 A1 | 2/2013 | Ryotokuji | |

FOREIGN PATENT DOCUMENTS

| | | |
|---|---|---|
| WO | WO 2014-159433 | 10/2014 |
| WO | WO 2014/165111 | 10/2014 |

OTHER PUBLICATIONS

"Trigeminal nerve stimulation significantly improves depression", www.psypost.org, Friday, Sep. 3, 2010.
Lewis, D. "Trigeminal nerve stimulation for depression", www.helpfordepression.com (Sep. 15, 2011).
Cheung, et al. "The mechanism of acupuncture therapy and clinical case studies", (Taylor & Francis, publisher) (2001) ISBN 0-415-27254-8. The Forward, Chapters 1-3, 5, 7, 8, 12 & 13.
Swartz, KL. The John Hopkins White Papers: Depression and Anxiety. 2011.
Luo 1985; 'Clinical research on the therapeutic effect of the electro-acupuncture treatment in patients with depression.' Psychiatry Clinical Neuroscience 1998; 52 Suppl: S338-S340.
Quirico Pe, Pedrali T. Teaching Atlas of Acupuncture, vol. 1: Channels & Points. Georg Thieme Verlag. 2007., p. 185.
Who Standard Acupuncture Point Locations in the Western Pacific Region, published by the World Health Organization (WHO), Western Pacific Region, 2008 (updated and reprinted 2009), ISBN 978 92 9061 248 7. Table of Contents, Forward (page v-vi), General Guidelines for Acupuncture Point Locations (1-21), pp. 203 & 213.
Luo H, Shen Y, Meng F, Jia Y, Zhao X, Guo H & Feng X. "Preliminary research on treatment of common mental disorders with computer controlled electroacupuncture." Chin J Integr Med 1996; 2(2): 98-100.
"Acupuncture Today: Electroacupuncture". Jan. 2, 2004 (http://www.acupuncturetoday.com/abc/electroacupuncture.php).
Liu Q, Yu J. "Beneficial Effect of Acupuncture on Depression." Acupuncture Therapy for Neurological Diseases. Springer. 2010; 437-39.
Han C, Li X, Luo H, Zho X, Li X. "Clinical study on electro-acupuncture treatment for 30 cases of mental depression." J Tradit Chin Med 2004; 24(3): 172-6.
Meng F, Luo H, Shen Y, Shu L, Liu J. "Plasma NE concentrations and 24 hours urinary MHPG SO4 excretion changes after electro-acupuncture treatment in endogenous depression." World J. Acup-Mox. 1994; 4:45-52.
Jin GL, Zhou DF, Su J. "The effect of electro-acupuncture on chronic stress-induced depression in rat brain's monoamine neurotransmitters." Chin J Psychiatry. 1999; 32: 220-222.
Luo H, Ureil H, Shen Y. Comparative study of electroacupuncture and fluoxetine for treatment of depression. Chin J. Psychiatry, 2003; 36(4): 215. Chinese with English abstract.
Luo 1985; "Clinical research on the therapeutic effect of the electro-acupuncture treatment in patients with depression." Psychiatry Clin Neurosci 1998;52 Supple:S338-S340.

(56) References Cited

OTHER PUBLICATIONS

Han 2006; Han C, Li XW, Luo HC. Comparative study of electroacupuncture and maprotiline in treating depression. Zhongguo Zhong Xi Yi Jie He Za Zhi. 2002; 22(7): 512-514. Chinese with English abstract.
Luo H, Shen Y, Meng F, Jia Y, Zhao X, Guo H, Feng X. "Preliminary research on treatment of common mental disorders with computer controlled electroacupuncture." Chin J Integr Med 1996; 2(2): 98-100.
Leo, Salvador, Ligot. 'A systematic review of randomized controlled trials of acupuncture in the treatment of depression.' Journal of Affective Disorders 2006.
Luo HC, Jia YK, Li Z. "Electro-acupuncture vs. amitriptyline in the treatment of depressive states." J Tradit Chin Med 1985;5:3-8.
Han C, Li X, Luo H. "Randomized clinical trial comparing the effects of electro-acupuncture and maprotiline in treating depression." Int J Clin Acupoint 2006; 15(1): 7-14.
Huang Q. Exploration of the clinical regularity of acupuncture-moxibustion treatment for depression. J Acupunct Tuina Sci 2009; 7: 57-60.
Fu WB, Fan L, Zhu XP, He Q, Wang L, Zhuang LX, Liu YS, Tang CZ, Li YW, Meng CR, Zhang HL, Yan J. [Acupuncture for treatment of depressive neurosis: a multi-center randomized controlled study] 2008. Zhongguo Zhen Jiu (Chinese Acupuncture & Moxibustion) 28(1):3-6. Chinese with English abstract.
Luo HC, Shen YC, Jia YK. [Clinical observation of electroacupuncture on 133 patients with depression in comparison with tricyclic amitriptyline]. Zhong Xi Yi Jie He Za Zhi 1998;8(2): 77-80; Chinese with English Abstract.
Acupuncture. http://en.wikipedia.org/wiki/Acupuncture.
Electroacupuncture. http://en.wikipedia.org/wiki/Electroacupuncture.
Meng F, Luo H, Shen Y, Shu L, Liu J. Plasma NE concentrations and 24 hours urinary MHPG SO4 excretion changes after electro-acupuncture treatment in endogenous depression. World J. Acup-Mox. 1994; 4: 45-52.
Wang H, Yu E, Zhao J. "Clinical analysis of common psychosis treated by electroacupuncture in 129 cases." Journal of Clinical Acupuncture and Moxbiusion. 1999; (1): 42.
Luo H, Shen Y, Meng F, Jia Y, Zhao X, Guo H Feng X. "Preliminary research on treatment of common mental disorders with computer controlled electroacupuncture." Chin J Integr Med 1996; 2(2): 98-100.
Chen E. Cross-Sectional Anatomy of Acupoints. Churchill Livingstone. 1995. P114.
Shrader L, Cook P, Maremont E, Degiorgio C. "Trigeminal nerve stimulation in major depressive disorder: first proof of concept in an open pilot trial." Epilepsy Behav 2011; 22:475-8.
"Trigeminal Nerve." http://en.wikipedia.org/wiki/trigeminalnerve.
Peterson, U.S. Appl. No. 61/673,254, filed Jul. 19, 2012.
Greiner, U.S. Appl. No. 61/541,061, filed Sep. 29, 2011.
Peterson, U.S. Appl. No. 61/606,995, filed Mar. 6, 2012.
Peterson, U.S. Appl. No. 61/609,875, filed Mar. 12, 2012.
Peterson, U.S. Appl. No. 61/672,257, filed Jul. 16, 2012.
Peterson, U.S. Appl. No. 61/672,661, filed Jul. 17, 2012.
Peterson, U.S. Appl. No. 61/674,691, filed Jul. 23, 2012.
Thenuwara, U.S. Appl. No. 61/676,275, filed Jul. 26, 2012.
Greiner, U.S. Appl. No. 61/575,869, filed Aug. 30, 2011.
Song, Kiseok, "The Compact Electro-Acupuncture System for Multi-Modal Feedback Electro-Acupuncture Treatment," 34th Annual International Conference of the IEEE EMBS, San Diego, CA, USA, Aug. 28-Sep. 1, 2012.

\* cited by examiner

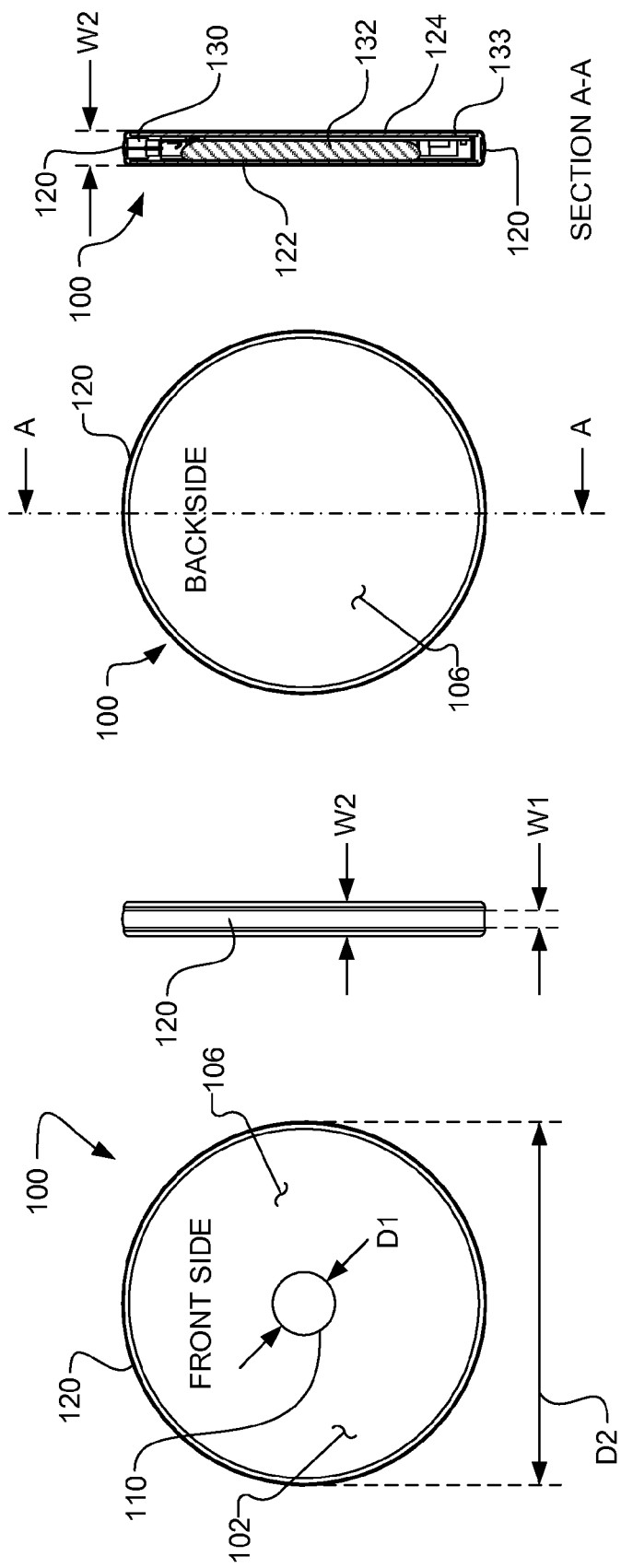

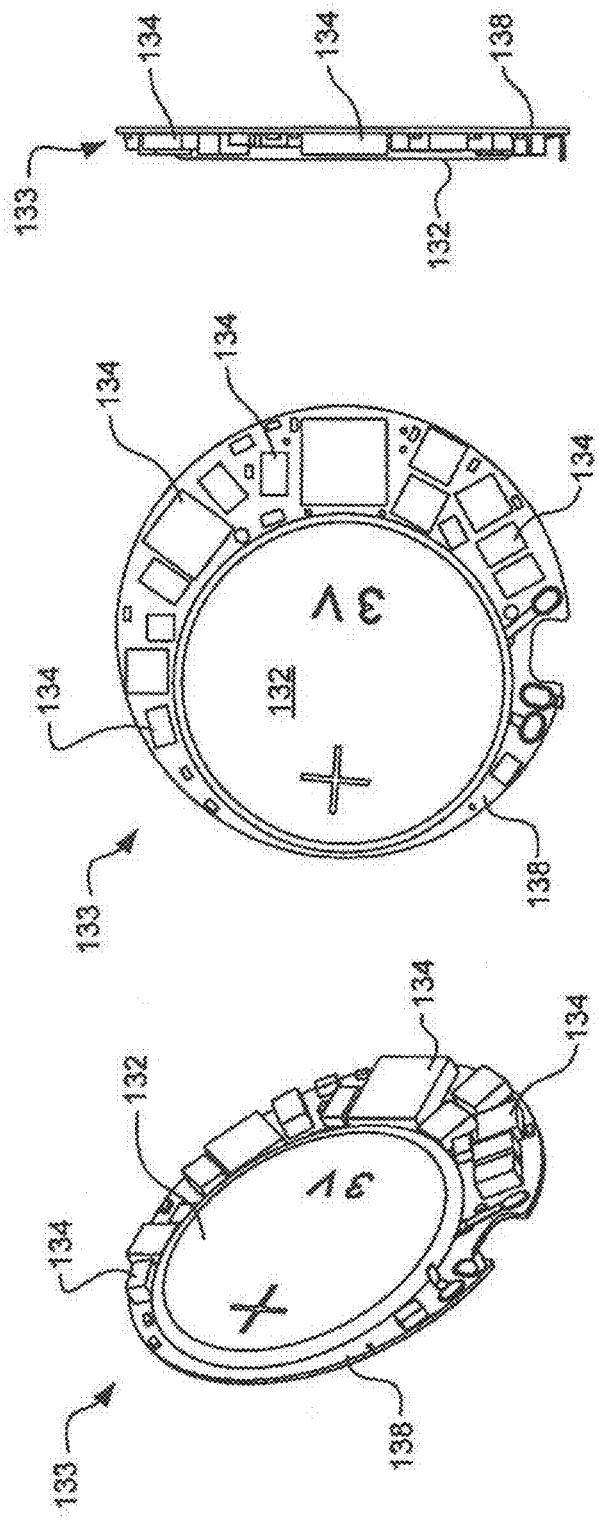

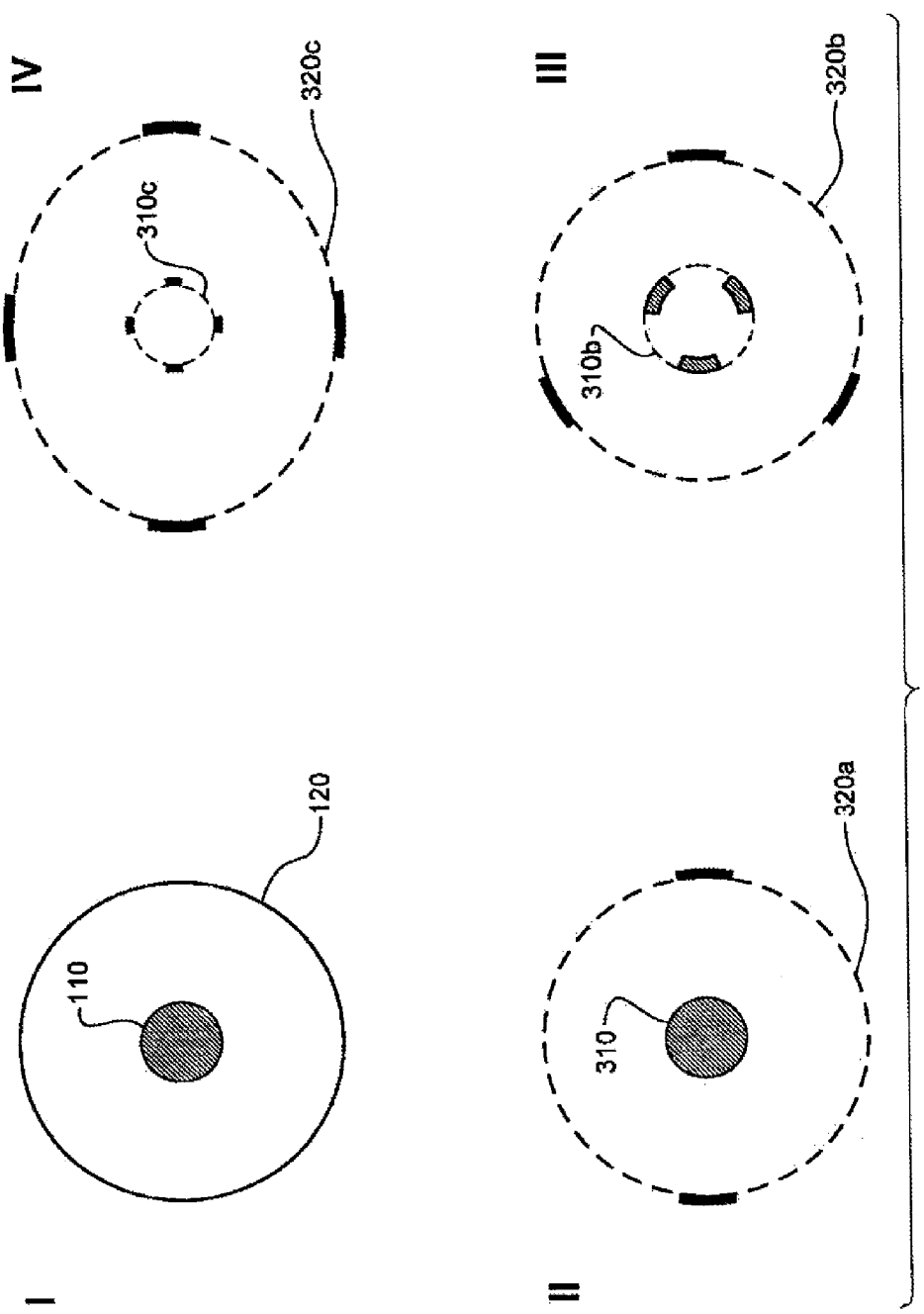

IMPLANTABLE ELECTROACUPUNCTURE DEVICE AND METHOD FOR TREATING DEPRESSION, BIPOLAR DISORDER AND ANXIETY

RELATED APPLICATIONS

This application claims the benefit of the following previously-filed provisional patent applications:
1. Implantable Electroacupuncture Device and Method For Treating Depression and Epilepsy, filed Sep. 29, 2011, Appl. No. 61/541,061, see Publication No.: US2014/0214118 A1, published Jul. 31, 2014;
2. Electrode Configuration For Implantable Electroacupuncture Device, filed Mar. 6, 2012, Appl. No. 61/606,995, see Publication No.: US2014/0214144 A1, published Jul. 31, 2014;
3. Boost Converter Output Control For Implantable Electroacupuncture Device, filed Mar. 12, 2012, Appl. No. 61/609,875, see Publication No.: US2014/0214128 A1, published Jul. 31, 2014;
4. Boost Converter Circuit Surge Control For Implantable Electroacupuncture Device Using Digital Pulsed Shutdown, filed Jul. 16, 2012, Appl. No. 61/672,257, see Publication No.: US2014/0214128 A1, published Jul. 31, 2014;
5. Smooth Ramp-Up Stimulus Amplitude Control For Implantable Electroacupuncture Device, filed Jul. 17, 2012, Appl. No. 61/672,661, see Publication No.: US2014/0214128 A1, published Jul. 31, 2014;
6. Pulse Charge Delivery Control In An Implantable Electroacupuncture Device, filed Jul. 23, 2012, Appl. No. 61/674,691, see Publication No.: US2014/0214128 A1, published Jul. 31, 2014;
7. Radial Feed-Through Packaging For An Implantable Electroacupuncture Device, filed Jul. 26, 2012, Appl. No. 61/676,275, see Publication No.: US2014/0214133 A1, published Jul. 31, 2014.

BACKGROUND

Depression is a chronic illness involving the mind and body. It is also called "major depression," "major depressive disorder," and "clinical depression." The American Psychiatric Association publishes a model for the classification of mental disorders. According to the model, "DSM-IV-TR," a person is suffering from a major depressive episode if he or she experiences items 1 or 2 from the list of symptoms below, along with any four others, continuously for more than two weeks:
1. Depressed mood with overwhelming feelings of sadness and grief.
2. Apathy—loss of interest and pleasure in activities formerly enjoyed.
3. Sleep problems—insomnia, early-morning waking, or oversleeping nearly every day.
4. Decreased energy or fatigue.
5. Noticeable changes in appetite and weight (significant weight loss or gain).
6. Inability to concentrate or think, or indecisiveness.
7. Physical symptoms of restlessness or being physically slowed down.
8. Feelings of guilt, worthlessness, and helplessness.
9. Recurrent thoughts of death or suicide, or a suicide attempt.

The prevalence of depression in the United States is profound, with almost 8% of the adult population suffering from at least one episode of major depression in the year 2007. The problem is serious and medications are insufficient to resolve the chronic illness for many adults.

Bipolar disorder affects about three percent of American men and women at some point in their lives. A person with the disorder typically has alternating periods of major depression and mania. In rare cases, mania can occur on its own. Episodes of mania are described as distinct periods of abnormally and persistently elevated, expansive, or irritable mood. Such episodes are severe enough to cause trouble at work, home, or both. The episodes can cause impaired judgment and often, excessive involvement in high-risk behavior. The time between episodes can vary greatly and men with bipolar disorder seem to have more manic episodes while women have more depressive episodes.

Generalized Anxiety Disorder (or "Anxiety" for short) is characterized by excessive, recurrent, and prolonged anxiety and worrying. See, Swartz, K. L., "The Johns Hopkins White Papers: Depression and Anxiety," Johns Hopkins Medicine (2011) (hereafter, "Swartz 2011"). People with Anxiety typically agonize over everyday concerns like job responsibilities, finances, health, or family well-being. They may even agonize about minor matters like household chores, car repairs, being late for appointments, or personal appearances. The focus of such anxiety may shift from one concern to the next and the severity of sensations may range from mild tension and nervousness to feelings of dread.

Anxiety affects about three percent of adult Americans each year. While people with the disorder know that the intensity, duration and frequency of their anxiety are generally unreasonably high, long, or frequent, they still have difficulty controlling their emotions. Continued anxiety may impair concentration, memory, decision-making, attention span, and confidence. While the effect of Anxiety on everyday activities is generally known, Anxiety may also produce physical symptoms including heart palpitations, restlessness, sweating, headaches, and nausea.

The most common treatment options for depression, bipolar disorder and Anxiety are medications and psychotherapy. Disadvantageously, only about thirty percent of patients reach full remission after a first medication. Moreover, the side effects of medications are serious, including but not limited to weight gain, sexual dysfunction, nausea, drowsiness, and fatigue. It is important to start treatment for depression, bipolar disorder and Anxiety early because the illness becomes more difficult to treat after its initial onset. Further, patients respond to treatments differently. Hence, it becomes very important to try different medications and alternative treatments if the initial treatment(s) is not effective.

From the above, it is seen that alternatives for treating depression, bipolar disorder and Anxiety are needed. Some alternative treatments for depression, in addition to psychotherapy (which is a key component for treating any mood disorder), include electroconvulsive therapy, light therapy (mostly for seasonal affective disorder), and neuromodulation. Highly invasive neuromodulation approaches include deep brain stimulation (DBS) and vagus nerve stimulation. Other neuromodulation treatments include repetitive transcranial magnetic resonance stimulation (rTMS) and transcranial direct-current stimulation.

Deep brain stimulation, or DBS, is theoretically viewed as the best location for stimulation to treat disorders such as depression, bipolar disorder and Anxiety because it applies the stimulation at the very core, or root, of the problem. Disadvantageously, however, DBS is a very risky procedure, and unless the stimulation is applied precisely at the location within the brain where needed, and using precise stimulation currents, serious damage can be done to the brain. Thus, in practice, given the current state of the art, DBS is used sparingly.

An attractive alternative to providing electrical stimulation pulses deep inside the brain is to apply electrical stimulation pulses to various nerves which lead to the brain. The idea is that, using nerves as pathways or conduits to the inside of the brain, it is possible to send signals to key structures deep in the brain without penetrating into the skull.

One nerve that provides "a high-bandwidth pathway into the brain," [quote attributed to Dr. Ian A. Cook, of the Semel Institute for Neuroscience and Human Behavior at UCLA, Los Angeles, Calif.], and which is the nerve (or its branches) used by some of the devices, methods and systems disclosed in this patent application to treat depression, bipolar disorder and Anxiety, is the Trigeminal nerve. The Trigeminal nerve is the fifth of 12 pairs of cranial nerves in the head. It is the nerve responsible for providing sensation to the face. One Trigeminal nerve runs to the right side of the head and the other to the left. Each of these nerves has three distinct branches. ("Trigeminal" derives from the Latin word "tria," which means three, and "geminus," which means twin.) After the Trigeminal nerve leaves the brain and travels inside the skull, it divides into three smaller branches, controlling sensations throughout the face.

The first branch of the Trigeminal nerve controls sensation in the eye, upper eyelid and forehead and is referred to as the "Opthalmic Nerve" or V1. The Supraorbital nerve is a part of this branch.

The second branch of the Trigeminal nerve controls sensation in the lower eyelid, cheek, nostril, upper lip and upper gum and is called the "Maxillary Nerve" or V2. Two prominent branches of the Maxillary nerve are the Zygomatic nerve and the Infraorbital nerve.

The third branch of the Trigeminal nerve controls sensations in the jaw, lower lip, lower gum and some of the muscles used for chewing. This third branch is called the "Mandibular Nerve" or V3.

The supraorbital nerve is a branch of the ophthalmic nerve (V). The supraorbital nerve courses from the forehead through the supraorbital notch (foramen) to join the supratrochlear nerve. The supratrochlear nerve carries information from the medial forehead, medial portion of the upper eyelid, and bridge of the nose.

U.S. Pat. No. 6,735,475, issued to Whitehurst et al., discloses use of an implantable miniature neurostimulator, referred to as a "microstimulator," that can be implanted into a desired tissue location and used as a therapy for headache and/or facial pain. The microstimulator has a tubular shape, with electrodes at each end. Stimulation of the Trigeminal nerve is mentioned in the patent, but not for purposes of treating depression.

Other patents of Whitehurst et al. teach the use of this small, microstimulator, placed in other body tissue locations, including within an opening extending through the skull into the brain, for the treatment of a wide variety of conditions, disorders and diseases. See, e.g., U.S. Pat. No. 6,950,707 (obesity and eating disorders); U.S. Pat. No. 7,003,352 (epilepsy by brain stimulation); U.S. Pat. No. 7,013,177 (pain by brain stimulation); U.S. Pat. No. 7,155,279 (movement disorders through stimulation of Vagus nerve with both electrical stimulation and drugs); U.S. Pat. No. 7,292,890 (Vagus nerve stimulation); U.S. Pat. No. 7,203,548 (cavernous nerve stimulation); U.S. Pat. No. 7,440,806 (diabetes by brain stimulation); U.S. Pat. No. 7,610,100 (osteoarthritis); and U.S. Pat. No. 7,657,316 (headache by stimulating motor cortex of brain).

Recently, some promising experimental neuromodulation approaches for the treatment of depression through stimulation of the Trigeminal nerve have appeared. See, e.g., "Non-Invasive Therapy Significantly Improves Depression, Researchers Say," ScienceDaily.com (Sep. 6, 2010); "Trigeminal nerve stimulation significantly improves depression", www.psypost.org, Friday, Sep. 3, 2010; Lewis, D. "Trigeminal Nerve Stimulation for Depression," www.helpforDpression.com (Sep. 15, 2011).

Further, there is at least one company, NeuroSigma, Inc., of Westwood, Calif., that is developing and commercializing neuromodulation treatments for a variety of disorders, including epilepsy, depression, post-traumatic stress disorder (PTSD), obesity, and cachexia. The therapy platforms used by NeuroSigma at the present comprise Trigeminal Nerve Stimulation (TNS) and Deep Brain Stimulation (DBS). See, e.g., the web site of NeuroSigma, Inc., found at http://www-.neurosigma.com/.

U.S. Patent Publications of DeGiorgio et al., US 2011/0106220, published May 5, 2011; US 2011/0112603 A1, published May 12, 2011; US 2011/0218859 A1, published Sep. 8, 2011; and US 2011/0218590 A1, published Sep. 8, 2011, describe and disclose, in some detail, the devices and methods used by NeuroSigma, Inc. in carrying out its TNS therapy platform for the treatment of depression and epilepsy, and other neurological or neuropsychiatric disorders. The four published patent applications referenced in this paragraph are incorporated herein by reference in their entireties. These four published patent applications appear to be assigned to The Regents of the University of California. The Regents of the University of California, in turn, appear to have recently executed an exclusive worldwide license for Trigeminal Nerve Stimulation (TNS) with NeuroSigma Inc., as reported in Science Daily (Sep. 6, 2010). See, e.g., the news release found at http://www.sciencedaily.com/releases/2010/09/110903092507.htm.

In general, two of the above four published US patent applications of DeGiorgio et al., US 2011/0112603 A1, published May 12, 2011 (hereafter the "603 Publication") and US 2011/0218590 A1, published Sep. 8, 2011 (hereafter the "'590 Publication"), relate primarily to TNS stimulation for treatment of depression and other mood disorders using either cutaneous electrodes ('590 Publication) or using at least one implantable electrode ('603 Publication). The other two of the above four published US Patent applications, US 2011/0106220, published May 5, 2011 (hereafter the "'220 Publication") and US 2011/0218859 A1, published Sep. 8, 2011 (hereafter the "859 Publication"), relate primarily to TNS stimulation for treatment of epilepsy and other neurological disorders and conditions using either cutaneous electrodes ('589 Publication) or using at least one implantable electrode ('220 Publication).

In the two DeGiorgio et al. published patent applications where an implantable electrode is used, electrical connection with the implantable electrode occurs by either (i) connecting an implanted electrical cable between the implantable electrode contacts and an implanted neurostimulator, see, e.g., the '603 Publication at Paragraph [0060], or (ii) making a wireless electrical connection between an external, non-implanted neurostimulator and the implantable electrode assembly through the use of inductive coupling. Id. Either way, when implantable electrode contacts are employed, there must either be significant tunneling through the tissue to allow a connecting cable to make electrical connection between the implanted neurostimulator device and electrode contacts, or additional circuitry with its accompanying complexity (and associated increased power consumption) must be employed within the external neurostimulator and/or the implanted electrode contacts to facilitate an enhanced inductively coupled connection.

Insofar as Applicant is aware, the '603 Publication represents the current state of the art for treating depression using implantable devices and methods that stimulate the Trigeminal nerve. Similarly, the '220 Publication represents the current state of the art for treating epilepsy using implantable devices and methods that stimulate the Trigeminal nerve. However, while the advance in the art described and presented in the '603 and '220 Publications is significant over prior neuromodulation therapy techniques for treating depression or epilepsy, improvements are still needed. For example, when implantable electrode contacts are employed, an efficient and safe mechanism must still be employed to electrically (or optically, or magnetically) connect the electrode contacts to a suitable pulse generator. If the pulse generator is external (non-implanted), either (i) the leads must pass through the skin (not a good thing to do over time because of infections and other concerns), or (ii) some sort of signal coupling mechanism, such as inductive or rf coupling, must be employed to allow the pulses generated by the pulse generator to be efficiently transferred to the electrode array and to specific electrode contacts included within the electrode array. If the pulse generator is implanted, a cable or lead must be tunneled through the body tissue from the implant location of the pulse generator to the implant location of the electrode contacts. Tunneling through body tissue, especially over a long distance, suffers from all the same risks associated with major surgery, as well as creates problems for the patient in the event of lead malfunction or breakage. Thus, it is seen that despite the advances made in the art, improvements are still needed.

Another alternative approach for treating depression, bipolar disorder and Anxiety, and a host of other physiological conditions, illnesses and deficiencies, is acupuncture, which includes traditional acupuncture, acupressure. Acupuncture has been practiced in Eastern civilizations (principally China, but also other Asian countries) for at least 2500 years. It is still practiced today throughout many parts of the world, including the United States and Europe. A good summary of the history of acupuncture, and its potential applications, may be found in Cheung, et al., "*The Mechanism of Acupuncture Therapy and Clinical Case Studies*", (Taylor & Francis, publisher) (2001) ISBN 0-415-27254-8, hereafter referred to as "Cheung, *Mechanism of Acupuncture,* 2001." The Forward, as well as Chapters 1-3, 5, 7, 8, 12 and 13 of Cheung, *Mechanism of Acupuncture,* 2001, are incorporated herein by reference.

Despite the practice in Eastern countries for over 2500 years, it was not until President Richard Nixon visited China (in 1972) that acupuncture began to be accepted in Western countries, such as the United States and Europe. One of the reporters who accompanied Nixon during his visit to China, James Reston, from the *New York Times*, received acupuncture in China for post-operative pain after undergoing an emergency appendectomy under standard anesthesia. Reston experienced pain relief from the acupuncture and wrote about it in *The New York Times*. In 1973 the American Internal Revenue Service allowed acupuncture to be deducted as a medical expense. Following Nixon's visit to China, and as immigrants began flowing from China to Western countries, the demand for acupuncture increased steadily. Today, acupuncture therapy is viewed by many as a viable alternative form of medical treatment, alongside Western therapies. Moreover, acupuncture treatment is now covered, at least in part, by most insurance carriers. Further, payment for acupuncture services consumes a not insignificant portion of healthcare expenditures in the U.S. and Europe. See, generally, Cheung, *Mechanism of Acupuncture,* 2001, vii.

Acupuncture is an alternative medicine that treats patients by insertion and manipulation of needles in the body at selected points. Novak, Patricia D. et al (1995). *Dorland's Pocket Medical Dictionary* (25th ed.). Philadelphia: (W.B. Saunders Publisher). ISBN 0-7216-5738-9. The locations where the acupuncture needles are inserted are referred to herein as "acupuncture points" or simply just "acupoints". The location of acupoints in the human body has been developed over thousands of years of acupuncture practice, and maps showing the location of acupoints in the human body are readily available in acupuncture books or online. For example, see, "Acupuncture Points Map," found online at: http://www.acupuncturehealing.org/acupuncture-points-map.html, Acupoints are typically identified by various letter/number combinations, e.g., L6, S37. The maps that show the location of the acupoints may also identify what condition, illness or deficiency the particular acupoint affects when manipulation of needles inserted at the acupoint is undertaken.

References to the acupoints in the literature are not always consistent with respect to the format of the letter/number combination. Some acupoints are identified by a name only, e.g., Tongli. The same acupoint may be identified by others by the name followed with a letter/number combination placed in parenthesis, e.g., Tongli (HT5). Alternatively, the acupoint may be identified by its letter/number combination followed by its name, e.g., HT5 (Tongli). The first letter typically refers to a body organ, or other tissue location associated with, or affected by, that acupoint. However, usually only the letter is used in referring to the acupoint, but not always. Thus, for example, the acupoint GV20 is the same as acupoint Governing Vessel 20 which is the same as GV-20 which is the same as GV 20 which is the same as Baihui. For purposes of this patent application, unless specifically stated otherwise, all references to acupoints that use the same name, or the same first letter and the same number, and regardless of slight differences in second letters and formatting, are intended to refer to the same acupoint.

An excellent reference book that identifies all of the traditional acupoints within the human body is *WHO STANDARD ACUPUNCTURE POINT LOCATIONS IN THE WESTERN PACIFIC REGION*, published by the World Health Organization (WHO), Western Pacific Region, 2008 (updated and reprinted 2009), ISBN 978 92 9061 248 7 (hereafter "*WHO Standard Acupuncture Point Locations* 2008"). The Table of Contents, Forward (page v-vi) and General Guidelines for Acupuncture Point Locations (pages 1-21), as well as pages 203 and 213 (which pages illustrate with particularity the location of acupoint GV20) of the *WHO Standard Acupuncture Point Locations* 2008, and page 185 of The Teaching Atlas of Acupuncture, see, Quirico P E, Pedrali T. *Teaching Atlas of Acupuncture*, Volume 1: Channels and Points. Georg Thieme Verlag. 2007, (which illustrates the location of acupoint EX Yintang, also referred to as acupoint EXHN3), are included herewith as Appendix D.

While many in the scientific and medical community are highly critical of the historical roots upon which acupuncture has developed, (e.g., claiming that the existence of meridians, qi, yin and yang, and the like have no scientific basis), see, e.g., http://en.wikipedia.org/wiki/Acupuncture, few can refute the vast amount of successful clinical and other data, accumulated over centuries of acupuncture practice, that shows needle manipulation applied at certain acupoints is quite effective.

The World Health Organization and the United States' National Institutes of Health (NIH) have stated that acupuncture can be effective in the treatment of neurological conditions and pain. Reports from the USA's National Center for Complementary and Alternative Medicine (NCCAM), the American Medical Association (AMA) and various USA government reports have studied and commented on the efficacy of acupuncture. There is general agreement that acupuncture is safe when administered by well-trained practitioners using sterile needles, but not on its efficacy as a medical procedure.

An early critic of acupuncture, Felix Mann, who was the author of the first comprehensive English language acupuncture textbook *Acupuncture: The Ancient Chinese Art of Healing*, stated that "The traditional acupuncture points are no more real than the black spots a drunkard sees in front of his eyes." Mann compared the meridians to the meridians of longitude used in geography—an imaginary human construct. Mann, Felix (2000). *Reinventing acupuncture: a new concept of ancient medicine*. Oxford: Butterworth-Heinemann. pp. 14; 31. ISBN 0-7506-4857-0. Mann attempted to combine his medical knowledge with that of Chinese theory. In spite of his protestations about the theory, however, he apparently believed there must be something to it, because he was fascinated by it and trained many people in the West with the parts of it he borrowed. He also wrote many books on this subject. His legacy is that there is now a college in London and a system of needling that is known as "Medical Acupuncture". Today this college trains doctors and Western medical professionals only.

For purposes of this patent application, the arguments for and against acupuncture are interesting, but not that relevant. What is important is that a body of literature exists that identifies several acupoints within the human body that, rightly or wrongly, have been identified as having an influence on, or are otherwise somehow related to, the treatment of various physiological conditions, deficiencies or illnesses, including pain and other conditions associated with myocardial ischemia, such as angina pectoris. With respect to these acupoints, the facts speak for themselves. Either these points do or do not affect the conditions, deficiencies or illnesses with which they have been linked. The problem lies in trying to ascertain what is fact from what is fiction. This problem is made more difficult when conducting research on this topic because the insertion of needles, and the manipulation of the needles once inserted, is more of an art than a science, and results from such research become highly subjective. What is needed is a much more regimented approach for doing acupuncture research.

It should also be noted that other medical research, not associated with acupuncture research, has over the years identified nerves and other locations throughout a patient's body where the application of electrical stimulation produces a beneficial effect for the patient. Indeed, the entire field of neurostimulation deals with identifying locations in the body where electrical stimulation can be applied in order to provide a therapeutic effect for a patient. For purposes of this patent application, such known locations within the body are treated essentially the same as acupoints—they provide a "target" location where electrical stimulation may be applied to achieve a beneficial result, whether that beneficial result is to reduce pain, to treat myocardial ischemia, to treat hypertension, to treat cardiovascular disease, to treat depression, or to mitigate some other form of mental disorder (e.g., Anxiety, bipolar disorder) or condition of the patient.

Returning to the discussion regarding acupuncture, some have proposed applying moderate electrical stimulation at selected acupuncture points through needles that have been inserted at those points. See, e.g., http://en.wikipedia.org/wiki/Electroacupuncture. Such electrical stimulation is known as electroacupuncture (EA). According to Acupuncture Today, a trade journal for acupuncturists: "Electroacupuncture is quite similar to traditional acupuncture in that the same points are stimulated during treatment. As with traditional acupuncture, needles are inserted on specific points along the body. The needles are then attached to a device that generates continuous electric pulses using small clips. These devices are used to adjust the frequency and intensity of the impulse being delivered, depending on the condition being treated. Electroacupuncture uses two needles at a time so that the impulses can pass from one needle to the other. Several pairs of needles can be stimulated simultaneously, usually for no more than 60 minutes at a time." "Acupuncture Today: Electroacupuncture". 2004 Feb. 1 (retrieved on-line Aug. 9, 2006 at http://www.acupuncturetoday.com/abc/electroacupuncture.php).

Similar techniques for using electrical devices, including external EA devices, for stimulating peripheral nerves and other body locations for treatment of various maladies are known in the art. See, e.g., U.S. Pat. Nos. 4,535,784; 4,566,064; 5,195,517; 5,250,068; 5,251,637; 5,891,181; 6,393,324; 6,006,134; 7,171,266; and 7,171,266. The methods and devices disclosed in these patents, however, typically utilize either large implantable stimulators having long leads that must be tunneled through tissue to reach the desired stimulation site, or use external devices that must interface with implanted electrodes via percutaneous leads or wires passing through the skin. Such devices and methods are still far too invasive, or are ineffective, and thus are subject to the same limitations and concerns, as are the previously described electrical stimulation devices.

From the above, it is seen that there is a need in the art for a less invasive device and technique for electroacupuncture stimulation of acupoints that does not require the continual use of needles inserted through the skin, or long insulated wires implanted or inserted into blood vessels, for the purposes of treating mental disorders, such as depression, Anxiety, or bi-polar disorder.

SUMMARY

One characterization of the invention described herein is an Implantable ElectroAcupuncture Device (IEAD) that treats depression, bipolar disorder or Anxiety through the application of electroacupuncture (EA) stimulation pulses applied at acupoint GV20, located on the head at the midpoint of the connecting line between the auricular apices. Alternatively, the EA stimulation pulses may be applied at acupoint EXHN3, located on the forehead at the midpoint between the two medial ends of the eyebrow. Moreover, the EA stimulation pulses may be applied at both acupoints GV20 and EXHN3. More detailed descriptions and illustrations of the location of acupoints GV20 and EXHN3 are found in Appendix D.

The IEAD in accordance with this characterization of the invention includes: (1) a small IEAD housing having an electrode configuration thereon that includes at least two electrodes, (2) pulse generation circuitry located within the IEAD housing that delivers EA stimulation pulses to the patient's body tissue at at least one acupoint EXHN3 or GV20, (3) a primary battery also located within the IEAD housing that provides the operating power for the IEAD to perform its intended function, and (4) a sensor located within the IEAD housing that is responsive to operating commands wirelessly communicated to the IEAD from a non-implanted location, these operating commands allowing limited external control of the IEAD, such as ON/OFF and EA stimulation pulse amplitude adjustment.

In one preferred embodiment, the IEAD housing used as part of the invention is coin-sized and -shaped, having a nominal diameter of 23 mm, and a thickness of only 2 to 3 mm.

Another preferred embodiment provides a symmetrical electrode configuration on the housing of the IEAD. Such symmetrical electrode configuration includes at least two electrodes, at least one of which is located substantially in the center of a first surface of the IEAD housing, and is referred to as a central electrode. The other electrode is symmetrically positioned around and at least 5 mm distant from the center of the central electrode, and is referred to as an annular or ring electrode (or, in some instances, as a circumscribing electrode). This symmetry between the central electrode and the annular electrode advantageously focuses the electric field, and hence the EA stimulation current created by application of an EA stimulation pulse to the electrodes, into the tissue adjacent the central electrode, where the desired EA stimulation at the selected acupoint, GV20 or EXHN3, occurs. One embodiment utilizes the centrally located electrode on a first surface of the IEAD housing as a cathode electrode and the annular electrode located on a perimeter edge of a coin-sized and -shaped IEAD housing as an anode electrode.

The pulse generation circuitry located within the IEAD housing is coupled to the at least two electrodes. This pulse generation circuitry is configured to generate EA stimulation pulses in accordance with a specified stimulation regimen. This stimulation regimen defines the duration and rate at which a stimulation session is applied to the patient. The stimulation regimen requires that the stimulation session have a duration of no more than T3 minutes and a rate of occurrence of no more than once every T4 minutes. The duty cycle of the stimulation sessions, i.e., the ratio of T3/T4, is very low, no greater than 0.05. A representative value for T3 is 30 minutes, but may range from 10 minutes to 72 minutes. A representative value for T4 is 7 days, but may range from 1 day to 14 days. The individual EA stimulation pulses that occur within the stimulation session also have a duty cycle measured relative to the period (the inverse of the frequency or rate of the stimulation pulses) of no greater than 5%. A representative pulse width and frequency for the EA stimulation pulses is 0.5 milliseconds, occurring at a pulse rate of 2 Hz.

The primary battery contained within the IEAD housing and electrically coupled to the pulse generation circuitry has a nominal output voltage of 3 volts, and an internal battery impedance that is at least 5 ohms, and may be as high as 150 ohms or more. Advantageously, electronic circuitry within the IEAD housing controls the value of the instantaneous surge current that may be drawn from the battery in order to prevent any large drops in the battery output voltage. Avoiding large drops in the battery output voltage assures that the circuits within the IEAD will continue to operate as designed without failure. Being able to use a primary battery that has a relatively high internal impedance allows the battery to be thinner, and thus allows the device to be thinner and more easily implanted. The higher internal impedance also opens the door to using relatively inexpensive commercially-available disc batteries as the primary battery within the IEAD, thereby greatly enhancing the manufacturability of the IEAD and significantly lowering its cost.

Another characterization of the invention described herein is a first method of treating (i) depression, (ii) bipolar disorder, or (iii) Anxiety in a patient using a leadless, coin-sized implantable electroacupuncture device (IEAD). Such IEAD is powered by a small disc battery having a specified nominal output voltage of about 3.0 volts, and having an internal impedance of at least 5 ohms.

The IEAD used to practice this first method is configured, using electronic circuitry within the IEAD, to generate EA stimulation pulses in accordance with a specified stimulation regimen. The EA stimulation pulses generated in accordance with this stimulation regimen are applied to the patient's tissue through at least two electrodes located on the housing of the IEAD. These at least two electrodes include at least one central electrode, located in the center of a first surface of the IEAD housing, and at least one annular electrode that surrounds the central electrode. The edge of the annular electrode closest to the central electrode is separated from the center of the central electrode by at least 5 mm.

Using such an IEAD, the depression, bipolar disorder or Anxiety treatment method treatment provided by this first method includes the steps of: (a) implanting the IEAD below the skin surface of the patient at acupoint(s) GV20 and/or EXHN3; and (b) enabling the IEAD to provide stimulation pulses in accordance with a specified stimulation regimen.

The specified stimulation regimen, when enabled, provides a stimulation session at a rate of once every T4 minutes, with each stimulation session having a duration of T3 minutes. The ratio of T3/T4 is no greater than 0.05. A preferred stimulation session time T3 is 60 minutes, but T3 could be as short as 10 minutes or as long as 72 minutes. A preferred time between stimulation sessions T4 is 7 days, but it could be as short as 1 day or as long as 14 days, to suit the needs of a particular patient.

Still further, the invention described herein may be characterized as a second method for treating a mood disorder, such as depression, Anxiety or bipolar disorder, in a patient. This second method comprises the steps of: (a) implanting a coin-sized electroacupuncture (EA) device in the patient just below the patient's skin at acupoint(s) GV20 and/or EXHN3; (b) enabling the EA device to generate EA stimulation sessions at a duty cycle that is less than or equal to 0.05, wherein each stimulation session comprises a series of EA stimulation pulses; and (c) delivering the EA stimulation pulses of each stimulation session to the specified acupoint(s) through at least two electrodes attached to an outside surface of the EA device. For purposes herein, the duty cycle of the stimulation sessions is defined as the ratio of T3/T4, where T3 is the duration in minutes of each stimulation session, and T4 is the time in minutes between stimulation sessions.

In a preferred application for this second method, the electrodes attached to the outside surface of the EA device are arranged in a symmetrical pattern. This symmetrical pattern of electrodes advantageously concentrates, or focuses, the electric field emanating from the electrode(s) into the tissue at the selected acupoint to a location within the tissue where the electroacupuncture stimulation is most effective.

Additionally, the invention described herein may be characterized as a method of assembling an implantable electroacupuncture device (IEAD) for use in treating mental illness (e.g., depression, Anxiety or bipolar disorder). The IEAD is assembled so as to reside in a thin, hermetically-sealed, coin-sized housing. An important feature of the coin-sized housing, and the method of assembly associated therewith, is that it electrically and thermally isolates a feed-through pin assembly radially passing through a wall of the coin-sized housing from the high temperatures associated with welding the housing closed to hermetically seal its contents. Such method of assembling includes the steps of:

a. forming a coin-sized housing having an open case and a cover plate, the cover plate being adapted to fit over the open case, the open case having a diameter D2 that is nominally 23 mm and a perimeter side wall extending all the way around the perimeter of the open case, the perimeter side wall having a height W2, wherein the ratio of W2 to D2 is no greater than about 0.13;

b. forming a recess in one segment of the side wall, the recess extending radially inwardly from the side wall to a depth D3, and the recess having an opening in a bottom wall portion thereof;

c. hermetically sealing a feed-through assembly in the opening in the bottom of the recess, the feed-through assembly having an non-conductive shoulder through which a feed-through pin passes, a perimeter edge of the non-conductive shoulder fitting tightly within the opening at the bottom wall of the recess without allowing the feed-through pin to contact the edges of the opening, a distal end of the pin extending radially outward beyond the side wall of the bottom case, and a proximal end of the feed-through pin extending radially inward toward the center of the open case, wherein the feed-through pin assembly is hermetically bonded to the opening in the side wall at a location in the bottom of the recess that is a distance D3 from the perimeter side wall, thereby thermally isolating the feed-through assembly from the high temperatures that occur at the perimeter side wall when the cover plate is welded to the edge of the perimeter side wall;

d. attaching a central electrode to the thin, coin-sized housing at a central location on an outside surface of the feed-through housing;

e. inserting an electronic circuit assembly, including a battery, inside of the open case, and connecting the proximal end of the feed-though pin to an output terminal of the electronic circuit assembly, and electrically connecting the open case to a reference terminal of the battery;

f. removing moisture from the open case, back filling with a mixture of He/Ar inert gas, and then welding the cover plate to the edges of the side wall of the bottom case, thereby hermetically sealing the electronic circuit assembly, including the battery, inside of the thin, coin-sized IEAD housing;

g. leak testing the welded assembly to assure a desired level of hermeticity has been achieved;

h. placing an insulating layer of non-conductive material around the perimeter edge of the thin coin-sized housing, then placing a circumscribing electrode over the insulating layer of non-conductive material, and then electrically connecting the distal end of the feed-through pin to the circumscribing electrode; and i. covering all external surface areas of the thin, coin-sized housing with a layer of non-conductive material except for the circumscribing electrode around the perimeter of the coin-sized housing and the central electrode centrally located on an outside surface of the thin-coin-sized housing.

BRIEF DESCRIPTION OF THE DRAWINGS

The above and other aspects, features and advantages of the invention will be more apparent from the following more particular description thereof, presented in conjunction with the following drawings. These drawings illustrate various embodiments of the principles described herein and are part of the specification. The illustrated embodiments are merely examples and do not limit the scope of the disclosure.

FIG. 2 shows a plan view of one surface or side (indicated as the "Front Side") of the IEAD housing illustrated in FIG. 1.

FIG. 2A shows a side view of the IEAD housing illustrated in FIG. 1.

FIG. 3 shows a plan view of the other side, indicated as the "Back Side," of the IEAD housing or case illustrated in FIG. 1.

FIG. 3A is a sectional view of the IEAD of FIG. 3 taken along the line A-A of FIG. 3.

FIG. 6 is a perspective view of an electronic assembly, including a battery, that is adapted to fit inside of the empty housing of FIG. 4 and FIG. 5.

FIGS. 6A and 6B show a plan view and side view, respectively, of the electronic assembly shown in FIG. 6.

FIG. 7A schematically illustrates a few alternative electrode configurations that may be used with the invention.

Figure 1:
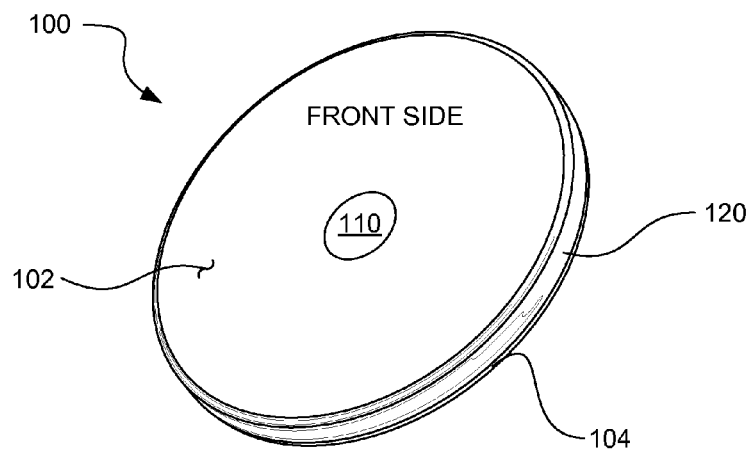
FIG. 1 is a perspective view of an Implantable Electroacupuncture Device (IEAD) made in accordance with the teachings presented herein.

Appendix A, submitted herewith, illustrates some examples of alternate symmetrical electrode configurations that may be used with an IEAD of the type described herein.

Appendix B, submitted herewith, illustrates a few examples of non-symmetrical electrode configurations that may be used with an IEAD made in accordance with the teachings herein.

Appendix C, submitted herewith, shows an example of the code used in the micro-controller IC (e.g., U2 in FIG. 14) to control the basic operation and programming of the IEAD, e.g., to Turn the IEAD ON/OFF, adjust the amplitude of the stimulus pulse, and the like, using only an external magnet as an external communication element.

Appendix D, submitted herewith, contains selected pages from the *WHO Standard Acupuncture Point Locations* 2008 reference book, referred to in paragraph [0029], as well as selected pages from Quirico P E, Pedrali T. *Teaching Atlas of Acupuncture*, Volume 1: Channels and Points. Georg Thieme Verlag. 2007, Appendices A, B, C and D are incorporated by reference herein, and comprise a part of the specification of this patent application.

Throughout the drawings and appendices, identical reference numbers designate similar, but not necessarily identical, elements.

DETAILED DESCRIPTION

Overview

Disclosed and claimed herein is an implantable, coin-shaped, self-contained, leadless electroacupuncture (EA) device having at least two electrode contacts mounted on the surface of its housing. In one preferred embodiment, the electrodes include a central cathode electrode on a front side of the housing, and an annular anode electrode that surrounds the cathode. In another preferred embodiment, the anode annular electrode is a ring electrode placed around the perimeter edge of the coin-shaped housing.

The EA device is leadless. This means there are no leads or electrodes at the distal end of leads (common with most implantable electrical stimulators) that have to be positioned and anchored at a desired stimulation site. Also, because there are no leads, no tunneling through body tissue or blood vessels is required in order to provide a path for the leads to return and be connected to a tissue stimulator (also common with most electrical stimulators).

The EA device is adapted to be implanted through a very small incision, e.g., less than 2-3 cm in length, directly adjacent to a selected acupuncture site ("acupoint") known to moderate or affect a mental illness or symptom of depression related to a patient's mental illness.

The EA device is relatively easy to implant. Also, most embodiments are symmetrical. This means that there is no way that it can be implanted incorrectly. The basic implant procedure involves cutting an incision, forming an implant pocket, and sliding the device in place through the incision. Only minor, local anesthesia need be used. No major or significant complications are envisioned for the implant procedure. The EA device can also be easily and quickly explanted, if needed.

The EA device is self-contained. It includes a primary battery to provide its operating power. It includes all of the circuitry it needs, in addition to the battery, to allow it to perform its intended function for several years. Once implanted, the patient should not even know it is there, except for a slight tingling that may be felt when the device is delivering stimulus pulses during a stimulation session. Also, once implanted, the patient can just forget about it. There are no complicated user instructions that must be followed. Just turn it on. No maintenance is needed. Moreover, should the patient want to disable the EA device, i.e., turn it OFF, or change stimulus intensity, he or she can do so using, e.g., an external magnet or other appropriate remote programming tool.

The EA device can operate for several years because it is designed to be very efficient. Stimulation pulses applied by the EA device at a selected acupoint through its electrodes formed on its case are applied at a very low duty cycle in accordance with a specified stimulation regimen. The stimulation regimen applies EA stimulation during a stimulation session that lasts at least 10 minutes, sometimes 30 minutes, and rarely longer than 70 minutes. These stimulation sessions, however, occur at a very low duty cycle. In one preferred treatment regimen, for example, a stimulation session having a duration of 60 minutes is applied to the patient just once every seven days. The stimulation regimen, and the selected acupoint at which the stimulation is applied, are designed and selected to provide efficient and effective EA stimulation for the treatment of the patient's mental illness (e.g., depression, Anxiety, or bipolar disorder).

The EA device is, compared to most implantable medical devices, relatively easy to manufacture and uses few components. This not only enhances the reliability of the device, but helps keep the manufacturing costs low, which in turn allows the device to be more affordable to the patient. One key feature included in the mechanical design of the EA device is the use of a radial feed-through assembly to connect the electrical circuitry inside of its housing to one of the electrodes on the outside of the housing. The design of this radial feed-through pin assembly greatly simplifies the manufacturing process. The process places the temperature sensitive hermetic bonds used in the assembly—the bond between a pin and an insulator and the bond between the insulator and the case wall—away from the perimeter of the housing as the housing is hermetically sealed at the perimeter with a high temperature laser welding process, thus preserving the integrity of the hermetic bonds that are part of the feed-through assembly.

In operation, the EA device is safe to use. There are no horrific failure modes that could occur. Because it operates at a very low duty cycle (i.e., it is OFF much, much more than it is ON), it generates little heat. Even when ON, the amount of heat it generates is not much, less than 1 mW, and is readily dissipated. Should a component or circuit inside of the EA device fail, the device will simply stop working. If needed, the EA device can then be easily explanted.

Another key feature included in the design of the EA device is the use of a commercially-available battery as its primary power source. Small, thin, disc-shaped batteries, also known as "coin cells," are quite common and readily available for use with most modern electronic devices. Such batteries come in many sizes, and use various configurations and materials. However, insofar as inventors or Applicant are aware, such batteries have never been used in implantable medical devices previously. This is because their internal impedance is, or has always thought to have been, much too high for such batteries to be of practical use within an implantable medical device where power consumption must be carefully monitored and managed so that the device's battery will last as long as possible, and so that dips in the battery output voltage (caused by any sudden surge in instantaneous battery current) do not occur that could compromise the performance of the device. Furthermore, the energy requirements of other active implantable therapies are far greater than can be provided by such coin cells without frequent replacement.

The EA device disclosed herein advantageously employs power-monitoring and power-managing circuits that prevent any sudden surges in battery instantaneous current, or the resulting drops in battery output voltage, from ever occurring, thereby allowing a whole family of commercially-available, very thin, high-output-impedance, relatively low capacity, small disc batteries (or "coin cells") to be used as the EA device's primary battery without compromising the EA device's performance. As a result, instead of specifying that the EA device's battery must have a high capacity, e.g., greater than 200 mAh, with an internal impedance of, e.g., less than 5 ohms, which would either require a thicker battery and/or preclude the use of commercially-available coin-cell batteries, the EA device of the present invention can readily employ a battery having a relatively low capacity, e.g., less than 60 mAh, and a high battery impedance, e.g., greater than 5 ohms.

Moreover, the power-monitoring, power-managing, as well as the pulse generation, and control circuits used within the EA device are relatively simple in design, and may be readily fashioned from commercially-available integrated circuits (IC's) or application-specific integrated circuits (ASIC's), supplemented with discrete components, as needed. In other words, the electronic circuits employed within the EA device need not be complex nor expensive, but are simple and inexpensive, thereby making it easier to manufacture the EA device and to provide it to patients at an affordable cost.

DEFINITIONS

As used herein, "annular", "circumferential", "circumscribing", "surrounding" or similar terms used to describe an electrode or electrode array, or electrodes or electrode arrays, (where the phrase "electrode or electrode array," or "electrodes or electrode arrays," is also referred to herein as "electrode/array," or "electrodes/arrays," respectively) refers to an electrode/array shape or configuration that surrounds or encompasses a point or object, such as another electrode, without limiting the shape of the electrode/array or electrodes/arrays to be circular or round. In other words, an "annular" electrode/array (or a "circumferential" electrode/array, or a "circumscribing" electrode/array, or a "surrounding" electrode/array), as used herein, may be many shapes, such as oval, polygonal, starry, wavy, and the like, including round or circular.

"Nominal" or "about" when used with a mechanical dimension, e.g., a nominal diameter of 23 mm, means that there is a tolerance associated with that dimension of no more than plus or minus (+/−) 5%. Thus, a dimension that is nominally 23 mm means a dimension of 23 mm+/−(0.05×23 mm=1.15 mm).

"Nominal" when used to specify a battery voltage is the voltage by which the battery is specified and sold. It is the voltage you expect to get from the battery under typical conditions, and it is based on the battery cell's chemistry. Most fresh batteries will produce a voltage slightly more than their nominal voltage. For example, a new nominal 3 volt lithium coin-sized battery will measure more than 3.0 volts, e.g., up to 3.6 volts under the right conditions. Since temperature affects chemical reactions, a fresh warm battery will have a greater maximum voltage than a cold one. For example, as used herein, a "nominal 3 volt" battery voltage is a voltage that may be as high as 3.6 volts when the battery is brand new, but is typically between 2.7 volts and 3.4 volts, depending upon the load applied to the battery (i.e., how much current is being drawn from the battery) when the measurement is made and how long the battery has been in use.

Conditions Treated, Selected Acupoints and Stimulation Regimen

As indicated previously, the electroacupuncture (EA) device and methods disclosed herein are aimed at treating: (i) depression, (ii) bipolar disorder, or (iii) Anxiety. These three mental illnesses have been described previously. See, e.g., paragraphs [0002]-[0007]. The mechanism of action associated with each of these three conditions is described in more detail in the paragraphs that follow. This description is followed by (iv) an explanation of how acupoints GV20 and EXHN3 were identified by Applicant as the best candidates for receiving EA stimulation for treatment of these conditions. Then, (v) a brief description of the preferred stimulation regimen is presented.

(i) Depression

Studies on the mechanism of acupuncture for depression have been carried out with respect to some central neurotransmitters, Hypothalamus-pituitary-adrenal (HPA) axis, immune system, limbic system including the hippocampus and amygdala as well as the anterior thalamic nuclei and limbic cortex, and the signal transduction system in the nerve cell. See, Liu Q, Yu J. Beneficial Effect of Acupuncture on Depression. *Acupuncture Therapy for Neurological Diseases*. Springer. 2010; 437-39 (herafter, "Liu 2010"). These studies have made some progress in understanding the mechanism of acupuncture for depression, but the complete mechanism requires further investigation.

In a study performed by Han et al., electroacupuncture was performed at acupoints GV20 and EXHN3 among several other points (the selection of which depended upon the type of depression diagnosed according to traditional chinese medicine). The levels of cortisol content and endothelin-1 content were decreased to normal levels after EA. See, Han C, Li X, Luo H, Zho X, Li X. Clinical Study on Electro-acupuncture Treatment for 30 Cases of Mental Depression. J Tradit Chin Med 2004; 24(3): 172-6 (hereafter, "Han 2004"). Additionally, the condition of depression in those patients treated with EA was improved; treated patients with an average baseline score on the Hamilton Rating Scale for Depression (HRSD) of 30.15 were found to have scores on average of 11.73 after six weeks of treatment.

Another theory is that electroacupuncture is able to release monoamines in the central nervous system while depressed patients generally exhibit reduced metabolism of monoamine neurotransmitters. Biochemical studies of some depressed patients who participated in an electroacupuncture study done by Meng et al. showed that their plasma norepinephrine level changed greatly after EA treatment. See, Meng F, Luo H, Shen Y, Shu L, Liu J. Plasma NE Concentrations and 24 Hours Urinary MHPG $SO_4$ Excretion Changes After Electro-Acupuncture Treatment in Endogenous Depression. World J. Acup-Mox. 1994; 4:45-52 (hereafter, "Meng 1994"). It is suggested that the therapeutic effect of electroacupuncture at GV20 and EXHN3 is found by acting on the metabolic mechanism of norepinephrine in the central nervous system. See, Meng 1994.

In addition to the regulation of norepinephrine levels in the brain, EA may improve depression by its balancing of serotonin (along with norepinephrine) levels in the brain. In a study conducted by Jin et al., the mechanism of electroacupuncture of the acupoints GV20 and EXHN3 was studied in rats. See, Jin G L, Zhou D F, Su J. The effect of electro-acupuncture on chronic stress-induced depression in rat brain's monoamine neurotransmitters. Chin J. Psychiatry. 1999; 32: 220-222 (hereafter, "Jin 1999"). In the male Sprague-Dawley rats, four groups were created: a control group, a depression model, a depression model where EA was applied, and a depression model with the use of the drug amitriptyline. In the depression model, the serotonin receptors or serotonin metabolite ("5-Hydroxytryptamine (5-HT)" or "5-Hydroxy-indoleacetic acid (5-HIAA)", respectively) in the cortex and the metabolite of the neurotransmitter dopamine ("DA/3,4-dihydroxyphenylacetic acid (DOPAC)") in the striatum were shown to be significantly lower than those in the control group. After EA treatment, 5-HT/5-HIAA and NE/5-HT in the cortex returned to normal level, and the decrease in the DA/DOPAC in the striatum was not affected by EA. Thus, it appears that the stimulation at GV20 and EXHN3 could increase the activity of the 5-HT-type neuron by decreasing the 5-HT metabolism in the cortex, which could rebuild the balance of NE and 5-HT and produce a potential antidepressant effect.

Thus, while the mechanism of action is not well understood, there is significant evidence that both symptoms and scales of depression may be improved by electroacupuncture and that certain neurotransmitters are likely involved.

(ii) Anxiety

In an abstract published in English in 2003, electroacupuncture (EA) applied at acupoints EXHN3 and GV20 was shown to improve depression as a whole, based upon the Hamilton Rating Scale for Depression (HRSD) which also measures Anxiety. When compared to the anti-anxiety medication fluoxetine (commonly known by the brand "Prozac"), more improvement was seen in the EA group. See, Luo H, Ureil H, Shen Y. Comparative study of electroacupuncture and fluoxetine for treatment of depression. Chin J Psychiatry, 2003; 36(4): 215. Chinese with English abstract (hereafter, "Luo 2003").

In studies done by Luo et al. where EA is compared with antidepressants, EA proves to do better than the drug in the improvement of Anxiety. See, e.g., Luo 1985; Clinical research on the therapeutic effect of the electro-acupuncture treatment in patients with depression. Psychiatry Clin Neurosci 1998; 52 Suppl:S338-S340 (hereafter, "Luo 1998").

In particular, in two studies conducted by Han et al, EA is shown to improve Anxiety levels better than the drug maprotiline, which is used to treat depression. See, Han 2006; Han C, Li X W, Luo H C. Comparative study of electro-acupuncture and maprotiline in treating depression. Zhongguo Zhong Xi Yi Jie He Za Zhi. 2002; 22(7): 512-514. Chinese with English Abstract (hereafter, "Han 2002").

Since serotonin and norepinephrine (along with gamma-aminobutyric acid or "GABA" and dopamine) are implicated in Anxiety, studies showing that EA changes levels of serotonin and norepinephrine in the brain suggest positive evidence for the treatment of Anxiety. See e.g., Jin 1999; Luo 1998.

Medications for the treatment of Anxiety disorders are available in six different classes: benzodiazepines, buspirone, selective serotonin reuptake inhibitors (SSRIs), serotonin and norepinephrine reuptake inhibitors (SNRIs), tetracylics, and tricyclics. See, Swartz 2011. Five of the six classes (all excluding benzodiazepines for which the mechanism is not well understood) involve the regulation of serotonin or norepinephrine—the neurotransmitters that are implicated in mechanism studies related to the present invention. Given that EA seems to do even better than two antidepressants and particularly, better than an SSRI fluoxetine indicated for Anxiety, the disclosed invention should prove successful to reduce anxiety in Anxiety disorders.

(iii) Bipolar Disorder

The existence of lower levels of norepinephrine are thought to be involved in bipolar disorder. Thus, evidence that acupuncture or EA at the selected points increases norepinephrine in depression models may be evidence for the successful treatment of bipolar disorder. See, e.g. Meng 1994; Jin 1999.

Similarly, decreased levels of serotonin are often found in people with bipolar disorder and depression. Since the serotonin receptors 5-HT were increased after EA, EA at the relevant acupoints should also improve bipolar disorder through the changes in levels of serotonin. See, Jin 1999.

Additionally, in at least three trials performing electroacupuncture at acupoints GV20 and EXHN3 and led by Luo, bipolar patients were included among the depressed patients. See, Luo H, Shen Y, Meng F, Jia Y, Zhao X, Guo H, Feng X. Preliminary Research on Treatment of Common Mental Disorders with Computer Controlled Electroacupuncture. Chin J Integr Med 1996; 2(2): 98-100 (hereafter, "Luo 1996"); Luo H, Jia Y, Wu X, Dai W. Electro-acupuncture in the treatment of depressive psychosis. Int J Clin Acupunct 1990; 1(1):7-13; Luo H, Meng F, Jia Y, Zhao X. Chinese with English abstract. (hereafter, Luo 1990); Luo 1998; Han 2006.

Bipolar disorder requires lifelong treatment that generally starts with medication. There are seven classes of medications used to treat bipolar disorder—and medications within three of the classes are also approved by the FDA to treat major depression. Those medications used to treat both major depression and bipolar disorder are: Abilify (aripiprazole), Risperdal (risperidone), Symbax (olanzapine/fluoxetine), and antidepressants as a whole. Symbyax, in particular, works by increasing the availability of the neurotransmitters serotonin, norepinephrine, and dopamine to treat depression associated with bipolar disorder. See, Swartz 2011. Likewise, antidepressants are prescribed to treat depression associated with bipolar disorder. The mechanism of action in the present invention (and its involvement of serotonin and norepinephrine) as has been previously described is similar to that known to be working in the approved aforementioned drugs.

(iv) Electroacupuncture (EA) Stimulation Points

With respect to the location where the inventors or applicant (hereafter "inventors or applicant" are referred to collectively as "Applicant") have chosen to apply EA stimulation for purposes of treating depression, Anxiety or bipolar disorder, the acupoint GV20, or a point near GV20, such as a point along an axis line connecting GV20 with a nearby acupoint, such as GV21 or GV19 is one preferred location. The location of acupoints GV19, GV20 and GV21 are illustrated in FIGS. 1A and 1B, and are further described on pages 203 and 213 of *WHO Standard Acupuncture Point Locations* 2008, previously incorporated herein by reference. Selected portions of *WHO Standard Acupuncture Point Locations* 2008, including pages 203 and 213 are included in Appendix D.

Another preferred location for EA application is acupoint EXHN3. The location of acupoint EXHN3 is also illustrated in FIG. 1A, and is further illustrated in Appendix D.

Additionally, a preferred location for EA application includes both acupoints GV20 and EXHN3.

The primary acupoints GV20 and EXHN3 have been selected, in part, because they are associated with increases in serotonin, suggesting a beneficial application in depression. See, e.g., Luo H C, Jia Y K, Li Z. Electro-acupuncture vs. amitriptyline in the treatment of depressive states. J Tradit Chin Med 1985; 5:3-8 (hereafter, "Luo 1985").

Additionally, in a selection of work performed by Dr. Luo Hechun et al., both manual acupuncture and electroacupuncture of these two points have brought about positive results in depression—results showing efficacy equal to that seen in drugs such as the tetracyclic maprotiline and the tricyclic antidepressant amitriptyline. See, e.g. Luo H, Meng F, Jia Y, Zhao X. Clinical research on the therapeutic effect of the electro-acupuncture treatment in patients with depression. Psychiatry Clin Neurosci 1998; 52 Suppl:S338-S340 (hereafter, "Luo 1998"); Han 2004; Han C, Li X, Luo H. Randomized Clinical Trial Comparing the Effects of Electro-acupuncture and Maprotiline in Treating Depression. Int J Clin Acupunct 2006; 15(1): 7-14 (hereafter, "Han 2006").

As is common in Eastern medical references, and has been previously described (see, e.g., Paragraph [0027], supra] acupoints are referred to using different names and terminology. The acupoint, Baihui, is also designated by DU20 and GV20. In acupuncture terminology, both "GV" and "DU" stand for the Governing Vessel meridian.

The acupoint Yintang, on the other hand, is designated by EXHN3. "EX" stands for extra or extraordinary while "HN" stands for head and neck. Yintang has also been described as GV24.5, probably to describe the point between GV24 and GV25 since EX points were not named until much later in acupuncture history. Like all acupoints, the letters designating acupoints Baihui and Yintang are often spaced differently depending upon the source. For example, EXHN3 is the same as EX-HN3, which is the same as EX-HN-3.

It should also be noted that acupoint Yintang or EXHN3 is also sometimes referred to as "Glabella."

It is possible that EXHN3 may have other names since its discovery was late in acupuncture history.

The acupoint GV20 is located on the head at the midpoint of the connecting line between the auricular apices. It is also about 4.5 inches superior to the anterior hairline on the anterior median line. It is depicted in FIG. 1B, and is further described and illustrated in Appendix D.

The acupoint EXHN3 is located on the forehead at the midpoint between the two medial ends of the eyebrow. Its location is shown in FIG. 1A, and is further described and illustrated in Appendix D, where it is also referred to as "Ex yin tang."

In two studies conducted by Luo et al. and published in 1998, the group performed electroacupuncture on twenty-nine depressed inpatients. See, Luo 1998. Following the successful results of the first study, the same group performed electroacupuncture using the same protocol on a larger group of 133 depressed inpatients, some of whom suffered from bipolar disorder. In this study, the electrical parameters used were low frequency and low amplitude. EA was done once a day for 6 days of the week over 6 weeks. Both studies, which had at least one control, were quite successful as measured by three different scales for measuring depression.

In addition to this key study, there is a large base of acupuncture work in depression for which many acupoints have been used. The acupoint GV20 is one of the most commonly used acupoints. See, Huang Q. Exploration of the Clinical Regularity of Acupuncture-moxibustion Treatment for Depression. J Acupunct Tuina Sci 2009; 7: 57-60 (hereafter, "Huang 2009"). In a review done by Huang et al., studies using acupuncture or moxibustion to treat depression published between 1956 and 2007 were reviewed. It was found that Baihui (GV20) and Neiguan (PC6) were most commonly used. See, supra.

Consistent with traditional Chinese medicine, acupoints are often selected in multiples of six to twelve, and (depending upon the particular symptoms and presentation of a patient) are generally chosen by the acupuncturist at the time of acupuncture. Thus, standardized acupuncture, until recently, is atypical.

Like the lack of agreement on the best stimulation regimen, there is not agreement on which acupoints are best fit to reduce depression and whether a standardized approach will best improve the condition. Applicant has identified GV20 and EXHN3 as the acupoints most fit to improve depression using its device following the stimulation regimens described herein. However, acupuncture promotes individualized approaches and thus the clinical work does not contemplate an implantable device or the practicality of limiting the number of acupoints used.

Applicant's implementation of using electroacupuncture delivered through a small, implantable EA device at selected acupoints has been guided, in part, on an analysis of successful and unsuccessful acupuncture studies for the treatment of depression. From such an analysis, and from work laid out by Luo's group, Applicant has identified GV20 and EXHN3 as the primary acupoints involved when depression is improved. See, e.g., Luo 1985; Luo 1990; Luo 1998; Han 2004; Fu W B, Fan L, Zhu X P, He Q, Wang L, Zhuang L X, Liu Y S, Tang C Z, Li Y W, Meng C R, Zhang H L, Yan J. [Acupuncture for treatment of depressive neurosis: a multi-center randomized controlled study] 2008. Zhongguo Zhen Jiu (Chinese Acupuncture & Moxibustion) 28(1):3-6. Chinese with English abstract; Luo H C, Shen Y C, Jia Y K. [Clinical study of electroacupuncture on 133 patients with depression in comparison with tricyclic amitriptyline]. Zhong Xi Yi Jie He Za Zhi 1988; 8(2):77-80. Chinese with English Abstract.

(v) Stimulation Regimen

For purposes of this patent application and for the treatment of depression, bipolar disorder or Anxiety, Applicant has determined that its EA device should be implanted at both GV20 and EXHN3 or at only one of these two points. Duration of a stimulation session will typically be at least about 30 minutes, but could be as short as about 10 minutes and as long as about one hour. The time between stimulation sessions (or the rate of occurrence of the stimulation session) may be as short as twenty-four hours and as long as two weeks. The duty cycle of the stimulation sessions, T3/T4, should never be allowed to be greater than 0.05, where T3 is the duration of the stimulation session, and T4 is the time period between the start of one stimulation session and the beginning of the next stimulation session.

By way of example, if T3 is 30 minutes, and T4 is 2 weeks (10080 minutes), then the duty cycle is 30/10080=0.003 (a very low stimulation session duty cycle). If T3 is 60 minutes and T4 is 1 day (24 hours, or 1440 minutes), then the duty cycle is 60/1440=0.042 (still, a very low session duty cycle, but approaching Applicant's session duty cycle limit of 0.05).

The amplitude of stimulation is adjustable and should be set to a comfortable level depending upon the particular patient. Ideally, the patient will feel or sense the stimulation as a slight tingling sensation at the acupoint location where the EA stimulation is applied. If the tingling sensation becomes uncomfortable, then the intensity (e.g., amplitude) of the EA stimulation pulses should be decreased until the sensation is comfortable. Typically, the amplitude of the stimulation pulses may be set to be as low as 1-2 mA and as high as 10-12 mA. The frequency of the EA stimulation pulses should be nominally 2 Hz, but could be as low as 1 Hz and as high as 3 Hz.

The width of the EA stimulation pulses should be about 0.5 millisecond, but could be as short as 0.1 millisecond (100 microseconds), or as long as 2 millisecond (2000 microseconds). The duty cycle of the applied EA stimulation pulses, T1/T2, during a stimulation session should be no more than 0.01, where T1 is the width of a stimulation pulse and T2 is the time period between the beginning of one stimulation pulse and the beginning of the next stimulation pulse. By way of example, if T1 is 0.5 millisecond, and T2 is 0.5 seconds (500 milliseconds, providing a rate of 2 Hz), then the duty cycle of the stimulus pulses during a stimulation session is 0.5/500=0.001 (a very, very low stimulus duty cycle).

Mechanical Design

Figure 1A:
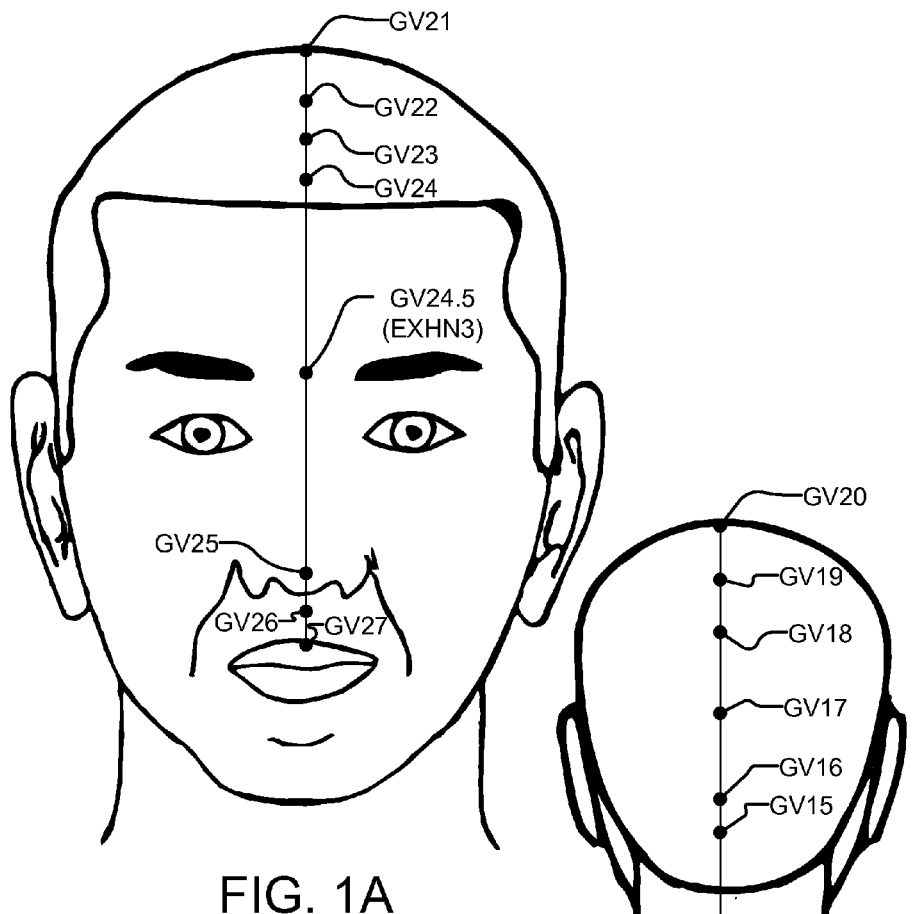
FIG. 1A illustrates the location of acupoint EXHN3 (also sometimes referred to as acupoint GV24.5, or acupoint EX Yintang), one of the two acupoints identified herein as a location to implant an IEAD for the treatment of depression, Anxiety or bipolar disorder.
Figure 1B:
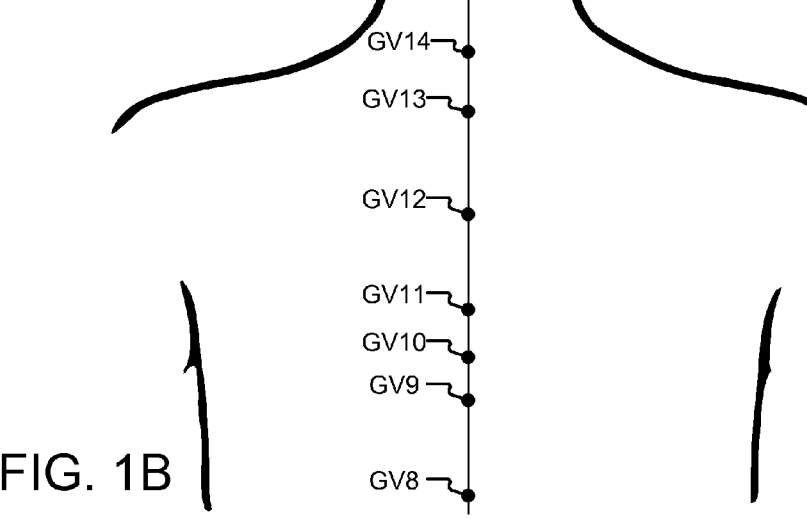
FIG. 1B depicts the location of acupoint GV20, the other of the two acupoints identified herein as a location to implant the IEAD for the treatment of depression, Anxiety or bipolar disorder.

Turning first to FIG. 1, there is shown a perspective view of one preferred embodiment of an implantable electroacupuncture device (IEAD) that may be used to treat depression, bipolar disorder or Anxiety in accordance with the teachings disclosed herein. The IEAD 100 may also sometimes be referred to as an implantable electroacupuncture stimulator (IEAS). As seen in FIG. 1, the preferred IEAD 100 has the appearance of a disc or coin, having a front side 102, a back side 106 (not visible in FIG. 1) and an edge side 104.

As used herein, the "front" side of the IEAD 100 is the side that is positioned so as to face the target stimulation point (e.g., the desired acupoint) where EA is to be applied when the IEAD is implanted. The "back" side is the side opposite the front side and is the farthest away from the target simulation point when the IEAD is implanted. The "edge" of the IEAD is the side that connects or joins the front side to the back side. In FIG. 1, the IEAD 100 is oriented to show the front side 102 and a portion of the edge side 104.

Many of the features associated with the mechanical design of the IEAD 100 shown in FIG. 1 are the subject of a prior U.S. Provisional Patent Application, entitled "Radial Feed-Through Packaging for An Implantable Electroacupuncture Device", Application No. 61/676,275, filed 26 Jul. 2012, which application is incorporated here by reference.

It should be noted that throughout this application, the terms IEAD 100, IEAD housing 100, bottom case 124, can 124, or IEAD case 124, or similar terms, are used to describe the housing structure of the EA device. In some instances, it may appear these terms are used interchangeably. However, the context should dictate what is meant by these terms. As the drawings illustrate, particularly FIG. 7, there is a bottom case 124 that comprises the "can" or "container" wherein the components of the IEAD 100 are first placed and assembled during manufacture of the IEAD 100. When all of the components are assembled and placed within the bottom case 124, a cover plate 122 is welded to the bottom case 124 to form the hermetically-sealed housing of the IEAD. The cathode electrode 110 is attached to the outside of the bottom case 124 (which is the front side 102 of the device), and the ring anode electrode 120 is attached, along with its insulating layer 129, around the perimeter edge 104 of the bottom case 124. Finally, a layer of silicone molding 125 covers the IEAD housing except for the outside surfaces of the anode ring electrode and the cathode electrode.

Figure 7:
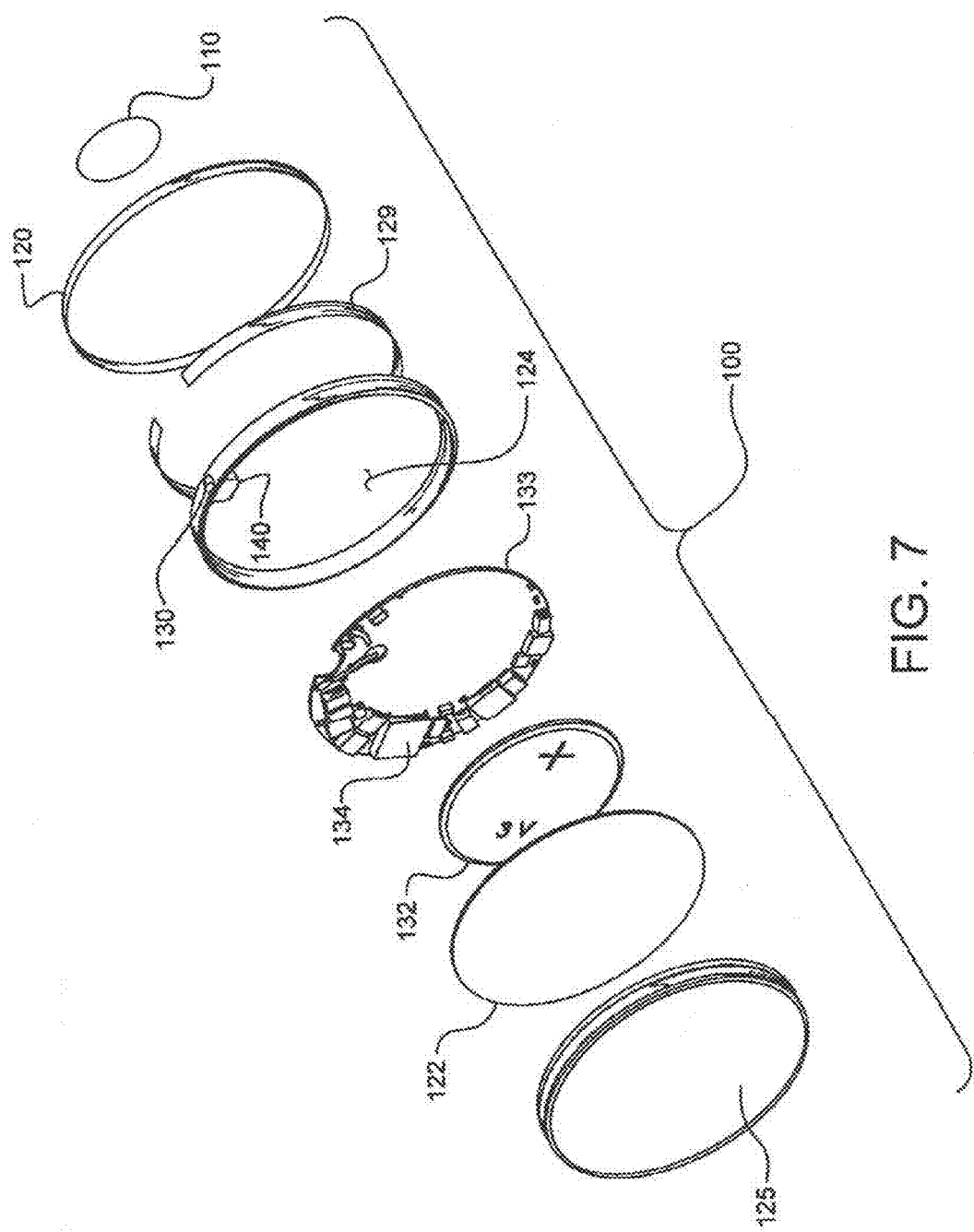
FIG. 7 is an exploded view of the IEAD assembly, illustrating its constituent parts.

The embodiment of the IEAD 100 shown in FIG. 1 utilizes two electrodes, a cathode electrode 110 that is centrally positioned on the front side 102 of the IEAD 100, and an anode electrode 120. The anode electrode 120 is a ring electrode that fits around the perimeter edge 104 of the IEAD 100. Not visible in FIG. 1, but which is described hereinafter in connection with the description of FIG. 7, is a layer of insulating material 129 that electrically insulates the anode ring electrode 120 from the perimeter edge 104 of the housing or case 124.

Not visible in FIG. 1, but a key feature of the mechanical design of the IEAD 100, is the manner in which an electrical connection is established between the ring electrode 120 and electronic circuitry carried inside of the IEAD 100. This electrical connection is established using a radial feed-through pin that fits within a recess formed in a segment of the edge of the case 124, as explained more fully below in connection with the description of FIGS. 5, 5A, 5B and 7.

In contrast to the feed-through pin that establishes electrical contact with the anode electrode, electrical connection with the cathode electrode 110 is established simply by forming or attaching the cathode electrode 110 to the front surface 102 of the IEAD case 124. This is because the case 124 is electrically connected to a reference potential of 0 volts, i.e., ground potential, on the inside of the IEAD case 124. In order to prevent the entire case 124 from functioning as the cathode (which is done to better control the electric fields established between the anode and cathode electrodes), the entire IEAD housing is covered in a layer of silicone molding 125 (see FIG. 7), except for the outside surface of the anode ring electrode 120 and the cathode electrode 110.

The advantage of using a central cathode electrode and a ring anode electrode is described in U.S. Provisional Patent Application No. 61/672,257, filed 6 Mar. 2012, entitled "Electrode Configuration for Implantable Electroacupuncture Device", which application is incorporated herein by reference. One significant advantage of this electrode configuration is that it is symmetrical. That is, when implanted, the surgeon or other medical personnel performing the implant procedure, need only assure that the cathode side of the IEAD 100, which (for the embodiment shown in FIGS. 1-7) is the front side of the device, facing the target tissue location that is to be stimulated.

In this regard, it should be noted that while the target stimulation point is generally identified by an "acupoint," which is typically shown in drawings and diagrams as residing on the surface of the skin, the surface of the skin is not the actual target stimulation point. Rather, whether such stimulation comprises manual manipulation of a needle inserted through the skin at the location on the skin surface identified as an "acupoint", or whether such stimulation comprises electrical stimulation applied through an electrical field oriented to cause stimulation current to flow through the tissue at a prescribed depth below the acupoint location on the skin surface, the actual target tissue point to be stimulated is located beneath the skin at a depth that varies depending on the particular acupoint location. When stimulation is applied at the target tissue point, such stimulation is effective at treating a selected condition of the patient, e.g., depression, because there is something in the tissue at that location, or near that location, such as a nerve, a tendon, a muscle, or other type of tissue, that responds to the applied stimulation in a manner that contributes favorably to the treatment of the condition experienced by the patient.

Figure 17A:
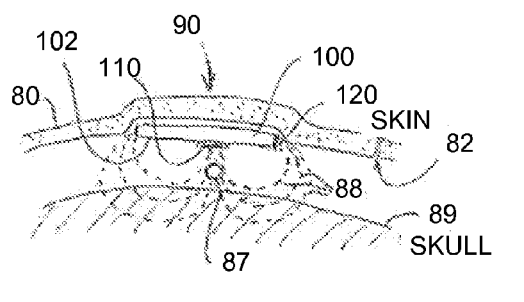
FIG. 17A illustrates one technique for implanting an IEAD under the skin in a location where a front surface of the IEAD faces inward toward the skull bone of the patient.
Figure 17B:
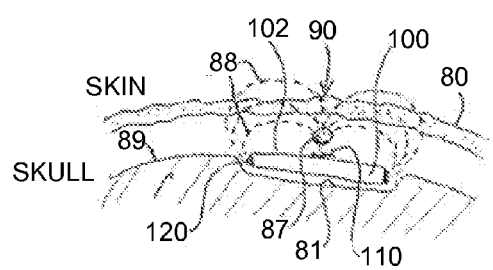
FIG. 17B depicts an alternative technique for implanting an IEAD in a pocket formed in the skull bone below a desired acupoint, with a front surface of the IEAD facing outward towards the skin.

For purposes of the present application, where the desired acupoints are located on the head of the patient, e.g., acupoints GV20 and/or EXHN3, see FIGS. 1A and 1B, the location of the patient's skull prevents deep tissue stimulation. This is illustrated schematically in FIGS. 17A and 17B. As seen in these figures, the skull 89 is generally right under the skin 80, with not much tissue separating the two. These two figures assume that the actual desired target stimulation point is a nerve 87 (or some other tissue formation) between the underneath side of the skin 80 and the top surface of the skull 89. Hence, the challenge is to implant the IEAD 100 in a manner that provides effective EA stimulation at the desired target stimulation site, e.g., at the nerve 87 (or other tissue formation) that resides beneath the acupoint 90. FIGS. 17A and 17B illustrate alternative methods for achieving this goal.

Shown in FIG. 17A is one alternative for implanting the IEAD 100 at an acupoint 90 located on the surface of the skin 80 above the skull 89, where the actual target stimulation point is a nerve 87, or some other tissue formation, that is located between the skull 89 and the underneath side of the skin 80. As shown in FIG. 17A, the IEAD 100 is implanted right under the skin with its front surface 102 facing down towards the target tissue location 87. This allows the electric fields (illustrated by the electric field gradient lines 88) generated by the IEAD 100 when EA stimulation pulses are to be generated to be most heavily concentrated at the target tissue stimulation site 87. These electric field gradient lines 88 are established between the two electrodes 110 and 120 of the IEAD. For the embodiment shown here, these two electrodes comprise a ring electrode 120, positioned around the perimeter edge of the IEAD housing, and a central electrode 110, positioned in the center of the front surface 102 of the IEAD housing. These gradient lines 88 are most concentrated right below the central electrode, which is where the target tissue location 87 resides. Hence, the magnitude of the electrical stimulation current will also be most concentrated at the target tissue location 87, which is the desired result.

FIG. 17B shows another alternative for implanting the IEAD 100 at the acupoint 90 located on the surface of the skin 80 above the skull 89, where the actual target stimulation point is a nerve 87, or some other tissue formation, that is located between the skull 89 and the underneath side of the skin 80. As shown in FIG. 17B, the IEAD 100 is implanted in a pocket 81 formed in the skull 89 at a location underneath the acupoint 90. In this instance, and as the elements are oriented in FIG. 17B, the front surface 102 of the IEAD 100 faces upwards towards the target tissue location 87. As with the implant configuration shown in FIG. 17A, this configuration also allows the electric fields (illustrated by the electric field gradient lines 88) that are generated by the IEAD 100 when EA stimulation pulses are generated to be most heavily concentrated at the target tissue stimulation site 87.

There are advantages and disadvantages associated with each of the two alternative implantation configurations shown in FIGS. 17A and 17B. Generally, the implantation procedure used to achieve the configuration shown in FIG. 17A is a simpler procedure with less risks. That is, all that need to be done by the surgeon to implant that EA device 100 as shown in FIG. 17A is to make an incision 82 in the skin 80 a short distance, e.g., 10-15 mm, away from the acupoint 90. This incision should be made parallel to the nerve 87 so as to minimize the risk of cutting the nerve 87. A slot is then formed at the incision by lifting the skin closest to the acupoint up at the incision and by carefully sliding the IEAD 100, with its front side 102 facing the skull, into the slot so that the center of the IEAD is located under the acupoint 90. Care is taken to assure that the nerve 87 resides below the front surface of the IEAD 100 as the IEAD is slid into position.

In contrast, if the implant configuration shown in FIG. 17B is to be used, then the implant procedure is somewhat more complicated with somewhat more risks. That is, to achieve the implant configuration shown in FIG. 17B, a sufficiently large incision must be made in the skin at the acupoint 90 to enable the skin 80 to be peeled or lifted away to expose the surface of the skull so that the cavity 81 may be formed in the skull bone. While doing this, care must be exercised to hold the nerve 87 (or other sensitive tissue areas) away from the cutting tools used to form the cavity 81. Once the cavity 81 is formed, the IEAD 100 is laid in the cavity, with its front surface facing upward, the nerve 87 (and other sensitive tissue areas) are carefully repositioned above the IEAD 100, and the skin is sewn or clamped to allow the incision to heal.

However, while the surgical procedure and attendant risks may be more complicated when the configuration of FIG. 17B is employed, the final results of the configuration of FIG. 17B may be more aesthetically pleasing to the patient than are achieved with the configuration of FIG. 17A. That is, given the shallow space between the skin and the skull at acupoints GV20 and EXHN3, the implant configuration of FIG. 17A will likely result in a small hump or bump at the implant site.

Insofar as Applicant is aware at the present time, of the two implant configurations shown in FIGS. 17A and 17B, there is no theoretical performance advantage that one implant configuration provides over the other. That is, both implant configurations should perform equally well insofar as providing EA stimulation pulses at the desired target tissue location 87 is concerned.

Thus, which implant configuration is used will, in large part, be dictated by individual differences in patient anatomy, patient preference, and surgeon preferences and skill levels.

From the above, it is seen that one of the main advantages of using a symmetrical electrode configuration that includes a centrally located electrode surrounded by an annular electrode, as is used in the embodiment described in connection with FIGS. 1-7, is that the precise orientation of the IEAD 100 within its implant location is not important. So long as one electrode faces and is centered over the desired target location, and the other electrode surrounds the first electrode (e.g., as an annular electrode), a strong electric field gradient is created that is aligned with the desired target tissue location. This causes the EA stimulation current to flow at (or very near to) the target tissue location 87.

FIG. 2 shows a plan view of the "front" side of the IEAD 100. As seen in FIG. 2, the cathode electrode 110 appears as a circular electrode, centered on the front side, having a diameter D1. The IEAD housing has a diameter D2 and an overall thickness or width W2. For the preferred embodiment shown in these figures, D1 is about 4 mm, D2 is about 23 mm and W2 is a little over 2 mm (2.2 mm).

FIG. 2A shows a side view of the IEAD 100. The ring anode electrode 120, best seen in FIG. 2A, has a width W1 of about 1.0 mm, or approximately ½ of the width W2 of the IEAD.

FIG. 3 shows a plan view of the "back" side of the IEAD 100. As will be evident from subsequent figure descriptions, e.g., FIGS. 5A and 5B, the back side of the IEAD 100 comprises a cover plate 122 that is welded in place once the case 124 has all of the electronic circuitry, and other components, placed inside of the housing.

FIG. 3A is a sectional view of the IEAD 100 of FIG. 1 taken along the line A-A of FIG. 3. Visible in this sectional view is the feed-through pin 130, including the distal end of the feed-through pin 130 attached to the ring anode electrode 120. Also visible in this section view is an electronic assembly 133 on which various electronic components are mounted, including a disc-shaped battery 132. FIG. 3A further illustrates how the cover plate 122 is welded, or otherwise bonded, to the case 124 in order to form the hermetically-sealed IEAD housing 100.

Figure 4:
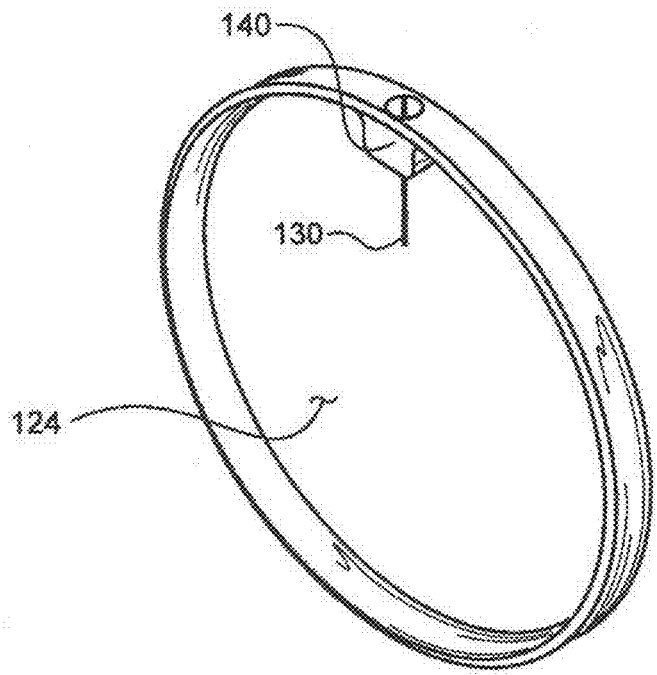
FIG. 4 is a perspective view of the IEAD housing, including a feed-through pin, before the electronic components are placed therein, and before being sealed with a cover plate.

FIG. 4 shows a perspective view of the IEAD case 124, including the feed-through pin 130, before the electronic components are placed therein, and before being sealed with the cover plate 122. The case 124 is similar to a shallow "can" without a lid, having a short side wall around its perimeter. Alternatively, the case 124 may be viewed as a short cylinder, closed at one end but open at the other. (Note, in the medical device industry the housing of an implanted device is often referred to as a "can".) The feed-through pin 130 passes through a segment of the wall of the case 124 that is at the bottom of a recess 140 formed in the wall. The use of this recess 140 to hold the feed-through pin 130 is a key feature of the invention because it keeps the temperature-sensitive portions of the feed-through assembly (those portions that could be damaged by excessive heat) away from the thermal shock and residual weld stress inflicted upon the case 124 when the cover plate 122 is welded thereto.

Figure 4A:
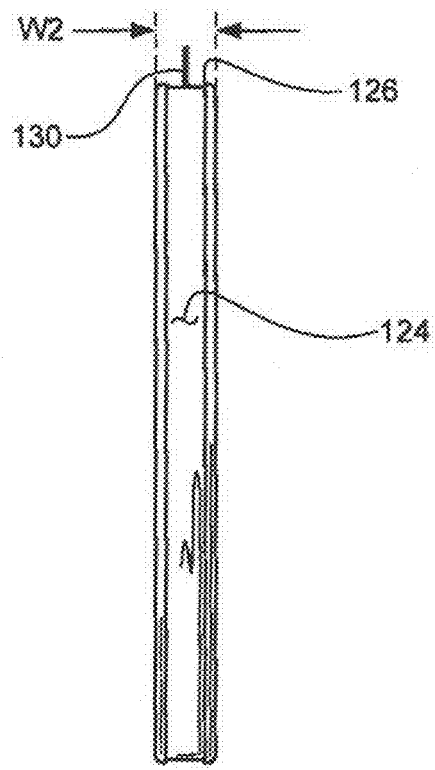
FIG. 4A is a side view of the IEAD housing of FIG. 4.

FIG. 4A is a side view of the IEAD case 124, and shows an annular rim 126 formed on both sides of the case 124. The ring electrode 120 fits between these rims 126 once the ring electrode 120 is positioned around the edge of the case 124. (This ring electrode 120 is, for most configurations, used as an anode electrode. Hence, the ring electrode 120 may sometimes be referred to herein as a ring anode electrode. However, it is noted that the ring electrode could also be employed as a cathode electrode, if desired.) A silicone insulator layer 129 (see FIG. 7) is placed between the backside of the ring electrode 120 and the perimeter edge of the case 124 where the ring electrode 120 is placed around the edge of the case 124.

Figures 5, 5A, 5B:
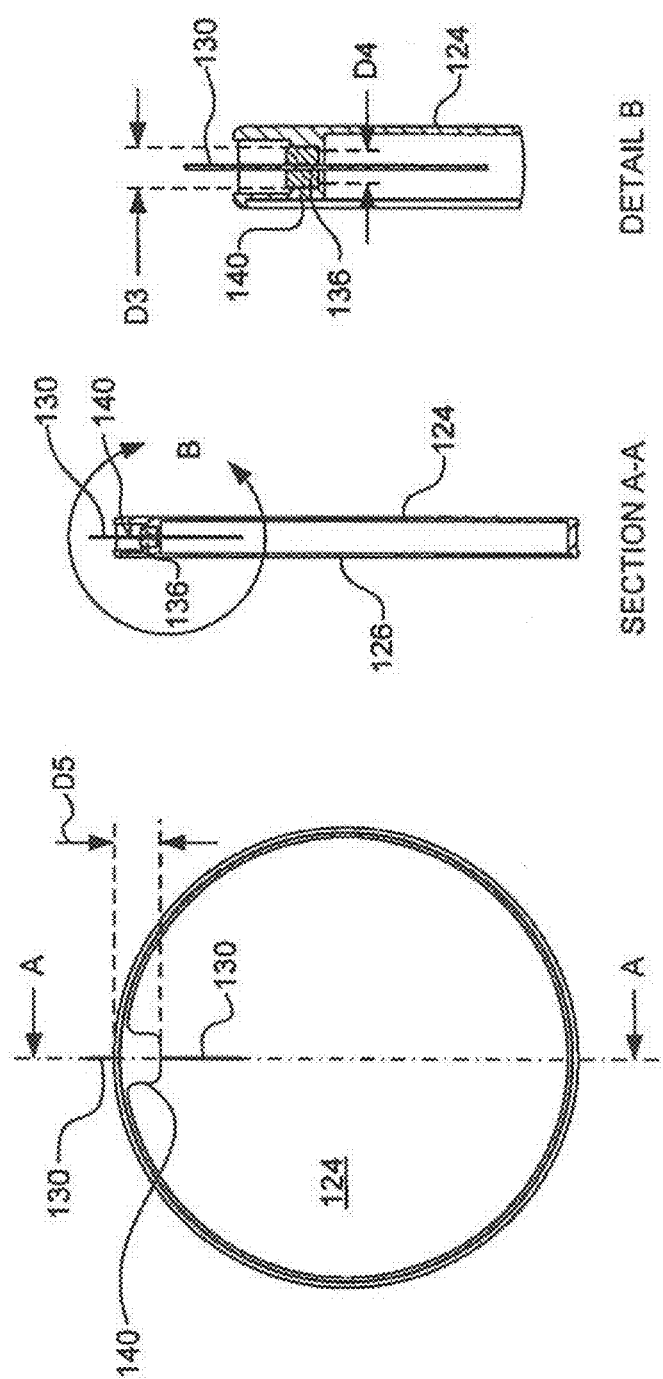
FIG. 5 is a plan view of the empty IEAD housing shown in FIG. 4.
FIG. 5A depicts a sectional view of the IEAD housing of FIG. 5 taken along the section line A-A of FIG. 5.
FIG. 5B shows an enlarged view or detail of the portion of FIG. 5A that is encircled with the line B.

FIG. 5 shows a plan view of the empty IEAD case 124 shown in the perspective view of FIG. 4. An outline of the recess cavity 140 is also seen in FIG. 5, as is the feed-through pin 130. A bottom edge of the recess cavity 140 is located a distance D5 radially inward from the edge of the case 124. In one embodiment, the distance D5 is between about 2.0 to 2.5 mm. The feed-through pin 130, which is just a piece of solid wire, is shown in FIG. 5 extending radially outward from the case 124 above the recess cavity 140 and radially inward from the recess cavity towards the center of the case 124. The length of this feed-through pin 130 is trimmed, as needed, when a distal end (extending above the recess) is connected (welded) to the anode ring electrode 120 (passing through a hole in the ring electrode 120 prior to welding) and when a proximal end of the feed-through pin 130 is connected to an output terminal of the electronic assembly 133.

FIG. 5A depicts a sectional view of the IEAD housing 124 of FIG. 5 taken along the section line A-A of FIG. 5. FIG. 5B shows an enlarged view or detail of the portion of FIG. 5A that is encircled with the line B. Referring to FIGS. 5A and 5B jointly, it is seen that the feed-through pin 130 is embedded within an insulator material 136, which insulating material 136 has a diameter of D3. The feed-through pin assembly (which pin assembly comprises the combination of the pin 130 embedded into the insulator material 136) resides on a shoulder around an opening or hole formed in the bottom of the recess 140 having a diameter D4. For the embodiment shown in FIGS. 5A and 5B, the diameter D3 is 0.95-0.07 mm, where the −0.07 mm is a tolerance. (Thus, with the tolerance considered, the diameter D3 may range from 0.88 mm to 0.95 mm) The diameter D4 is 0.80 mm with a tolerance of −0.06 mm. (Thus, with the tolerance considered, the diameter D4 could range from 0.74 mm to 0.80 mm).

The feed-through pin 130 is preferably made of pure platinum 99.95%. A preferred material for the insulator material 136 is Ruby or alumina. The IEAD case 124 and the cover 122 are preferably made from titanium. The feed-through assembly, including the feed-through pin 130, ruby/alumina insulator 136 and the case 124 are hermetically sealed as a unit by gold brazing. Alternatively, active metal brazing can be used. (Active metal brazing is a form of brazing which allows metal to be joined to ceramic without metallization.)

The hermeticity of the sealed IEAD housing is tested using a helium leak test, as is common in the medical device industry. The helium leak rate should not exceed $1 \times 10^{-9}$ STD cc/sec at 1 atm pressure. Other tests are performed to verify the case-to-pin resistance (which should be at least $15 \times 10^6$ Ohms at 100 volts DC), the avoidance of dielectric breakdown or flashover between the pin and the case 124 at 400 volts AC RMS at 60 Hz and thermal shock.

One important advantage provided by the feed-through assembly shown in FIGS. 4A, 5, 5A and 5B is that the feed-through assembly made from the feed-through pin 130, the ruby insulator 136 and the recess cavity 140 (formed in the case material 124) may be fabricated and assembled before any other components of the IEAD 100 are placed inside of the IEAD case 124. This advantage greatly facilitates the manufacture of the IEAD device.

Turning next to FIG. 6, there is shown a perspective view of an electronic assembly 133. The electronic assembly 133 includes a multi-layer printed circuit (pc) board 138, or equivalent mounting structure, on which a battery 132 and various electronic components 134 are mounted. This assembly is adapted to fit inside of the empty housing 124 of FIG. 4 and FIG. 5.

FIGS. 6A and 6B show a plan view and side view, respectively, of the electronic assembly 133 shown in FIG. 6. The electronic components are assembled and connected together so as to perform the circuit functions needed for the IEAD 100 to perform its intended functions. These circuit functions are explained in more detail below under the sub-heading "Electrical Design". Additional details associated with these functions may also be found in many of the co-pending patent applications referenced above in Paragraph [0001].

FIG. 7 shows an exploded view of the complete IEAD 100, illustrating its main constituent parts. As seen in FIG. 7, the IEAD 100 includes, starting on the right and going left, a cathode electrode 110, a ring anode electrode 120, an insulating layer 129, the bottom case 124 (the "can" portion of the IEAD housing, and which includes the feed-through pin 130 which passes through an opening in the bottom of the recess 140 formed as part of the case, but wherein the feed-through pin 130 is insulated and does not make electrical contact with the metal case 124 by the ruby insulator 136), the electronic assembly 133 (which includes the battery 132 and various electronic components 134 mounted on a pc board 138) and the cover plate 122. The cover plate 122 is welded to the edge of the case 124 using laser beam welding, or some equivalent process, as one of the final steps in the assembly process.

Other components included in the IEAD assembly, but not necessarily shown or identified in FIG. 7, include adhesive patches for bonding the battery 132 to the pc board 138 of the electronic assembly 133, and for bonding the electronic assembly 133 to the inside of the bottom of the case 124. To prevent high temperature exposure of the battery 132 during the assembly process, conductive epoxy is used to connect a battery terminal to the pc board 138. Because the curing temperature of conductive epoxy is 125° C., the following process is used: (a) first cure the conductive epoxy of a battery terminal ribbon to the pc board without the battery, (b) then glue the battery to the pc board using room temperature cure silicone, and (c) laser tack weld the connecting ribbon to the battery.

Also not shown in FIG. 7 is the manner of connecting the proximal end of the feed-through pin 130 to the pc board 138, and connecting a pc board ground pad to the case 124. A preferred method of making these connections is to use conductive epoxy and conductive ribbons, although other connection methods known in the art may also be used.

Further shown in FIG. 7 is a layer of silicon molding 125 that is used to cover all surfaces of the entire IEAD 100 except for the ring electrode 120 and the circular electrode 110. An overmodling process is used to accomplish this, although overmolding using silicone LSR 70 (curing temperature of 120° C.) with an injection moldling process cannot be used. Overmolding processes that may be used include: (a) molding a silicone jacket and gluing the jacket onto the case using room temperature cure silicone (RTV) inside of a mold, and curing at room temperature; (b) injecting room temperature cure silicone in a PEEK or Teflon® mold (silicone will not stick to the Teflon® or PEEK material); or (c) dip coating the IEAD 100 in room temperature cure silicone while masking the electrode surfaces that are not to be coated. (Note: PEEK is a well known semicrystalline thermoplastic with excellent mechanical and chemical resistance properties that are retained at high temperatures.)

When assembled, the insulating layer 129 is positioned underneath the ring anode electrode 120 so that the anode electrode does not short to the case 124. The only electrical connection made to the anode electrode 120 is through the distal tip of the feed-through pin 130. The electrical contact with the cathode electrode 110 is made through the case 124. However, because the entire IEAD is coated with a layer of silicone molding 125, except for the anode ring electrode 120 and the circular cathode electrode 110, all stimulation current generated by the IEAD 100 must flow between the exposed surfaces of the anode and cathode.

It is noted that while the preferred configuration described herein uses a ring anode electrode 120 placed around the edges of the IEAD housing, and a circular cathode electrode 110 placed in the center of the cathode side of the IEAD case 124, such an arrangement could be reversed, i.e., the ring electrode could be the cathode, and the circular electrode could be the anode.

Moreover, the location and shape of the electrodes may be configured differently than is shown in the one preferred embodiment described above in connection with FIGS. 1-7. For example, the ring anode electrode 120 need not be placed around the perimeter of the device, but such electrode may be a flat circumferential electrode that assumes different shapes (e.g., round or oval) that is placed on the front or back surface of the IEAD so as to surround the central electrode. Further, for some embodiments, the surfaces of the anode and cathode electrodes may have convex surfaces.

It is also noted that while one preferred embodiment has been disclosed herein that incorporates a round, or short cylindrical-shaped housing, also referred to as a coin-shaped housing, the invention does not require that the case 124 (which may also be referred to as a "container"), and its associated cover plate 122, be round. The case could just as easily be an oval-shaped, rectangular-shaped (e.g., square with smooth corners), polygonal-shaped (e.g., hexagon-, octagon-, pentagon-shaped), button-shaped (with convex top or bottom for a smoother profile) device. Any of these alternate shapes, or others, would still permit the basic principles of the invention to be used to help protect a feed-through assembly from being exposed to excessive heat during assembly, and to allow the thin device to provide the benefits described herein related to its manufacture, implantation and use. For example, as long as the device remains relatively thin, e.g., no more than about 2-3 mm, and does not have a maximum linear dimension greater than about 25 mm, then the device can be readily implanted in a pocket over the tissue area where the selected acupuoint(s) is located. As long as there is a recess in the wall around the perimeter of the case wherein the feed-through assembly may be mounted, which recess effectively moves the wall or edge of the case inwardly into the housing a safe thermal distance, as well as a safe residual weld stress distance, from the perimeter wall where a hermetically-sealed weld occurs, the principles of the invention apply.

Further, it should be noted that while the preferred configuration of the IEAD described herein utilizes a central electrode on one of its surfaces that is round, having a diameter of nominally 4 mm, such central electrode need not necessarily be round. It could be oval shaped, polygonal-shaped, or shaped otherwise, in which case its size is best defined by its maximum width, which will generally be no greater than about 7 mm.

Finally, it is noted that the electrode arrangement may be modified somewhat, and the desired attributes of the invention may still be achieved. For example, as indicated previously, one preferred electrode configuration for use with the invention utilizes a symmetrical electrode configuration, e.g., an annular electrode of a first polarity that surrounds a central electrode of a second polarity. Such a symmetrical electrode configuration makes the implantable electroacupuncture device (IEAD) relatively immune to being implanted in an improper orientation relative to the body tissue at the selected acupoint(s) that is being stimulated. However, an electrode configuration that is not symmetrical may still be used and many of the therapeutic effects of the invention may still be achieved. For example, two spaced-apart electrodes on a front surface of the housing, one of a first polarity, and a second of a second polarity, could still, when oriented properly with respect to a selected acupoint tissue location, provide some desired therapeutic results FIG. 7A schematically illustrates a few alternative electrode configurations that may be used with the invention. The electrode configuration schematically shown in the upper left corner of FIG. 7A, identified as "I", schematically illustrates one central electrode 110 surrounded by a single ring electrode 120. This is one of the preferred electrode configurations that has been described previously in connection, e.g., with the description of FIGS. 1-7, and is presented in FIG. 7A for reference and comparative purposes.

In the lower left corner of FIG. 7A, identified as "II", an electrode/array configuration is schematically illustrated that has a central electrode 310 of a first polarity surrounded by an electrode array 320a of two electrodes of a second polarity. When the two electrodes (of the same polarity) in the electrode array 320a are properly aligned with the body tissue being stimulated, e.g., aligned with a nerve 87 (see FIGS. 17A and 17B), then such electrode configuration can stimulate the body tissue (e.g., the nerve 87) at or near the desired acupoint(s) with the same, or almost the same, efficacy as can the electrode configuration I (upper right corner of FIG. 7A).

Note, as has already been described above, the phrase "electrode or electrode array," or "electrodes or electrode arrays," may also be referred to herein as "electrode/array" or "electrodes/arrays," respectively. For the ease of explanation, when an electrode array is referred to herein that comprises a plurality (two or more) of individual electrodes of the same polarity, the individual electrodes of the same polarity within the electrode array may also be referred to as "individual electrodes", "segments" of the electrode array, "electrode segments", or just "segments".

In the lower right corner of FIG. 7A, identified as "III", en electrode configuration is schematically illustrated that has a central electrode/array 310b of three electrode segments of a first polarity surrounded by an electrode array 320b of three electrode segments of a second polarity. As shown in FIG. 7A-III, the three electrode segments of the electrode array 320b are symmetrically positioned within the array 320b, meaning that they are positioned more or less equidistant from each other. However, a symmetrical positioning of the electrode segments within the array is not necessary to stimulate the body tissue at the desired acupoint(s) with some efficacy.

In the upper right corner of FIG. 7A, identified as "IV", an electrode/array configuration is schematically illustrated that has a central electrode array 310c of a first polarity surrounded by an electrode array 320c of four electrode segments of a second polarity. The four electrode segments of the electrode array 320c are arranged in a round or oval-shaped array. The four electrode segments of the electrode array 310b are likewise arranged in a round or oval-shaped array. While preferred for many configurations, the use of a symmetrical electrode/array, whether as a central electrode array 310 or as a surrounding electrode/array 320, is not required in all configurations.

The electrode configurations I, II, III and IV shown schematically in FIG. 7A are only representative of a few electrode configurations that may be used with the present invention. Further, it is to be noted that the central electrode/array 310 need not have the same number of electrode segments as does the surrounding electrode/array 320. Typically, the central electrode/array 310 of a first polarity will be a single electrode; whereas the surrounding electrode/array 320 of a second polarity may have n individual electrode segments, where n is an integer that can vary from 1, 2, 3, ... n. Thus, for a circumferential electrode array where n=4, there are four electrode segments of the same polarity arranged in circumferential pattern around a central electrode/array. If the circumferential electrode array with n=4 is a symmetrical electrode array, then the four electrode segments will be spaced apart equally in a circumferential pattern around a central electrode/array. When n=1, the circumferential electrode array reduces to a single circumferential segment or a single annular electrode that surrounds a central electrode/array.

Additionally, the polarities of the electrode/arrays may be selected as needed. That is, while the central electrode/array 310 is typically a cathode (−), and the surrounding electrode/array 320 is typically an anode (+), these polarities may be reversed.

It should be noted that the shape of the circumferential electrode/array, whether circular, oval, or other shape, need not necessarily be the same shape as the IEAD housing, unless the circumferential electrode/array is attached to a perimeter edge of the IEAD housing. The IEAD housing may be round, or it may be oval, or it may have a polygon shape, or other shape, as needed to suit the needs of a particular manufacturer and/or patient.

Additional electrode configurations, both symmetrical electrode configurations and non-symmetrical electrode configurations, that may be used with an EA stimulation device as described herein, are described in Appendices A and B.

Electrical Design

Next, with reference to FIGS. 8A-14, the electrical design and operation of the circuits employed within the IEAD 100 will be described. More details associated with the design of the electrical circuits described herein may be found in the following previously-filed U.S. Provisional Patent Applications, which applications are incorporated herein by reference: (1) Appl. No. 61/575,869, filed Aug. 30, 2012, entitled Implantable Electroacupuncture Device and Method For Reducing Hypertension; (2) Appl. No. 61/609,875, filed Mar. 12, 2012, entitled Boost Converter Output Control For Implantable Electroacupuncture Device; (3) Appl. No. 61/672,257, filed Jul. 16, 2012, entitled Boost Converter Circuit Surge Control For Implantable Electroacupuncture Device Using Digital Pulsed Shutdown; (4) Appl. No. 61/672,661, filed Jul. 17, 2012, entitled Smooth Ramp-Up Stimulus Amplitude Control For Implantable Electroacupuncture Device; and (5) Appl. No. 61/674,691, filed Jul. 23, 2012, entitled Pulse Charge Delivery Control In An Implantable Electroacupuncture Device.

Figure 8A:
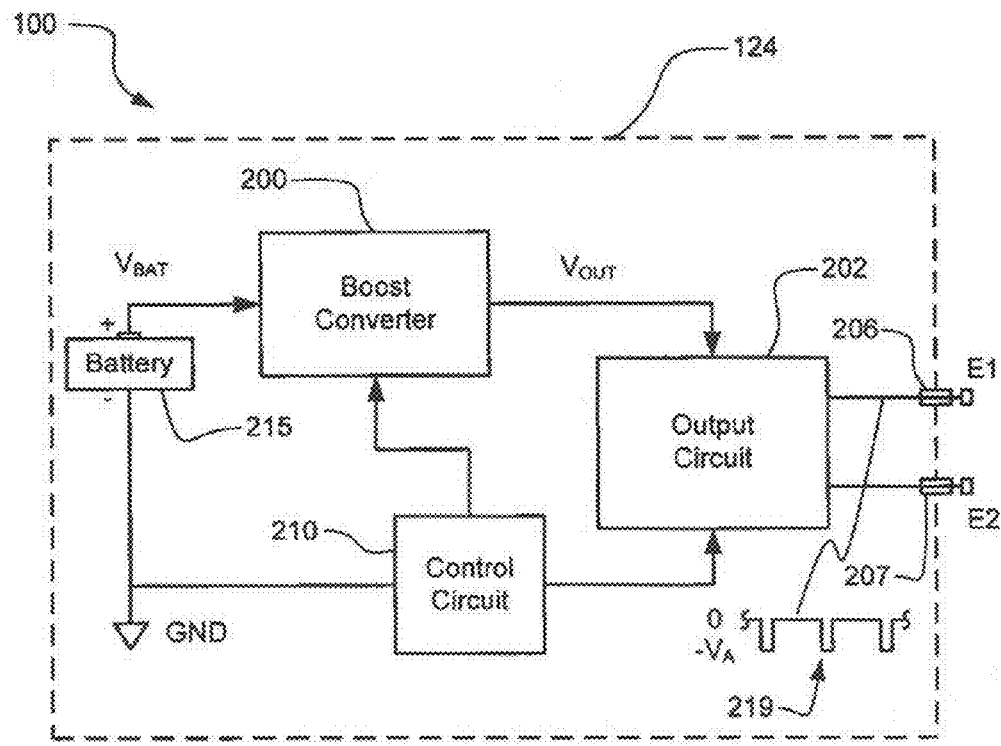
FIG. 8A illustrates a functional block diagram of the electronic circuits used within an IEAD of the type described herein.

FIG. 8A shows a functional block diagram of an implantable electroacupuncture device (IEAD) 100 made in accordance with the teachings disclosed herein. As seen in FIG. 8A, the IEAD 100 uses an implantable battery 215 having a battery voltage $V_{BAT}$. Also included within the IEAD 100 is a Boost Converter circuit 200, an Output Circuit 202 and a Control Circuit 210. The battery 115, boost converter circuit 200, output circuit 202 and control circuit 210 are all housed within an hermetically sealed housing 124.

As controlled by the control circuit 210, the output circuit 202 of the IEAD 100 generates a sequence of stimulation pulses that are delivered to electrodes E1 and E2, through feed-through terminals 206 and 207, respectively, in accordance with a prescribed stimulation regimen. A coupling capacitor $C_C$ is also employed in series with at least one of the feed-through terminals 206 or 207 to prevent DC (direct current) current from flowing into the patient's body tissue.

Figure 15A:
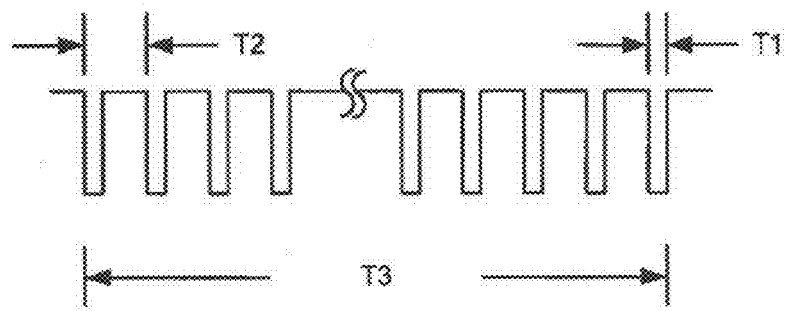
FIG. 15A shows a timing waveform diagram of representative EA stimulation pulses generated by the IEAD device during a stimulation session.

As explained more fully below in connection with the description of FIGS. 15A and 15B, the prescribed stimulation regimen comprises a continuous stream of stimulation pulses having a fixed amplitude, e.g., $V_A$ volts, a fixed pulse width, e.g., 0.5 millisecond, and at a fixed frequency, e.g., 2 Hz, during each stimulation session. The stimulation session, also as part of the stimulation regimen, is generated at a very low duty cycle, e.g., for 30 minutes once each week.

In one preferred embodiment, the electrodes E1 and E2 form an integral part of the housing 124. That is, electrode E2 may comprise a circumferential anode electrode that surrounds a cathode electrode E1. The cathode electrode E1, for the embodiment described here, is electrically connected to the case 124 (thereby making the feed-through terminal 206 unnecessary).

In a second preferred embodiment, particularly well-suited for implantable electrical stimulation devices, the anode electrode E2 is electrically connected to the case 124 (thereby making the feed-through terminal 207 unnecessary). The cathode electrode E1 is electrically connected to the circumferential electrode that surrounds the anode electrode E2. That is, the stimulation pulses delivered to the target tissue location (i.e., to the selected acupoint) through the electrodes E1 and E2 are, relative to a zero volt ground (GND) reference, negative stimulation pulses, as shown in the waveform diagram near the lower right hand corner of FIG. 8A.

Thus, in the embodiment described in FIG. 8A, it is seen that during a stimulation pulse the electrode E2 functions as an anode, or positive (+) electrode, and the electrode E1 functions as a cathode, or negative (−) electrode.

The battery 115 provides all of the operating power needed by the EA device 100. The battery voltage $V_{BAT}$ is not the optimum voltage needed by the circuits of the EA device, including the output circuitry, in order to efficiently generate stimulation pulses of amplitude, e.g., $-V_A$ volts. The amplitude $V_A$ of the stimulation pulses is typically many times greater than the battery voltage $V_{BAT}$. This means that the battery voltage must be "boosted", or increased, in order for stimulation pulses of amplitude $V_A$ to be generated. Such "boosting" is done using the boost converter circuit 200. That is, it is the function of the Boost Converter circuit 200 to take its input voltage, $V_{BAT}$, and convert it to another voltage, e.g., $V_{OUT}$, which voltage $V_{OUT}$ is needed by the output circuit 202 in order for the IEAD 100 to perform its intended function.

The IEAD 100 shown in FIG. 8A, and packaged as described above in connection with FIGS. 1-7, advantageously provides a tiny self-contained, coin-sized stimulator that may be implanted in a patient at or near a specified acupoint in order to favorably treat a condition or disease of a patient. The coin-sized stimulator advantageously applies electrical stimulation pulses at very low levels and duty cycles in accordance with specified stimulation regimens through electrodes that form an integral part of the housing of the stimulator. A tiny battery inside of the coin-sized stimulator provides enough energy for the stimulator to carry out its specified stimulation regimen over a period of several years. Thus, the coin-sized stimulator, once implanted, provides an unobtrusive, needleless, long-lasting, safe, elegant and effective mechanism for treating certain conditions and diseases that have long been treated by acupuncture or electroacupuncture.

Figure 8B:
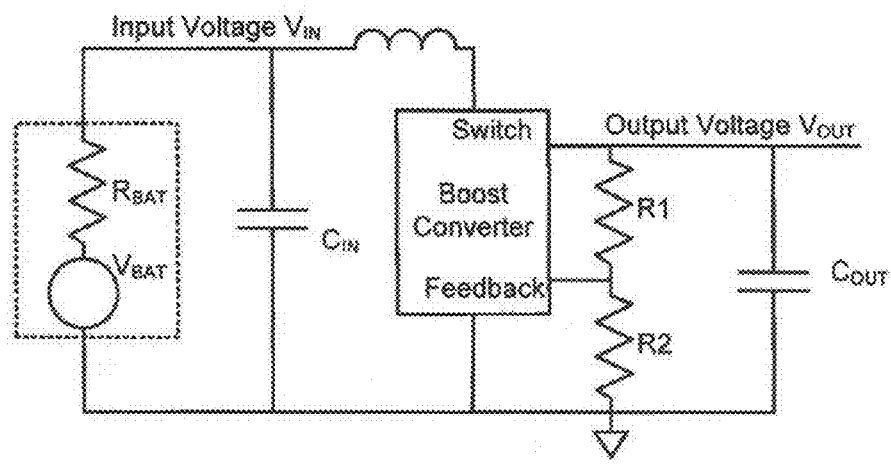
FIG. 8B shows a basic boost converter circuit configuration, and is used to model how the impedance of the battery $R_{BAT}$ can affect its performance.

A boost converter integrated circuit (IC) typically draws current from its power source in a manner that is proportional to the difference between the actual output voltage $V_{OUT}$ and a set point output voltage, or feedback signal. A representative boost converter circuit that operates in this manner is shown in FIG. 8B. At boost converter start up, when the actual output voltage is low compared to the set point output voltage, the current drawn from the power source can be quite large. Unfortunately, when batteries are used as power sources, they have internal voltage losses (caused by the battery's internal impedance) that are proportional to the current drawn from them. This can result in under voltage conditions when there is a large current demand from the boost converter at start up or at high instantaneous output current. Current surges and the associated under voltage conditions can lead to undesired behavior and reduced operating life of an implanted electroacupuncture device.

In the boost converter circuit example shown in FIG. 8A, the battery is modeled as a voltage source with a simple series resistance. With reference to the circuit shown in FIG. 8A, when the series resistance $R_{BAT}$ is small (5 Ohms or less), the boost converter input voltage $V_{IN}$, output voltage $V_{OUT}$ and current drawn from the battery, $I_{BAT}$, typically look like the waveform shown in FIG. 9A, where the horizontal axis is time, and the vertical axis on the left is voltage, and the vertical axis of the right is current.

Figure 9A:
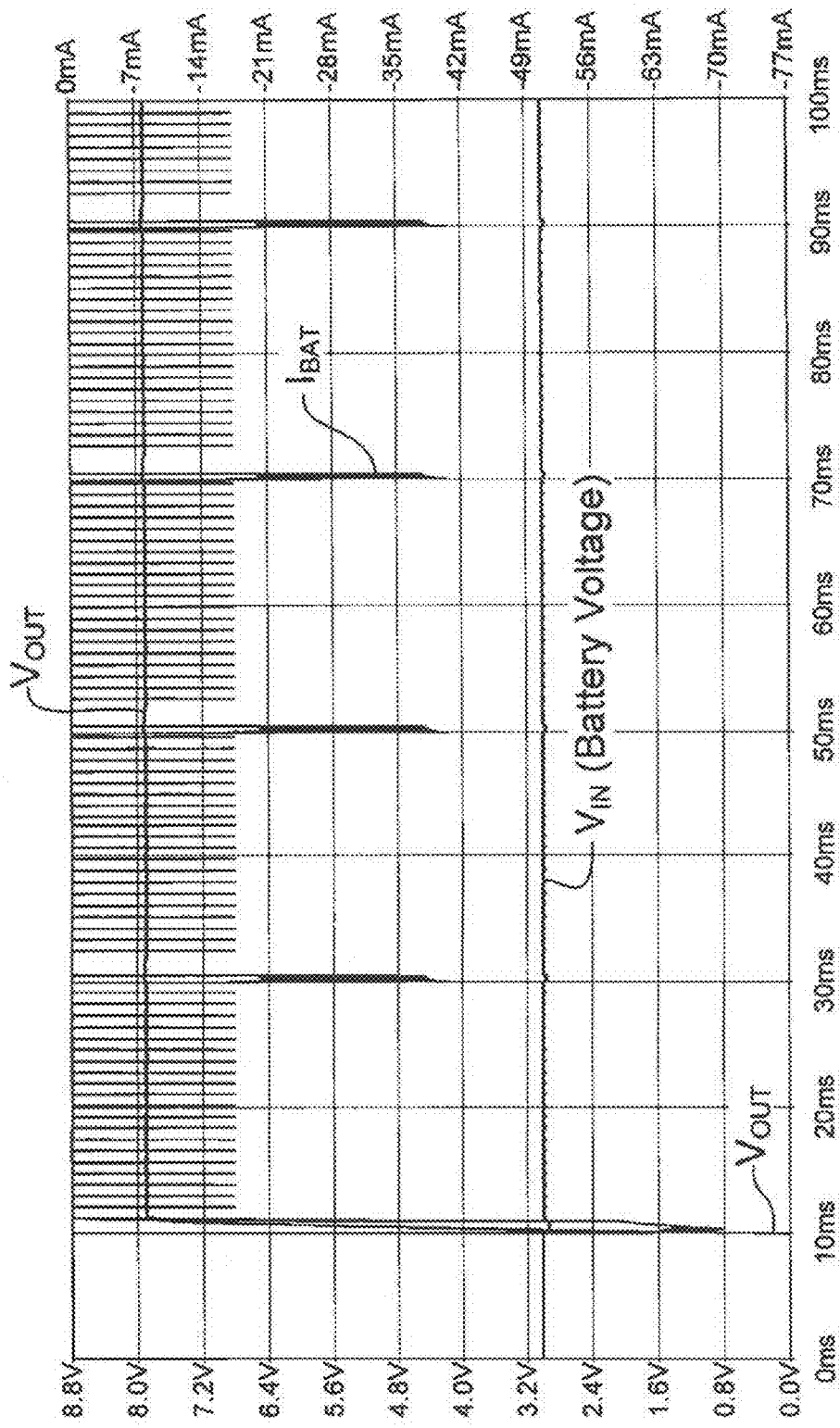
FIG. 9A illustrates a typical voltage and current waveform for the circuit of FIG. 8 when the battery impedance $R_{BAT}$ is small.

Referring to the waveform in FIG. 9A, at boost converter startup (10 ms), there is 70 mA of current drawn from the battery with only ~70 mV of drop in the input voltage $V_{IN}$. Similarly, the instantaneous output current demand for electro-acupuncture pulses draws up to 40 mA from the battery with an input voltage drop of ~40 mV.

Figure 9B:
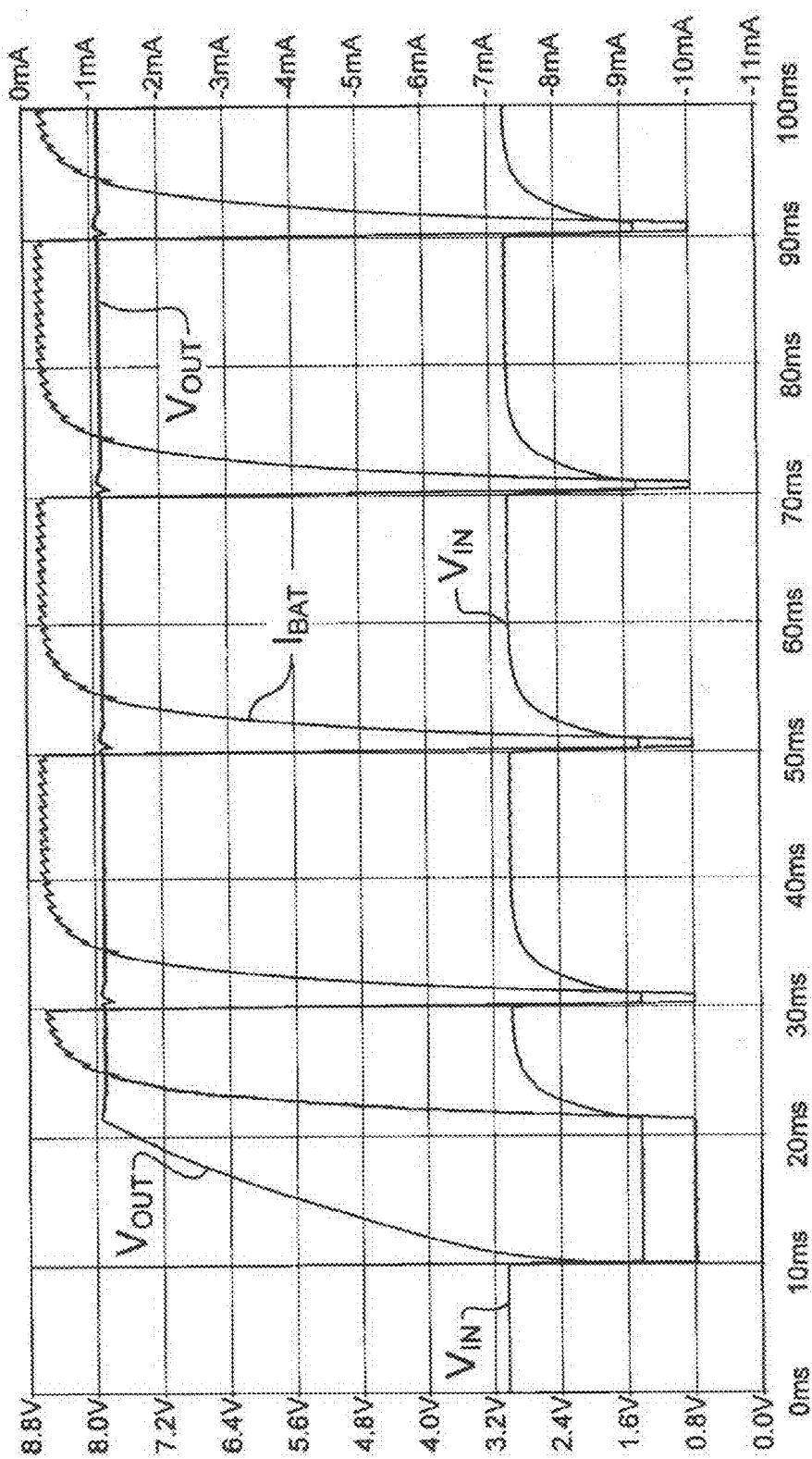
FIG. 9B shows the voltage and current waveform for the circuit of FIG. 8B when the battery impedance $R_{BAT}$ is large.

Disadvantageously, however, a battery with higher internal impedance (e.g., 160 Ohms), cannot source more than a milliampere or so of current without a significant drop in output voltage. This problem is depicted in the timing waveform diagram shown in FIG. 9B. In FIG. 9B, as in FIG. 9A, the horizontal axis is time, the left vertical axis is voltage, and the right vertical axis is current.

As seen in FIG. 9B, as a result of the higher internal battery impedance, the voltage at the battery terminal ($V_{IN}$) is pulled down from 2.9 V to the minimum input voltage of the boost converter (~1.5 V) during startup and during the instantaneous output current load associated with electro-acupuncture stimulus pulses. The resulting drops in output voltage $V_{OUT}$ are just not acceptable in any type of circuit except an uncontrolled oscillator circuit.

Also, it should be noted that although the battery used in the boost converter circuit is modeled in FIG. 8B as a simple series resistor, battery impedance can arise from the internal design, battery electrode surface area and different types of electrochemical reactions. All of these contributors to battery impedance can cause the voltage of the battery at the battery terminals to decrease as the current drawn from the battery increases.

In a suitably small and thin implantable electroacupuncture device (IEAD) of the type disclosed herein, it is desired to use a higher impedance battery in order to assure a small and thin device, keep costs low, and/or to have low self-discharge rates. The battery internal impedance also typically increases as the battery discharges. This can limit the service life of the device even if a new battery has acceptably low internal impedance. Thus, it is seen that for the IEAD 100 disclosed herein to reliably perform its intended function over a long period of time, a circuit design is needed for the boost converter circuit that can manage the instantaneous current drawn from $V_{IN}$ of the battery. Such current management is needed to prevent the battery's internal impedance from causing $V_{IN}$ to drop to unacceptably low levels as the boost converter circuit pumps up the output voltage $V_{OUT}$ and when there is high instantaneous output current demand, as occurs when EA stimulation pulses are generated.

Figure 10:
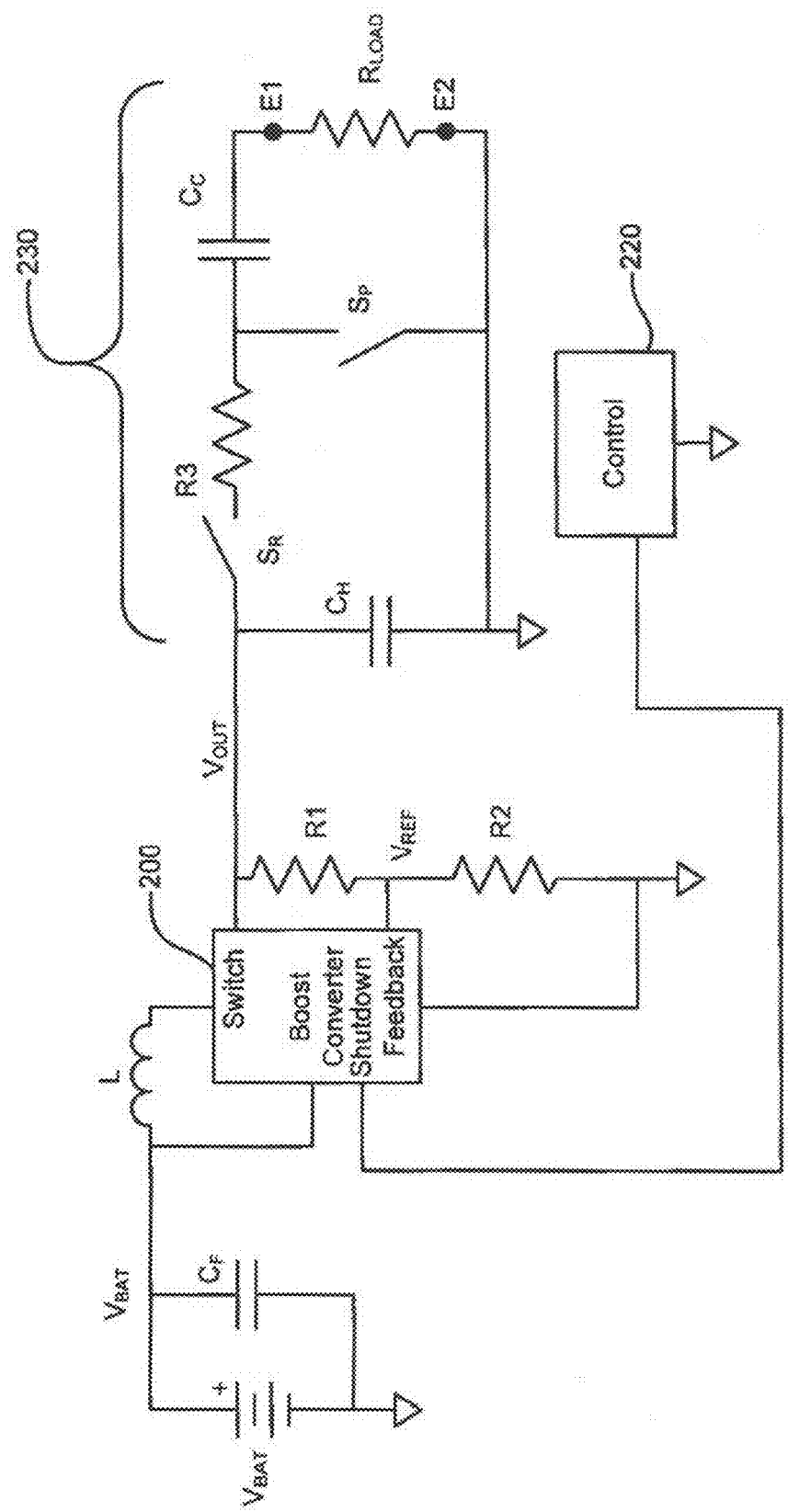
FIG. 10 shows one preferred boost converter circuit and a functional pulse generation circuit configuration for use within the IEAD.

To provide this needed current management, the IEAD 100 disclosed herein employs electronic circuitry as shown in FIG. 10, or equivalents thereof. Similar to what is shown in FIG. 8B, the circuitry of FIG. 10 includes a battery, a boost converter circuit 200, an output circuit 230, and a control circuit 220. The control circuit 220 generates a digital control signal that is used to duty cycle the boost converter circuit 200ON and OFF in order to limit the instantaneous current drawn from the battery. That is, the digital control signal pulses the boost converter ON for a short time, but then shuts the boost converter down before a significant current can be drawn from the battery. In conjunction with such pulsing, an input capacitance $C_F$ is used to reduce the ripple in the input voltage $V_{IN}$. The capacitor $C_F$ supplies the high instantaneous current for the short time that the boost converter is ON and then recharges more slowly from the battery during the interval that the boost converter is OFF.

In the circuitry shown in FIG. 10, it is noted that the output voltage $V_{OUT}$ generated by the boost converter circuit 200 is set by the reference voltage $V_{REF}$ applied to the set point or feedback terminal of the boost converter circuit 200. For the configuration shown in FIG. 10, $V_{REF}$ is proportional to the output voltage $V_{OUT}$, as determined by the resistor dividing network of R1 and R2.

The switches $S_P$ and $S_R$, shown in FIG. 10 as part of the output circuit 230, are also controlled by the control circuit 220. These switches are selectively closed and opened to form the EA stimulation pulses applied to the load, $R_{LOAD}$. Before a stimulus pulse occurs, switch $S_R$ is closed sufficiently long for the circuit side of coupling capacitor $C_C$ to be charged to the output voltage, $V_{OUT}$. The tissue side of $C_C$ is maintained at 0 volts by the cathode electrode E2, which is maintained at ground reference. Then, for most of the time between stimulation pulses, both switches $S_R$ and $S_P$ are kept open, with a voltage approximately equal to the output voltage $V_{OUT}$ appearing across the coupling capacitor $C_C$.

At the leading edge of a stimulus pulse, the switch $S_P$ is closed, which immediately causes a negative voltage $-V_{OUT}$ to appear across the load, $R_{LOAD}$, causing the voltage at the anode E1 to also drop to approximately $-V_{OUT}$, thereby creating the leading edge of the stimulus pulse. This voltage starts to decay back to 0 volts as controlled by an RC (resistor-capacitance) time constant that is long compared with the desired pulse width. At the trailing edge of the pulse, before the voltage at the anode E1 has decayed very much, the switch $S_F$ is open and the switch $S_R$ is closed. This action causes the voltage at the anode E1 to immediately (relatively speaking) return to 0 volts, thereby defining the trailing edge of the pulse. With the switch $S_R$ closed, the charge on the circuit side of the coupling capacitor $C_C$ is allowed to charge back to $V_{OUT}$ within a time period controlled by a time constant set by the values of capacitor $C_C$ and resistor R3. When the circuit side of the coupling capacitor $C_C$ has been charged back to $V_{OUT}$, then switch $S_R$ is opened, and both switches $S_R$ and $S_F$ remain open until the next stimulus pulse is to be generated. Then the process repeats each time a stimulus pulse is to be applied across the load.

Thus, it is seen that in one embodiment of the electronic circuitry used within the IEAD 100, as shown in FIG. 10, a boost converter circuit 200 is employed which can be shut down with a control signal. The control signal is ideally a digital control signal generated by a control circuit 220 (which may be realized using a microprocessor or equivalent circuit). The control signal is applied to the low side (ground side) of the boost converter circuit 200 (identified as the "shutdown" terminal in FIG. 10). A capacitor $C_F$ supplies instantaneous current for the short ON time that the control signal enables the boost converter circuit to operate. And, the capacitor CF is recharged from the battery during the relatively long OFF time when the control signal disables the boost converter circuit.

Figure 11:
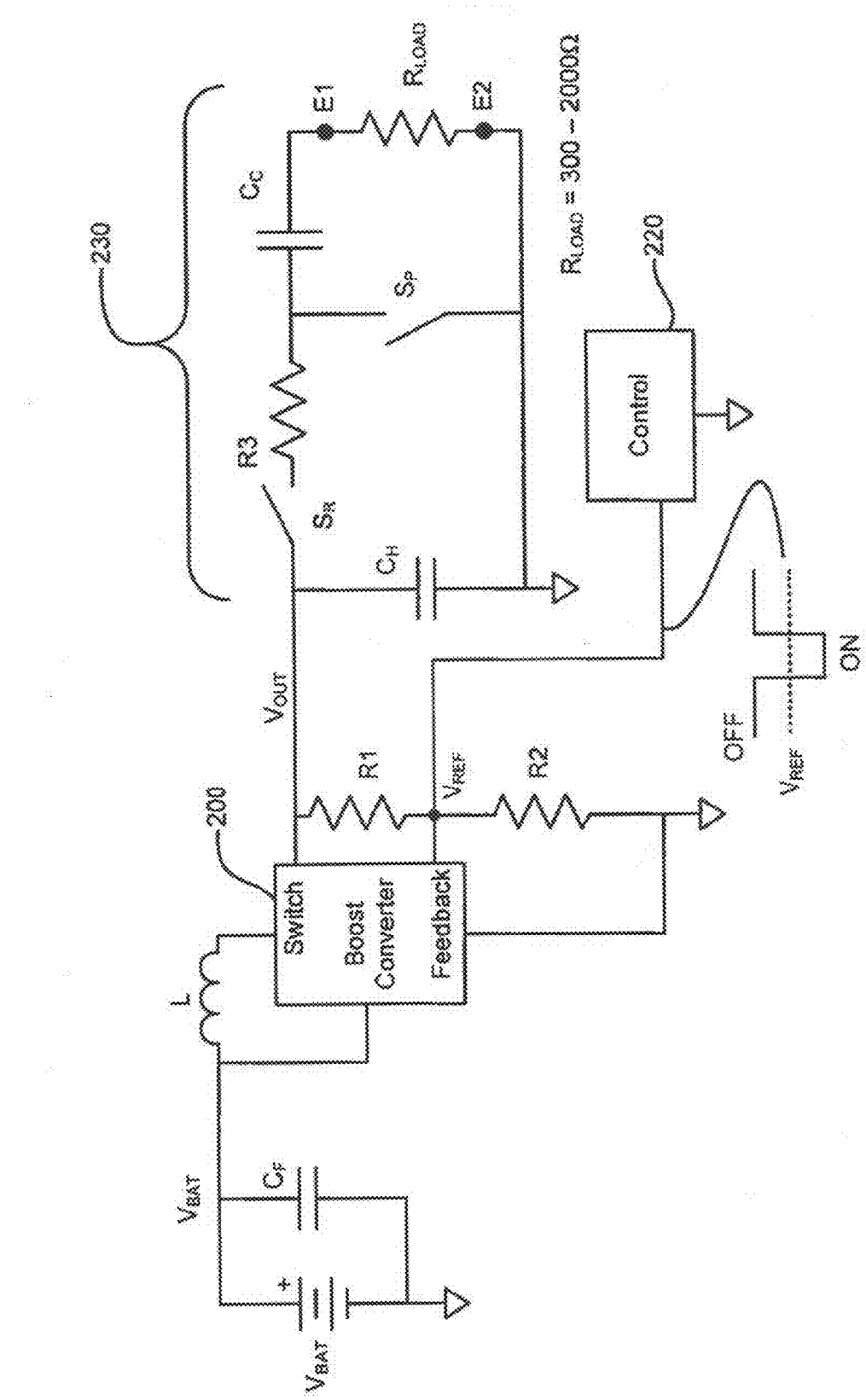
FIG. 11 shows an alternate boost converter circuit configuration and a functional pulse generation circuit for use within the IEAD.

An alternate embodiment of the electronic circuitry that may be used within the IDEA 100 is shown in FIG. 11. This circuit is in most respects the same as the circuitry shown in FIG. 10. However, in this alternate embodiment shown in FIG. 11, the boost converter circuit 200 does not have a specific shut down input control. Rather, as seen in FIG. 11, the boost converter circuit is shut down by applying a control voltage to the feedback input of the boost converter circuit 200 that is higher than $V_{REF}$. When this happens, i.e., when the control voltage applied to the feedback input is greater than $V_{REF}$, the boost converter will stop switching and draws little or no current from the battery. The value of $V_{REF}$ is typically a low enough voltage, such as a 1.2 V band-gap voltage, that a low level digital control signal can be used to disable the boost converter circuit. To enable the boost converter circuit, the control signal can be set to go to a high impedance, which effectively returns the node at the $V_{REF}$ terminal to the voltage set by the resistor divider network formed from R1 and R2. Alternatively the control signal can be set to go to a voltage less than $V_{REF}$.

A low level digital control signal that performs this function of enabling (turning ON) or disabling (turning OFF) the boost converter circuit is depicted in FIG. 11 as being generated at the output of a control circuit 220. The signal line on which this control signal is present connects the output of the control circuit 220 with the $V_{REF}$ node connected to the feedback input of the boost converter circuit. This control signal, as suggested by the waveform shown in FIG. 11, varies from a voltage greater than $V_{REF}$, thereby disabling or turning OFF the boost converter circuit, to a voltage less than $V_{REF}$, thereby enabling or turning on the boost converter circuit ON.

Figure 12:
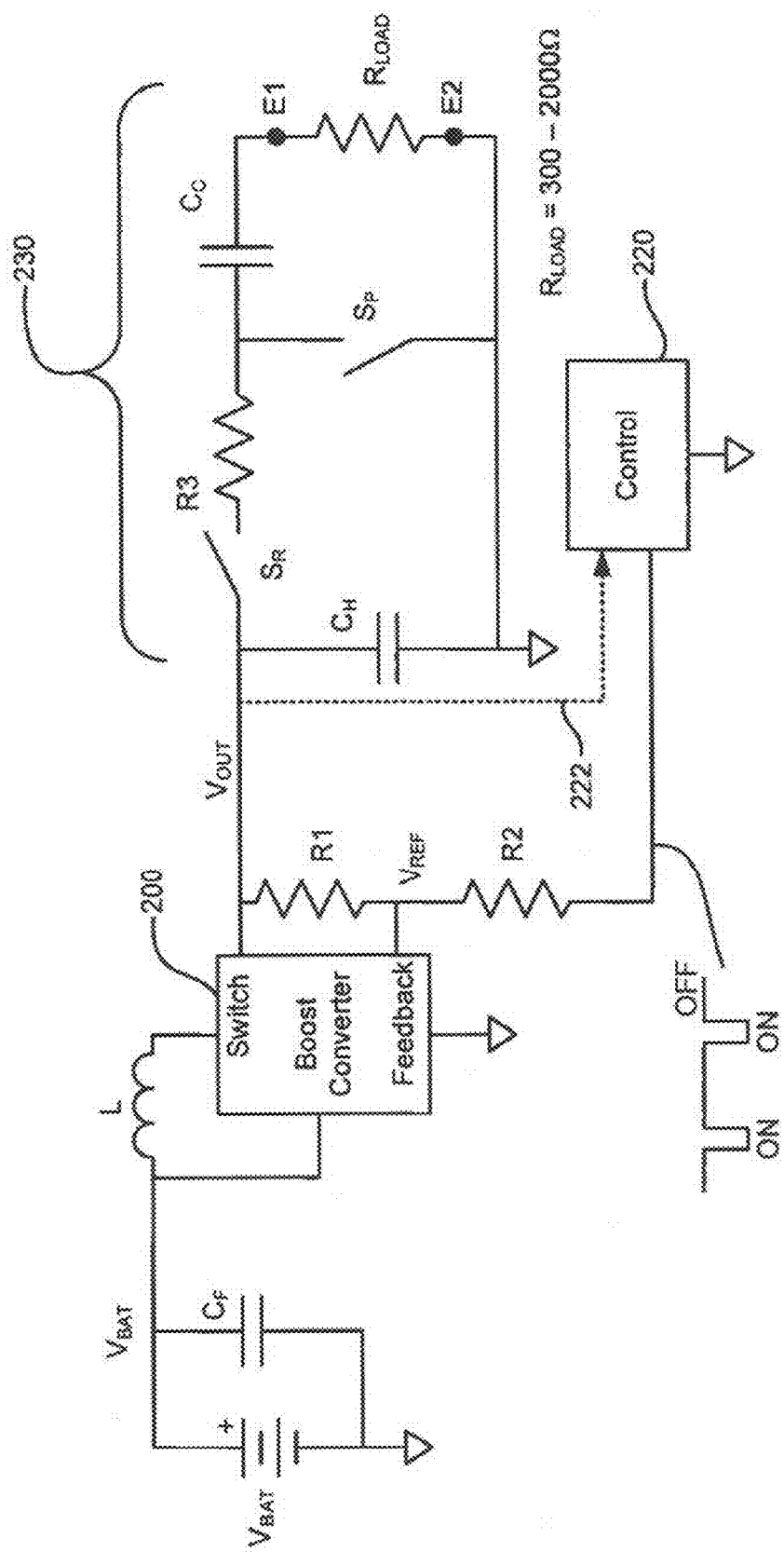
FIG. 12 shows a refinement of the circuit configuration of FIG. 11.

A refinement to the alternate embodiment shown in FIG. 11 is to use the control signal to drive the low side of R2 as shown in FIG. 12. That is, as shown in FIG. 12, the boost converter circuit 200 is shut down when the control signal is greater than $V_{REF}$ and runs when the control signal is less than $V_{REF}$. A digital control signal can be used to perform this function by switching between ground and a voltage greater than $V_{REF}$. This has the additional possibility of delta-sigma modulation control of $V_{OUT}$ if a measurement of the actual $V_{OUT}$ is available for feedback, e.g., using a signal line 222, to the controller.

Figure 13A:
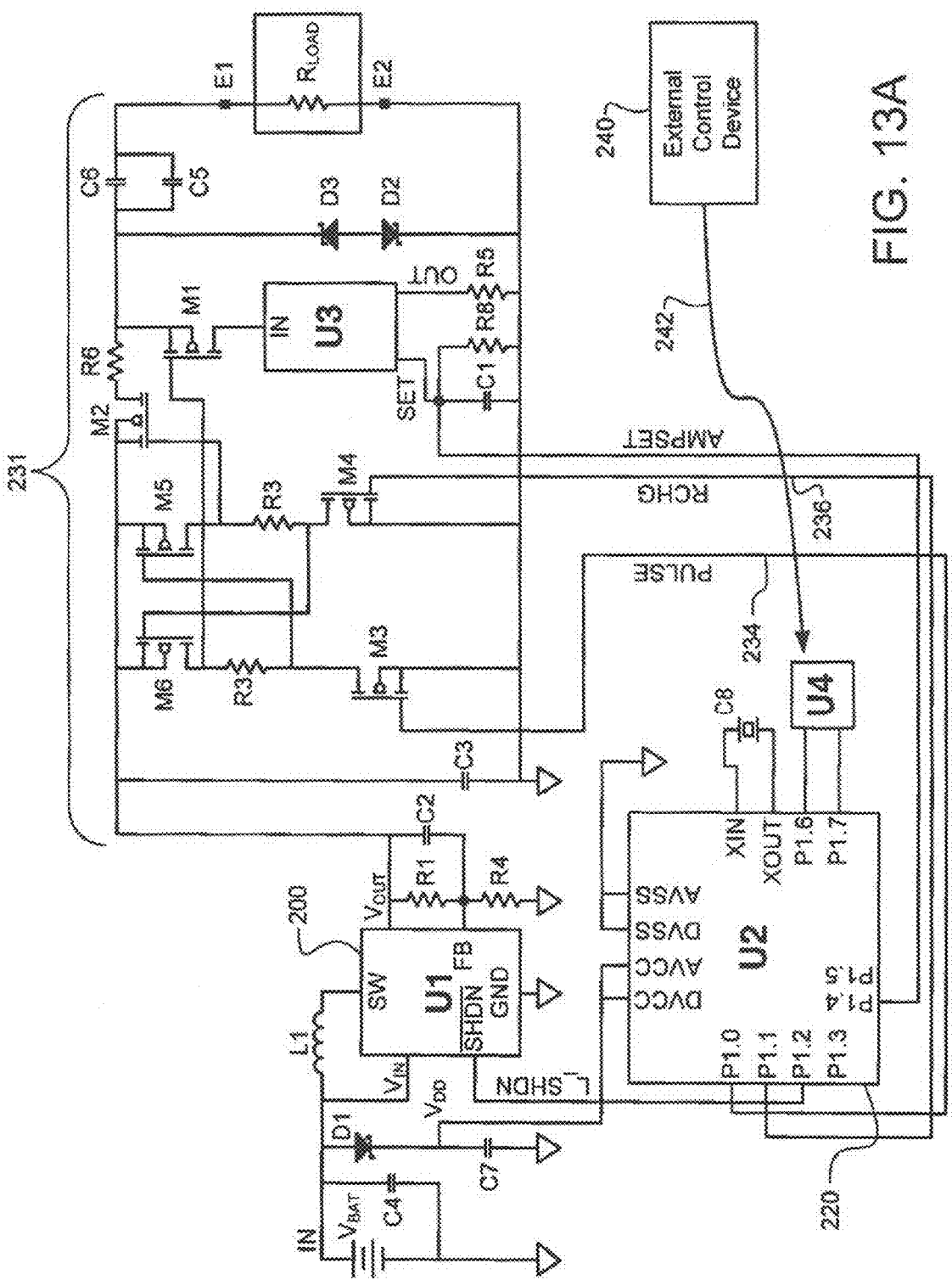
FIG. 13A shows one preferred schematic configuration for an implantable electroacupuncture device (IEAD) that utilizes the boost converter configuration shown in FIG. 10.

One preferred embodiment of the circuitry used in an implantable electroacupuncture device (IEAD) 100 that employs a digital control signal as taught herein is shown in the schematic diagram shown in FIG. 13A. In FIG. 13A, there are basically four integrated circuits (ICs) used as the main components. The IC U1 is a boost converter circuit, and performs the function of the boost converter circuit 200 described previously in connection with FIGS. 8B, 10, 11 and 12.

The IC U2 is a micro-controller IC and is used to perform the function of the control circuit 220 described previously in connection with FIGS. 10, 11 and 12. A preferred IC for this purpose is a MSP430G2452I micro-controller chip made by Texas Instruments. This chip includes 8 KB of Flash memory. Having some memory included with the micro-controller is important because it allows the parameters associated with a selected stimulation regimen to be defined and stored. One of the advantages of the IEAD described herein is that it provides a stimulation regimen that can be defined with just 5 parameters, as taught below in connection with FIGS. 15A and 15B. This allows the programming features of the micro-controller to be carried out in a simple and straightforward manner.

The micro-controller U2 primarily performs the function of generating the digital signal that shuts down the boost converter to prevent too much instantaneous current from being drawn from the battery $V_{BAT}$. The micro-controller U2 also controls the generation of the stimulus pulses at the desired pulse width and frequency. It further keeps track of the time periods associated with a stimulation session, i.e., when a stimulation session begins and when it ends.

The micro-controller U2 also controls the amplitude of the stimulus pulse. This is done by adjusting the value of a current generated by a Programmable Current Source U3. In one embodiment, U3 is realized with a voltage controlled current source IC. In such a voltage controlled current source, the programmed current is set by a programmed voltage appearing across a fixed resistor R5, i.e., the voltage appearing at the "OUT" terminal of U3. This programmed voltage, in turn, is set by the voltage applied to the "SET" terminal of U3. That is, the programmed current source U3 sets the voltage at the "OUT" terminal to be equal to the voltage applied to the "SET" terminal. The programmed current that flows through the resistor R5 is then set by Ohms Law to be the voltage at the "set" terminal divided by R5. As the voltage at the "set" terminal changes, the current flowing through resistor R5 at the "OUT" terminal changes, and this current is essentially the same as the current pulled through the closed switch M1, which is essentially the same current flowing through the load $R_{LOAD}$. Hence, whatever current flows through resistor R5, as set by the voltage across resistor R5, is essentially the same current that flows through the load $R_{LOAD}$. Thus, as the micro-controller U2 sets the voltage at the "set" terminal of U3, on the signal line labeled "AMPSET", it controls what current flows through the load $R_{LOAD}$. In no event can the amplitude of the voltage pulse developed across the load $R_{LOAD}$ exceed the voltage $V_{OUT}$ developed by the boost converter less the voltage drops across the switches and current source.

The switches $S_R$ and $S_P$ described previously in connection with FIGS. 10, 11 and 12 are realized with transistor switches M1, M2, M3, M4, M5 and M6, each of which is controlled directly or indirectly by control signals generated by the micro-controller circuit U2. For the embodiment shown in FIG. 13A, these switches are controlled by two signals, one appearing on signal line 234, labeled PULSE, and the other appearing on signal line 236, labeled RCHG (which is an abbreviation for "recharge"). For the circuit configuration shown in FIG. 13A, the RCHG signal on signal line 236 is always the inverse of the PULSE signal appearing on signal line 234. This type of control does not allow both switch M1 and switch M2 to be open or closed at the same time. Rather, switch M1 is closed when switch M2 is open, and switch M2 is closed, when switch M1 is open. When switch M1 is closed, and switch M2 is open, the stimulus pulse appears across the load, $R_{LOAD}$, with the current flowing through the load, $R_{LOAD}$, being essentially equal to the current flowing through resistor R5. When the switch M1 is open, and switch M2 is closed, no stimulus pulse appears across the load, and the coupling capacitors C5 and C6 are recharged through the closed switch M2 and resistor R6 to the voltage $V_{OUT}$ in anticipation of the next stimulus pulse.

The circuitry shown in FIG. 13A is only exemplary of one type of circuit that may be used to control the pulse width, amplitude, frequency, and duty cycle of stimulation pulses applied to the load, $R_{LOAD}$. Any type of circuit, or control, that allows stimulation pulses of a desired magnitude (measured in terms of pulse width, frequency and amplitude, where the amplitude may be measured in current or voltage) to be applied through the electrodes to the patient at the specified acupoint at a desired duty cycle (stimulation session duration and frequency) may be used. However, for the circuitry to perform its intended function over a long period of time, e.g., years, using only a small energy source, e.g., a small coin-sized battery having a high battery impedance and a relatively low capacity, the circuitry must be properly managed and controlled to prevent excessive current draw from the battery.

It is also important that the circuitry used in the IEAD 100, e.g., the circuitry shown in FIG. 10, 11, 12, 13A, or equivalents thereof, have some means for controlling the stimulation current that flows through the load, $R_{LOAD}$, which load may be characterized as the patient's tissue impedance at and around the acupoint being stimulated. This tissue impedance, as shown in FIGS. 11 and 12, may typically vary from between about 300 ohms to 2000 ohms. Moreover, it not only varies from one patient to another, but it varies over time. Hence, there is a need to control the current that flows through this variable load, $R_{LOAD}$. One way of accomplishing this goal is to control the stimulation current, as opposed to the stimulation voltage, so that the same current will flow through the tissue load regardless of changes that may occur in the tissue impedance over time. The use of a voltage controlled current source U3, as shown in FIG. 13A, is one way to satisfy this need.

Still referring to FIG. 13A, a fourth IC U4 is connected to the micro-controller U2. For the embodiment shown in FIG. 13A, the IC U4 is a magnetic sensor, and it allows the presence of an externally-generated (non-implanted) magnetic field to be sensed. Such magnetic field is generated using an External Control Device (ECD) 240 that communicates wirelessly, e.g., through the presence or absence of a magnetic field, with the magnetic sensor U4. (A magnetic field is symbolically illustrated in FIG. 13A by the wavy line 242.) In its simplest form, the ECD 240 may simply be a magnet, and modulation of the magnetic field is achieved simply by placing or removing the magnet next to or away from the IEAD.

Use of the ECD 240 provides a way for the patient, or medical personnel, to control the IEAD 100 after it has been implanted (or before it is implanted) with some simple commands, e.g., turn the IEAD ON, turn the IEAD OFF, increase the amplitude of the stimulation pulses by one increment, decrease the amplitude of the stimulation pulses by one increment, and the like. A simple coding scheme may be used to differentiate one command from another. For example, one coding scheme is time-based. That is, a first command is communicated by holding a magnet near the IEAD 100, and hence near the magnetic sensor U4 contained within the IEAD 100, for differing lengths of time. If, for example, a magnet is held over the IEAD for at least 2 seconds, but no more than 7 seconds, a first command is communicated. If a magnet is held over the IEAD for at least 11 seconds, but no more than 18 seconds, a second command is communicated, and so forth.

Another coding scheme that could be used is a sequence-based coding scheme. That is, application of 3 magnetic pulses may be used to signal one external command, if the sequence is repeated 3 times. A sequence of 2 magnetic pulses, repeated twice, may be used to signal another external command. A sequence of one magnetic pulse, followed by a sequence of two magnetic pulses, followed by a sequence of three magnetic pulses, may be used to signal yet another external command.

Other simple coding schemes may also be used, such as the letters AA, RR, HO, BT, KS using international Morse code. That is, the Morse code symbols for the letter "A" are dot dash, where a dot is a short magnetic pulse, and a dash is a long magnetic pulse. Thus, to send the letter A to the IEAD 100 using an external magnet, the user would hold the magnet over the area where the IEAD 100 is implanted for a short period of time, e.g., one second or less, followed by holding the magnet over the IEAD for a long period of time, e.g., more than one second.

More sophisticated magnetic coding schemes may be used to communicate to the micro-controller chip U2 the operating parameters of the IEAD 100. For example, using an electromagnet controlled by a computer, the pulse width, frequency, and amplitude of the EA stimulation pulses used during each stimulation session may be pre-set. Also, the frequency of the stimulation sessions can be pre-set. Additionally, a master reset signal can be sent to the device in order to re-set these parameters to default values. These same operating parameters and commands may be re-sent at any time to the IEAD 100 during its useful lifetime should changes in the parameters be desired or needed.

Figure 13B:
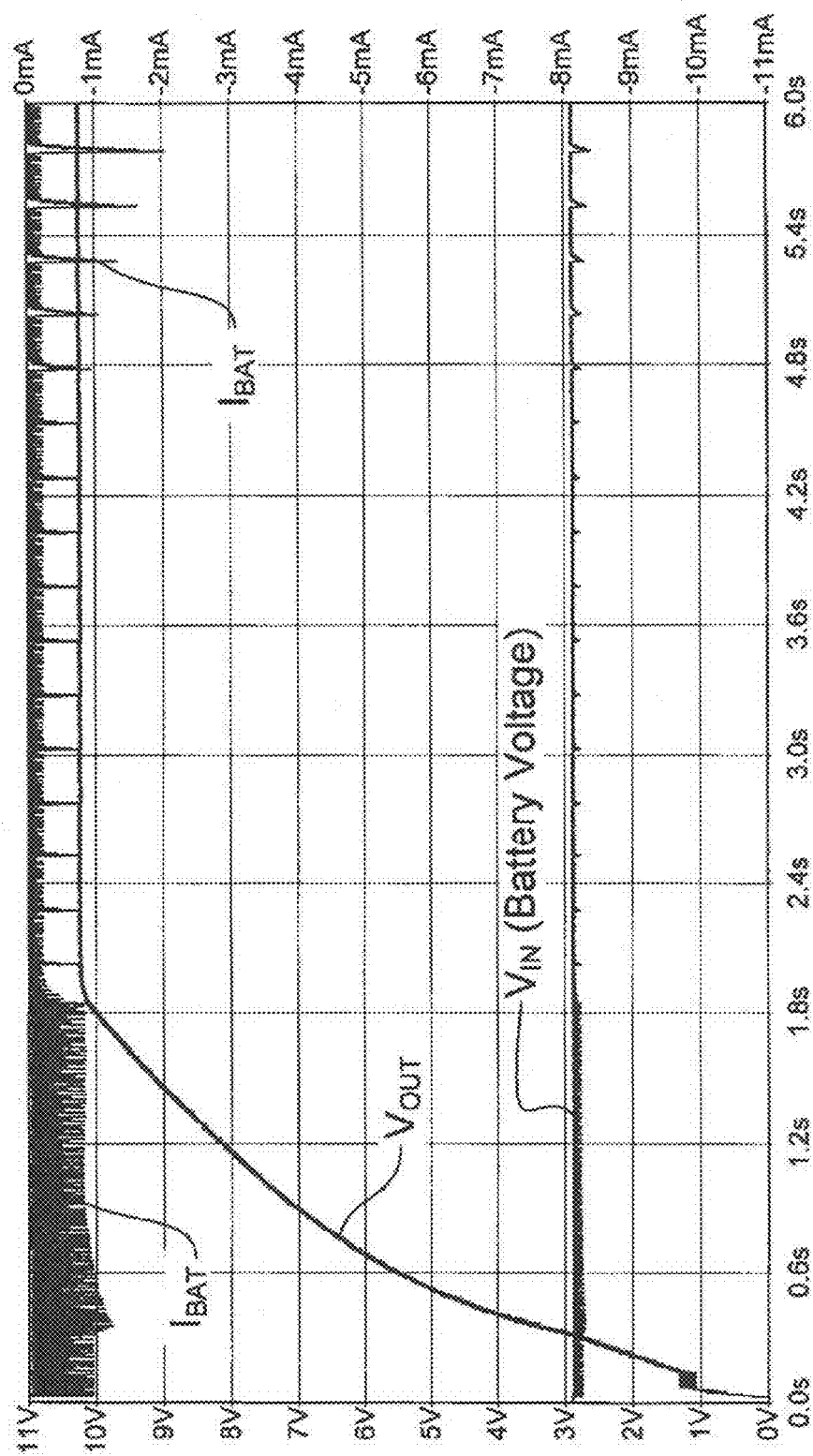
FIG. 13B shows current and voltage waveforms associated with the operation of the circuit shown in FIG. 13A.

The current and voltage waveforms associated with the operation of the IEAD circuitry of FIG. 13A are shown in FIG. 13B. In FIG. 13B, the horizontal axis is time, the left vertical axis is voltage, and the right vertical axis is current. The battery in this example has 160 Ohms of internal impedance.

Referring to FIGS. 13A and 13B, during startup, the boost converter ON time is approximately 30 microseconds applied every 7.8 milliseconds. This is sufficient to ramp the output voltage $V_{OUT}$ up to over 10 V within 2 seconds while drawing no more than about 1 mA from the battery and inducing only 150 mV of input voltage ripple.

The electroacupuncture (EA) simulation pulses resulting from operation of the circuit of FIG. 13 have a width of 0.5 milliseconds and increase in amplitude from approximately 1 mA in the first pulse to approximately 15 mA in the last pulse. The instantaneous current drawn from the battery is less than 2 mA for the EA pulses and the drop in battery voltage is less than approximately 300 mV. The boost converter is enabled (turned ON) only during the instantaneous output current surges associated with the 0.5 milliseconds wide EA pulses.

Figure 14:
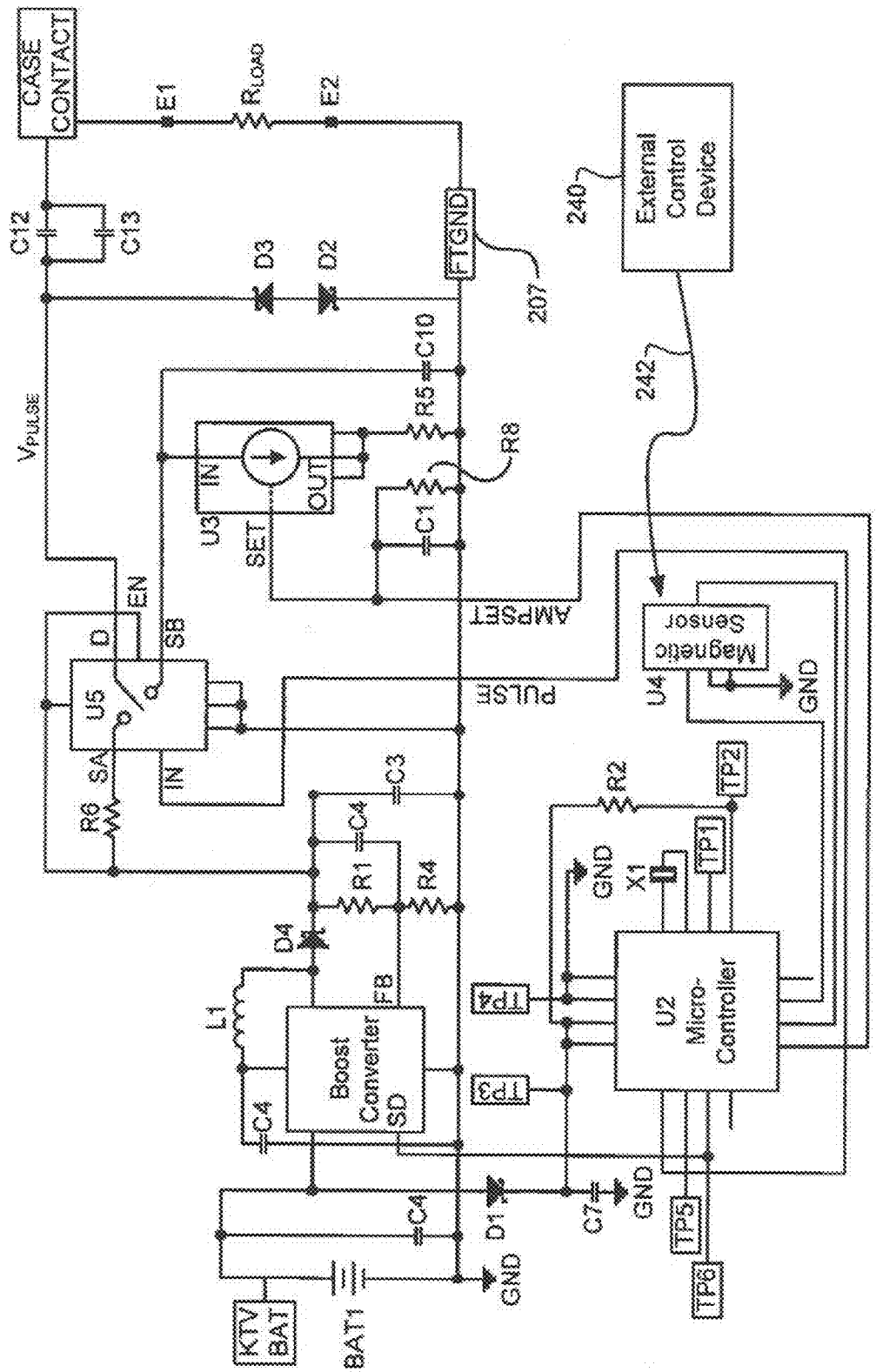
FIG. 14 shows another preferred schematic configuration for an IEAD similar to that shown in FIG. 13A, but which uses an alternate output circuitry configuration for generating the stimulus pulses.

Another preferred embodiment of the circuitry used in an implantable electroacupuncture device (IEAD) 100 that employs a digital control signal as taught herein is shown in the schematic diagram of FIG. 14. The circuit shown in FIG. 14 is, in most respects, very similar to the circuit described previously in connection with FIG. 13A. What is new in FIG. 14 is the inclusion of an external Schottky diode D4 at the output terminal LX of the boost convertor U1 and the inclusion of a fifth integrated circuit (IC) U5 that essentially performs the same function as the switches M1-M6 shown in FIG. 13A.

The Schottky diode D5 helps isolate the output voltage $V_{OUT}$ generated by the boost converter circuit U1. This is important in applications where the boost converter circuit U1 is selected and operated to provide an output voltage $V_{OUT}$ that is four or five times as great as the battery voltage, $V_{BAT}$. For example, in the embodiment for which the circuit of FIG. 14 is designed, the output voltage $V_{OUT}$ is designed to be nominally 15 volts using a battery that has a nominal battery voltage of only 3 volts. (In contrast, the embodiment shown in FIG. 13A is designed to provide an output voltage that is nominally 10-12 volts, using a battery having a nominal output voltage of 3 volts.)

The inclusion of the fifth IC U5 in the circuit shown in FIG. 14 is, as indicated, used to perform the function of a switch. The other ICs shown in FIG. 14, U1 (boost converter), U2 (micro-controller), U3 (voltage controlled programmable current source) and U4 (magnetic sensor) are basically the same as the IC's U1, U2, U3 and U4 described previously in connection with FIG. 13A.

The IC U5 shown in FIG. 14 functions as a single pole/double throw (SPDT) switch. Numerous commercially-available ICs may be used for this function. For example, an ADG1419 IC, available from Analog Devices Incorporated (ADI) may be used. In such IC U5, the terminal "D" functions as the common terminal of the switch, and the terminals "SA" and "SB" function as the selected output terminal of the switch. The terminals "IN" and "EN" are control terminals to control the position of the switch. Thus, when there is a signal present on the PULSE line, which is connected to the "IN" terminal of U5, the SPDT switch U5 connects the "D" terminal to the "SB" terminal, and the SPDT switch U5 effectively connects the cathode electrode E1 to the programmable current source U3. This connection thus causes the programmed current, set by the control voltage AMPSET applied to the SET terminal of the programmable current source U3, to flow through resistor R5, which in turn causes essentially the same current to flow through the load, $R_{LOAD}$, present between the electrodes E1 and E2. When a signal is not present on the PULSE line, the SPDT switch U5 effectively connects the cathode electrode E1 to the resistor R6, which allows the coupling capacitors C12 and C13 to recharge back to the voltage $V_{OUT}$ provided by the boost converter circuit U2.

From the above description, it is seen that an implantable IEAD 100 is provided that uses a digital control signal to duty-cycle limit the instantaneous current drawn from the battery by a boost converter. Three different exemplary configurations (FIGS. 10, 11 and 12) are taught for achieving this desired result, and two exemplary circuit designs that may be used to realize this result have been disclosed (FIGS. 13A and 14). One configuration (FIG. 12) teaches the additional capability to delta-sigma modulate the boost converter output voltage.

Delta-sigma modulation is well described in the art. Basically, it is a method for encoding analog signals into digital signals or higher-resolution digital signals into lower-resolution digital signals. The conversion is done using error feedback, where the difference between the two signals is measured and used to improve the conversion. The low-resolution signal typically changes more quickly than the high-resolution signal and it can be filtered to recover the high resolution signal with little or no loss of fidelity. Delta-sigma modulation has found increasing use in modern electronic components such as converters, frequency synthesizers, switched-mode power supplies and motor controllers. See, e.g., Wikipedia, Delta-sigma modulation.

Use and Operation

With the implantable electroacupuncture device (IEAD) 100 in hand, the IEAD 100 may be used most effectively to treat depression, bipolar disorder and Anxiety by first presetting stimulation parameters that the device will use during a stimulation session. FIG. 15A shows a timing waveform diagram illustrating the EA stimulation parameters used by the IEAD to generate EA stimulation pulses. As seen in FIG. 15A, there are basically four parameters associated with a stimulation session. The time T1 defines the duration (or pulse width) of a stimulus pulse. The time T2 defines the time between the start of one stimulus pulse and the start of the next stimulus pulse. The time T2 thus defines the period associated with the frequency of the stimulus pulses. The frequency of the stimulation pulses is equal to 1/T2. The ratio of T1/T2 is typically quite low, e.g., less than 0.01. The duration of a stimulation session is defined by the time period T3. The amplitude of the stimulus pulses is defined by the amplitude A1. This amplitude may be expressed in either voltage or current.

Figure 15B:
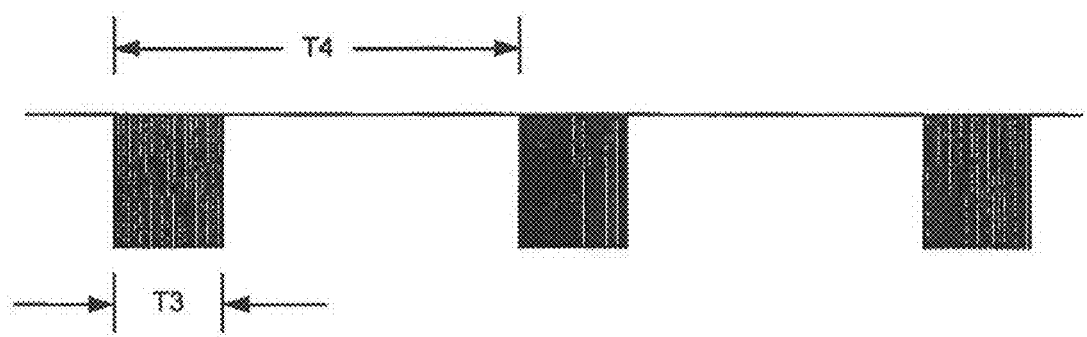
FIG. 15B shows a timing waveform diagram of multiple stimulation sessions, and illustrates the waveforms on a more condensed time scale.

Turning next to FIG. 15B, a timing waveform diagram is shown that illustrates the manner in which the stimulation sessions are administered in accordance with a preferred stimulation regimen. FIG. 15B shows several stimulation sessions of duration T3, and how often the stimulation sessions occur. The stimulation regimen thus includes a time period T4 which sets the time period from the start of one stimulation session to the start of the next stimulation session. The time period T4 is thus the period of the stimulation session frequency, and the stimulation session frequency is equal to 1/T4.

By way of example, one set of parameters that could be used to define a stimulation regimen is T1=0.5 milliseconds
T2=500 milliseconds
T3=60 minutes
T4=7 days (10,080 minutes)
A1=6 volts (across 1 kOhm), or 6 milliamperes (mA)

It is to be emphasized that the values shown above for the stimulation regimen are representative of only one preferred stimulation regimen that could be used. Other stimulation regimens that could be used, and the ranges of values that could be used for each of these parameters, are as defined in the claims.

It is also emphasized that the ranges of values presented in the claims for the parameters used with the invention have been selected after many months of careful research and study, and are not arbitrary. For example, the ratio of T3/T4, which sets the duty cycle, has been carefully selected to be very low, e.g., no more than 0.05. Maintaining a low duty cycle of this magnitude represents a significant change over what others have attempted in the implantable stimulator art. Not only does a very low duty cycle allow the battery itself to be small (coin cell size), which in turn allows the IEAD housing to be very small, which makes the IEAD ideally suited for being used without leads, thereby making it relatively easy to implant the device at the desired acupuncture site, but it also limits the frequency and duration of stimulation sessions. Limiting the frequency and duration of the stimulation sessions is a key aspect of Applicant's invention because it recognizes that some treatments, such as treating depression, bipolar disorder and Anxiety, are best done slowly and methodically, over time, rather than quickly and harshly using large doses of stimulation (or other treatments) aimed at forcing a rapid change in the patient's condition. Moreover, applying treatments slowly and methodically is more in keeping with traditional acupuncture methods (which, as indicated previously, are based on over 2500 years of experience). Thus, Applicant has based its treatment regimens on the slow-and-methodical approach, as opposed to the immediate-and-forced approach adopted by many, if not most, prior art implantable electrical stimulators.

Once the stimulation regimen has been defined and the parameters associated with it have been pre-set into the memory of the micro-controller circuit 220, the IEAD 100 needs to be implanted. Implantation is usually a simple procedure, and is described above in connection with the description of FIGS. 1A and 1B, as well as FIGS. 17A and 17B.

For treating the specific conditions of brain mood disorders targeted by this embodiment of the invention, i.e., depression, bipolar disorder and Anxiety, the specified acupoint at which the EA stimulation pulses should be applied in accordance with a selected stimulation regimen is, for purposes of the invention described and claimed herein, GV20 and/or EXHN3. As indicated previously, acupoint GV20 is located on the head at the midpoint of the connecting line between the auricular apices. It is also about 4.5 inches superior to the anterior hairline on the anterior median line. See FIG. 1B and Appendix D. Acupoint EXHN3, also referred to herein as acupoint GV24.5, is located on the forehead at the midpoint between the two medial ends of the eyebrow. See FIG. 1A and Appendix D.

Figure 16:
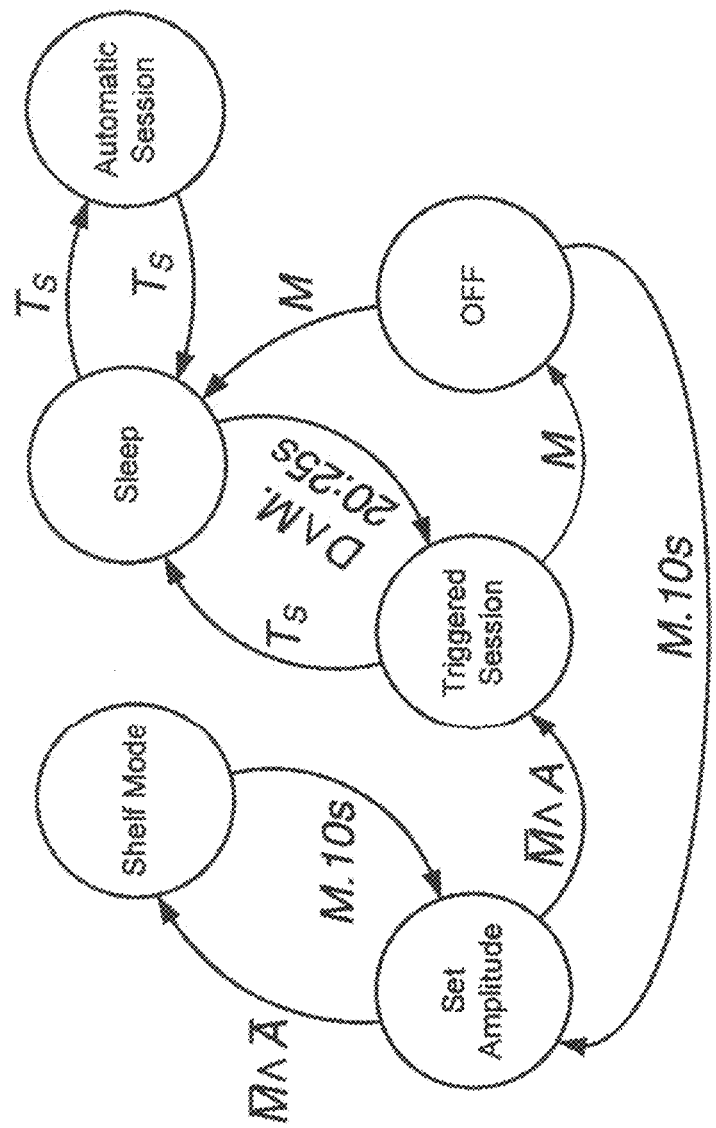
FIG. 16 shows a state diagram that shows the various states in which the IEAD may be placed through the use of an external magnet.

After implantation, the IEAD must be turned ON, and otherwise controlled, so that the desired stimulation regimen may be carried out. In one preferred embodiment, control of the IEAD after implantation, as well as anytime after the housing of the IEAD has been hermetically sealed, is performed as shown in the state diagram of FIG. 16. Each circle shown in FIG. 16 represents a "state" that the micro-controller U2 (in FIG. 13A or 14) may operate in under the conditions specified. As seen in FIG. 16, the controller U2 only operates in one of six states: (1) a "Set Amplitude" state, (2) a "Shelf Mode" state, (3) a "Triggered Session" state, (4) a "Sleep" state, (5) an "OFF" state, and an (6) "Automatic Session" state. The "Automatic Session" state is the state that automatically carries out the stimulation regimen using the pre-programmed parameters that define the stimulation regimen.

Shelf Mode is a low power state in which the IEAD is placed prior to shipment. After implant, commands are made through magnet application. Magnet application means an external magnet, typically a small hand-held cylindrical magnet, is placed over the location where the IEAD has been implanted. With a magnet in that location, the magnetic sensor U4 senses the presence of the magnet and notifies the controller U2 of the magnet's presence.

From the "Shelf Mode" state, a magnet application for 10 seconds (M.10s) puts the IEAD in the "Set Amplitude" state. While in the "Set Amplitude" state, the stimulation starts running by generating pulses at zero amplitude, incrementing every five seconds until the patient indicates that a comfortable level has been reached. At that time, the magnet is removed to set the amplitude.

If the magnet is removed and the amplitude is non-zero ($\overline{M}$^A), the device continues into the "Triggered Session" so the patient receives the initial therapy. If the magnet is removed during "Set Amplitude" while the amplitude is zero ($\overline{M}$^$\overline{A}$), the device returns to the Shelf Mode.

The Triggered Session ends and stimulation stops after the session time ($T_S$) has elapsed and the device enters the "Sleep" state. If a magnet is applied during a Triggered Session (M), the session aborts to the "OFF" state. If the magnet remains held on for 10 seconds (M.10s) while in the "OFF" state, the "Set Amplitude" state is entered with the stimulation level starting from zero amplitude as described.

If the magnet is removed ($\overline{M}$) within 10 seconds while in the OFF state, the device enters the Sleep state. From the Sleep state, the device automatically enters the Automatic Session state when the session interval time has expired ($T_I$). The Automatic Session delivers stimulation for the session time ($T_S$) and the device returns to the Sleep state. In this embodiment, the magnet has no effect once the Automatic Session starts so that the full therapy session is delivered.

While in the Sleep state, if a magnet has not been applied in the last 30 seconds (D) and a magnet is applied for a window between 20-25 seconds and then removed (M.20:25s), a Triggered Session is started. If the magnet window is missed (i.e. magnet removed too soon or too late), the 30 second de-bounce period (D) is started. When de-bounce is active, no magnet must be detected for 30 seconds before a Triggered Session can be initiated.

The session interval timer runs while the device is in Sleep state. The session interval timer is initialized when the device is woken up from Shelf Mode and is reset after each session is completely delivered. Thus abort of a triggered session by magnet application will not reset the timer, the Triggered Session must be completely delivered.

The circuitry that sets the various states shown in FIG. 16 as a function of externally-generated magnetic control commands, or other externally-generated command signals, is the micro-controller U2 (FIG. 14), the processor U2 (FIG. 13A), or the control circuit 220 (FIGS. 10, 11 and 12). Such processor-type circuits are programmable circuits that operate as directed by a program. The program is often referred to as "code", or a sequence of steps that the processor circuit follows. The "code" can take many forms, and be written in many different languages and formats, known to those of skill in the art. Representative "code" for the micro-controller U2 (FIG. 14) for controlling the states of the IEAD as shown in FIG. 16 is found in Appendix C, attached hereto, and incorporated by reference herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An Implantable ElectroAcupuncture Device (IEAD) for treating depression, bipolar disorder, or anxiety, adapted for application of electroacupuncture (EA) stimulation pulses substantially at or near at least one of acupoints GV20 and EXHN3 of a patient, comprising:
a small, thin, leadless coin-sized and coin-shaped IEAD housing having a symmetrical electrode configuration thereon that includes at least two electrodes/arrays, a longest linear dimension of the IEAD housing being no greater than about 25 mm, wherein at least one of said at least two electrodes/arrays comprises a central electrode/array located substantially in a center of a first surface of the IEAD housing, and wherein at least another of said at least two electrodes/arrays comprises a circumferential electrode/array located substantially around and at least 5 mm distant from the center of the central electrode/array, wherein the first surface of the IEAD housing when implanted is adapted to face selected target tissue at or near at least one of acupoints GV20 and EXHN3;
pulse generation circuitry located within the IEAD housing and electrically coupled to the at least two electrodes/arrays, wherein said pulse generation circuitry, once turned on, is adapted to continuously deliver stimulation sessions in accordance with a specified stimulation regimen to the at least two electrodes/arrays adapted for placement at or near the patient's body tissue near at least one of acupoints GV20 and EXHN3, said stimulation regimen defining the duration and rate at which a stimulation session is applied to the patient, said stimulation regimen requiring that the stimulation session have a duration of T3 minutes, where T3 is at least 10 minutes, and a rate of occurrence of once every T4 minutes, wherein the ratio of T3/T4 is no greater than 0.05, and wherein during each stimulation session EA stimulation pulses having one or more specified widths and amplitudes are generated at one or more specified rates;
a primary battery contained within the IEAD housing and electrically coupled to the pulse generation circuitry, said primary battery having a nominal output voltage of 3 volts, and an internal impedance greater than 5 ohms; and
a magnetic sensor contained within the IEAD housing responsive to a presence or absence of a magnetic field placed near the IEAD housing, the sensed presence/absence of the magnetic field in a prescribed sequence allowing the pulse generation circuitry to be turned on, thereby allowing limited external control of the IEAD.

2. The IEAD of claim 1 wherein the central electrode/array comprises an electrode array having no more than 4 segments, the central electrode array having a maximum linear dimension of no greater than about 7 mm.

3. The IEAD of claim 2 wherein the circumferential electrode/array comprises an electrode array having no more than 4 electrode segments positioned around the central electrode/array.

4. The IEAD of claim 3 wherein the circumferential electrode/array comprises an anode electrode/array and the central electrode/array comprises a cathode electrode/array.

5. The IEAD of claim 3 wherein the circumferential electrode/array comprises a cathode electrode/array and the central electrode/array comprises an anode electrode/array.

6. The IEAD of claim 1 wherein the IEAD housing is coin-shaped having a diameter no greater than about 25 mm and a thickness of no greater than about 2.5 mm.

7. The IEAD of claim 1 wherein the IEAD housing is oval shaped having a maximum linear dimension of no greater than about 25 mm and a thickness of no greater than about 2.5 mm.

8. The IEAD of claim 1 wherein the duration of the stimulation session T3 varies between 10 minutes and 70 minutes and the rate of occurrence of the stimulation session T4 is set to a value between 1440 minutes [1 day] and 20,160 minutes [14 days].

9. The IEAD of claim 1 wherein the pulse generation circuitry includes:
a boost converter circuit that boosts the nominal voltage of the primary battery to an output voltage $V_{OUT}$ that is at least three times the nominal battery voltage;
a control circuit that selectively turns the boost converter circuit OFF and ON to limit the amount of current that may be drawn from the primary battery; and
an output circuit powered by $V_{OUT}$ and controlled by the control circuit that generates the EA stimulation pulses as defined by the specified stimulation regimen.

10. The IEAD of claim 9 wherein the EA stimulation pulses generated by the pulse generation circuit are delivered through the at least two electrodes/arrays into a load at the specified acupoint comprise voltage pulses having a voltage amplitude of no less than about 1 V and no greater than about 15 V.

11. The IEAD of claim 9 wherein the EA stimulation pulses generated by the pulse generation circuit are delivered through the at least two electrodes/arrays into a load at the specified acupoint comprise current pulses having a current amplitude of no less than about 1 milliampere (mA) and no greater than about 15 mA.

12. The IEAD of claim 9 wherein the primary battery has sufficient capacity to power the pulse generation circuitry in accordance with the specified stimulation regimen for a minimum of 2 years.

13. A method of treating depression, bipolar disorder, or anxiety in a patient using a small, leadless, coin-sized and coin shaped implantable electroacupuncture device (IEAD) powered by a small disc primary battery having a specified nominal output voltage of 3 volts, and having an internal impedance of at least 5 ohms, the IEAD being configured, using self-contained electronic circuitry within the IEAD, to generate electroacupuncture (EA) stimulation pulses in accordance with a specified stimulation regimen and apply the EA stimulation pulses to at least two electrodes/arrays located on an outside surface of a housing of the IEAD and configured in a symmetrical pattern, said at least two electrodes/arrays comprising at least one central electrode/array of a first polarity, having a maximum width of no more 7 mm, centrally located on a first surface of the IEAD housing, and at least one annular electrode/array of a second polarity spaced apart from the central electrode/array by at least 5 mm measured from the edge of the annular electrode/array closest to the central electrode/array to the center of the central electrode/array, said method comprising:
(a) implanting the IEAD below the skin surface of the patient at at least one acupoint selected from acupoints GV20 and EXHN3, with the first surface of the IEAD facing a target tissue location associated with the selected acupoint;
(b) enabling the IEAD to provide stimulation pulses in accordance with a stimulation regimen that continuously provides a stimulation session at a rate of once every T4 minutes, with each stimulation session having a duration of T3 minutes, where T3 is at least 10 minutes, and where the ratio of T3/T4 is no greater than 0.05.

14. The method of claim 13 further including setting the time T4 to be at least 720 minutes [½ day], but no more than about 20,160 minutes [14 days].

15. The method of claim 14 further setting T3, the duration of the stimulation session, to a value between 20 minutes and 72 minutes if T4, the rate of occurrence of the stimulation session, is set to a value between 1,440 minutes and 20,160 minutes [14 days]; and setting T3 to a value between 10 minutes and a maximum T3 value, T3(max), if T4 is set to a value between 720 minutes and 1,440 minutes, wherein T3(max) varies as a function of T4 as defined by the equation:

$$T3(max)=0.05*T4.$$

16. The method of claim 14 further including setting the stimulation pulses during a stimulation session to have a duration of T1 seconds, that occur at a rate of once every T2 seconds, where the ratio of T1/T2 is no greater than 0.01.

17. The method of claim 16 further including setting the time T1 to be 0.1 to 1.0 millisecond and the time T2 to be 250 to 1000 milliseconds.

18. The method of claim 13 further including controlling the electronic circuits within the IEAD to limit instantaneous current drawn from the small disc primary battery so that the output voltage of the primary battery does not drop more than about 11% below the output voltage of the primary battery when current is being drawn from the primary battery, where the output voltage of the primary battery is equal to the specified nominal output voltage of the primary battery less the voltage drop caused by the instantaneous current flowing through the internal impedance of the primary battery.

19. The method of claim 18 wherein the electronic circuitry within the IEAD includes a boost converter circuit, and wherein the method of controlling the electronic circuits within the IEAD to limit the instantaneous current drawn from the battery comprises modulating the operation of the boost converter circuit between an ON state and an OFF state.

20. A method for treating depression, bipolar disorder or anxiety in a patient comprising the steps of:
(a) implanting a small, thin, coin-sized and coin-shaped, leadless, electroacupuncture (EA) device in the patient below the patient's skin at at least one specified acupoint;
(b) enabling the EA device to generate stimulation sessions at a duty cycle that is less than or equal to 0.05, each stimulation session comprising a series of stimulation pulses, wherein the duty cycle is the ratio of T3/T4, where T3 is the duration in minutes of each stimulation session, wherein T3 is at least 10 minutes, and T4 is the time in minutes between stimulation sessions; and
(c) continuously delivering the stimulation pulses of each stimulation session to the at least one specified acupoint through at least two electrodes/arrays attached to an outside surface of the EA device in a slow and methodical manner that is adapted to gradually condition and remodel the patient's central nervous system so as to produce a sustained therapeutic benefit for patient.

21. The method of treating depression, bipolar disorder, or anxiety of claim 20 wherein the at least one specified acupoint at which the stimulation pulses are applied is selected from the group of acupoints that includes acupoints GV20 and EXHN3.

22. The method of treating depression, bipolar disorder or anxiety of claim 20 further comprising forming the at least two electrodes/arrays attached to the outside surface of the EA device in a concentric pattern, with one electrode/array of the at least two electrodes/arrays comprising a central electrode/array, and with another electrode of the at least two electrodes/arrays comprising an annular electrode/array that surrounds the central electrode/array, wherein the spacing between the center of the central electrode/array and an edge of the annular electrode/array closest to the central electrode/array comprises at least 5 mm.

23. The method of treating depression, bipolar disorder or anxiety of claim 22 further including forming the annular electrode/array as a ring electrode/array attached around a perimeter edge of the coin-sized EA device.

24. The method of treating depression, bipolar disorder or anxiety of claim 23 further including configuring the central electrode/array as a cathode electrode and the perimeter-edge ring electrode/array as an anode electrode.

25. The method of treating depression, bipolar disorder or anxiety of claim 20 wherein enabling the EA device to generate stimulation sessions includes generating the series of stimulation pulses within each stimulation session so that each stimulation pulse has a duration of between 0.1 and 1.0 millisecond and occurs at a rate of between 1 and 3 Hz.

26. The method of treating depression, bipolar disorder or anxiety of claim 20 further including setting the time T4, the time between stimulation sessions, to be at least 1440 minutes [1 day] but no longer than 20,160 minutes [14 days].

27. The method of treating depression, bipolar disorder or anxiety of claim 26 further setting T3, the duration of the stimulation session, to a value between 10 minutes and 72 minutes.

28. A method of assembling an implantable electroacupuncture device (IEAD) for use in treating depression, bipolar disorder or anxiety in a thin, hermetically-sealed, coin-sized housing having at least one feed-through pin assembly radially passing through a wall of the coin-sized housing that isolates the feed-through pin assembly from high temperature damage that could occur when the coin-sized housing is welded shut to hermetically-seal its contents, the method comprising the steps of:
(a) forming a coin-sized housing having a bottom case and a top cover plate, the top cover plate being adapted to fit over the bottom case, the bottom case having a longest linear dimension D2 of no more than about 25 mm and a perimeter side wall extending all the way around the perimeter of the bottom case, the perimeter side wall having a height W2, wherein the ratio of W2 to D2 is no greater than about 0.13;
(b) forming a recess in one segment of the side wall, said recess extending radially inwardly from the side wall to a depth D3, said recess having an opening in a bottom wall portion thereof;
(c) hermetically sealing a feed-through assembly in the opening in the bottom of the recess, the feed-through assembly having a feed-through pin that passes through the opening without contacting the edges of the opening, a distal end of the pin extending radially outward beyond the side wall of the bottom case, and a proximal end of the feed-through pin extending radially inward toward a center of the bottom case, whereby the feed-through assembly is hermetically bonded to the opening in the side wall at a location in the bottom of the recess that is located a distance D3 from the perimeter side wall, thereby thermally and mechanically isolating the feed-through assembly from high temperatures and residual weld stresses that occur at the perimeter side wall when the cover plate is welded to the edge of the perimeter side wall in step (e);
(d) attaching a central electrode to the thin coin-sized housing at a central location on a bottom outside surface of the housing;

(e) inserting an electronic circuit assembly, including a battery, inside of the bottom case, and connecting the proximal end of the feed-though pin to an output terminal of the electronic circuit assembly, and electrically connecting the bottom case to a reference terminal of the battery;

(f) welding the top cover plate to the edges of the side wall of the bottom case, thereby hermetically sealing the electronic circuit assembly, including the battery, inside of the IEAD housing, the IEAD housing comprising the assembly resulting from welding the top cover plate to the bottom case, the top cover plate forming a top surface of the IEAD housing, and a surface of the IEAD housing opposite the top surface comprising a bottom surface of the IEAD housing;

(g) placing an insulating layer of non-conductive material around the perimeter edge of the IEAD housing;

(h) placing a circumscribing electrode over the insulating layer of non-conductive material around the perimeter edge of the IEAD housing, and then electrically connecting the distal end of the feed-through pin to circumscribing electrode; and (i) covering all external surface areas of the IEAD housing with a layer of non-conductive material except for the circumscribing electrode around the perimeter of the IEAD housing and the central electrode centrally located on the bottom surface of the IEAD housing.

* * * * *